US012371500B2

(12) United States Patent
Durum et al.

(10) Patent No.: US 12,371,500 B2
(45) Date of Patent: *Jul. 29, 2025

(54) IL-7R-ALPHA SPECIFIC ANTIBODIES FOR TREATING ACUTE LYMPHOBLASTIC LEUKEMIA

(71) Applicants: The United States of America, as represented by the Secretary, Department of Health and Human Services, Bethesda, MD (US); University of Maryland, College Park, College Park, MD (US)

(72) Inventors: Scott Durum, Frederick, MD (US); Julie Hixon, Hagerstown, MD (US); Wen Qing Li, Frederick, MD (US); Scott Walsh, College Park, MD (US); Lila Kashi, College Park, MD (US)

(73) Assignees: The United States of America, as represented by the Secretary, Department of Health and Human Services, Bethesda, MD (US); University of Maryland, College Park, College Park, MD (US)

( * ) Notice: Subject to any disclaimer, the term of this patent is extended or adjusted under 35 U.S.C. 154(b) by 994 days.

This patent is subject to a terminal disclaimer.

(21) Appl. No.: 17/392,075

(22) Filed: Aug. 2, 2021

(65) Prior Publication Data
US 2022/0064309 A1  Mar. 3, 2022

Related U.S. Application Data

(63) Continuation of application No. 16/459,396, filed on Jul. 1, 2019, now Pat. No. 11,111,306, which is a continuation of application No. 15/760,193, filed as application No. PCT/US2016/055957 on Oct. 7, 2016, now Pat. No. 10,392,441.

(60) Provisional application No. 62/238,612, filed on Oct. 7, 2015.

(51) Int. Cl.
*A61K 39/00* (2006.01)
*A61K 39/395* (2006.01)
*A61K 45/06* (2006.01)
*C07K 16/28* (2006.01)
*G01N 33/574* (2006.01)

(52) U.S. Cl.
CPC .... *C07K 16/2866* (2013.01); *A61K 39/39558* (2013.01); *A61K 45/06* (2013.01); *C07K 16/2809* (2013.01); *G01N 33/57492* (2013.01); *C07K 2317/21* (2013.01); *C07K 2317/31* (2013.01); *C07K 2317/51* (2013.01); *C07K 2317/515* (2013.01); *C07K 2317/54* (2013.01); *C07K 2317/55* (2013.01); *C07K 2317/565* (2013.01); *C07K 2317/567* (2013.01); *C07K 2317/622* (2013.01); *C07K 2317/732* (2013.01); *C07K 2317/76* (2013.01); *G01N 2333/7155* (2013.01)

(58) Field of Classification Search
CPC ............ C07K 16/2866; C07K 16/2809; C07K 2317/54; A61K 39/39558; A61K 45/06; G01N 33/57492
See application file for complete search history.

(56) References Cited

U.S. PATENT DOCUMENTS

2011/0206698 A1  8/2011  Lin et al.

FOREIGN PATENT DOCUMENTS

| EP | 2583980 | 4/2013 |
|---|---|---|
| WO | WO 2010/017468 | 2/2010 |
| WO | WO 2013/056984 | 4/2013 |
| WO | WO 2014/102430 | 7/2014 |

OTHER PUBLICATIONS

Abès, et al. "Modulation of tumor immunity by therapeutic monoclonal antibodies." *Cancer and Metastasis Reviews* 30, No. 1 (2011): 111-124.
Anderson, "Human gene therapy," *Nature* 392: 25-30 (Apr. 30, 1998).
Barata, et al. "Interleukin-7 promotes survival and cell cycle progression of T-cell acute lymphoblastic leukemia cells by down-regulating the cyclin-dependent kinase inhibitor p27kip1." *Blood* 98, No. 5 (2001): 1524-1531.
Brand, et al. "Molecular mechanisms of resistance to the EGFR monoclonal antibody cetuximab." *Cancer Biology & Therapy* 11, No. 9 (2011): 777-792.
Crystal, "Transfer of genes to humans: early lessons and obstacles to success," *Science* 270: 404-410 (1995).
Debnath, et al. "Small molecule inhibitors of CXCR4." *Theranostics* 3, No. 1 (2013): 47.
Dooms, "Interleukin-7: fuel for the autoimmune attack," *Journal of Autoimmunity* 45: 40-48 (2013).

(Continued)

*Primary Examiner* — Lei Yao
(74) *Attorney, Agent, or Firm* — Klarquist Sparkman, LLP

(57) ABSTRACT

Antibodies and antigen binding fragments that specifically bind to IL-7Rα are disclosed. Nucleic acids encoding the antibodies and antigen binding fragments, and vectors including the nucleic acid molecules are also provided. Methods for detecting a ca cancer or a cell that expresses IL-7Rα using the antibodies and antigen binding fragments are disclosed, as is the use of the antibodies and antigen binding fragments to prevent and/or treat a subject with a cancer that expresses IL-7Rα, such as acute lymphoblastic leukemia.

24 Claims, 25 Drawing Sheets
Specification includes a Sequence Listing.

(56) References Cited

OTHER PUBLICATIONS

Eck et al. "Gene-based therapy," *Goodman & Gilman's The Pharmacological Basis of Therapeutics* (1996), 9th Edition, Chapter 5, pp. 77-101, McGraw-Hill, NY.
Garrett, et al. "Resistance to HER2-directed antibodies and tyrosine kinase inhibitors: mechanisms and clinical implications." *Cancer Biology & Therapy* 11, No. 9 (2011): 793-800.
Hixon, et al., "New Anti-IL-7Rα Monoclonal Antibodies Show Efficacy Against T Cell Acute Lymphoblastic Leukemia in Pre-Clinical Models," *Leukemia*: 1-32; Epub Date: (Aug. 22, 2019).
Hollevoet and Declerck, "State of play and clinical prospects of antibody gene transfer," *Journal of Translational Medicine* 15:131, 19 pages (2017).
Hummel, et al. "Inhibitors of CXC chemokine receptor type 4: putative therapeutic approaches in inflammatory diseases." *Current Opinion in Hematology* 21, No. 1 (2014): 29-36.
Juengst, "What next for human gene therapy?," *British Medical Journal* 326: 1410-1411 (2003).
Kuhne, et al. "BMS-936564/MDX-1338: A Fully Human Anti-CXCR4 Antibody Induces Apoptosis In Vitro and Shows Antitumor Activity In Vivo in Hematologic Malignancies." *Clinical Cancer Research* 19, No. 2 (2013): 357-366.
Liu, et al. "Effectiveness of AMD3100 in treatment of leukemia and solid tumors: from original discovery to use in current clinical practice." *Experimental Hematology & Oncology* 5, No. 1 (2015): 19.
Maude, et al. "CD19-targeted chimeric antigen receptor T-cell therapy for acute lymphoblastic leukemia." *Blood* 125, No. 26 (2015): 4017-4023.
Mazzucchelli, et al. "The human IL-7 receptor gene: deletions, polymorphisms and mutations." *In Seminars in Immunology*, vol. 24, No. 3, pp. 225-230. Academic Press, 2012.
Passaro, et al. "CXCR4 is required for leukemia-initiating cell activity in T cell acute lymphoblastic leukemia." *Cancer Cell* 27, No. 6 (2015): 769-779.
Penaranda, et al. "IL-7 receptor blockade reverses autoimmune diabetes by promoting inhibition of effector/memory T cells." *Proceedings of the National Academy of Sciences* 109, No. 31 (2012): 12668-12673.
Ribeiro, et al. "IL-7R-mediated signaling in T-cell acute lymphoblastic leukemia." *Advances in Biological Regulation* 53, No. 2 (2013): 211-222.
Ross et al., "Gene therapy in the United States: A five-year status report," *Human Gene Therapy* 7: 1781-1790 (Sep. 10, 1996).
Rubanyi, "The future of human gene therapy," *Biol. Aspects Med.* 22:113-142 (2001).
Scupoli, et al. "Thymic epithelial cells promote survival of human T-cell acute lymphoblastic leukemia blasts: the role of interleukin-7." *Haematologica* 88, No. 11 (2003): 1229-1237.
Shochat, et al. "Gain-of-function mutations in interleukin-7 receptor-α (IL7R) in childhood acute lymphoblastic leukemias." *Journal of Experimental Medicine* 208, No. 5 (2011): 901-908.
Silva, et al. "IL-7 contributes to the progression of human T-cell acute lymphoblastic leukemias." *Cancer Research* 71, No. 14 (2011): 4780-4789.
Tabarkiewicz et al. "The Role of IL-17 and Th17 Lymphocytes in Autoimmune Diseases." *Arch. Immunol. Ther. Exp.* 63 (2015): 435-449.
Touw, et al. "Interleukin-7 is a growth factor of precursor B and T acute lymphoblastic leukemia." *Blood* 75, No. 11 (1990): 2097-2101.
Van Vlierberghe, et al. "The molecular basis of T cell acute lymphoblastic leukemia." *The Journal of Clinical Investigation* 122, No. 10 (2012): 3398-3406.
Verma and Somia, "Gene therapy promises, problems and prospects," *Nature* 389: 239 (Sep. 1997).
Wilson, et al. "An Fcγ receptor-dependent mechanism drives antibody-mediated target-receptor signaling in cancer cells." *Cancer Cell* 19, No. 1 (2011): 101-113.
Zenatti, et al. "Oncogenic IL7R gain-of-function mutations in childhood T-cell acute lymphoblastic leukemia." *Nature Genetics* 43, No. 10 (2011): 932.
Zhang, et al. "The genetic basis of early T-cell precursor acute lymphoblastic leukaemia." *Nature* 481, No. 7380 (2012): 157.
Zhu et al. "IL-17/IL-17 receptor system in autoimmune disease: mechanisms and therapeutic potential." *Clinical Science* 122 (2012): 487-511.

2B8 and 4A10 scFv bind different IL-7Rα epitopes determined using SPR

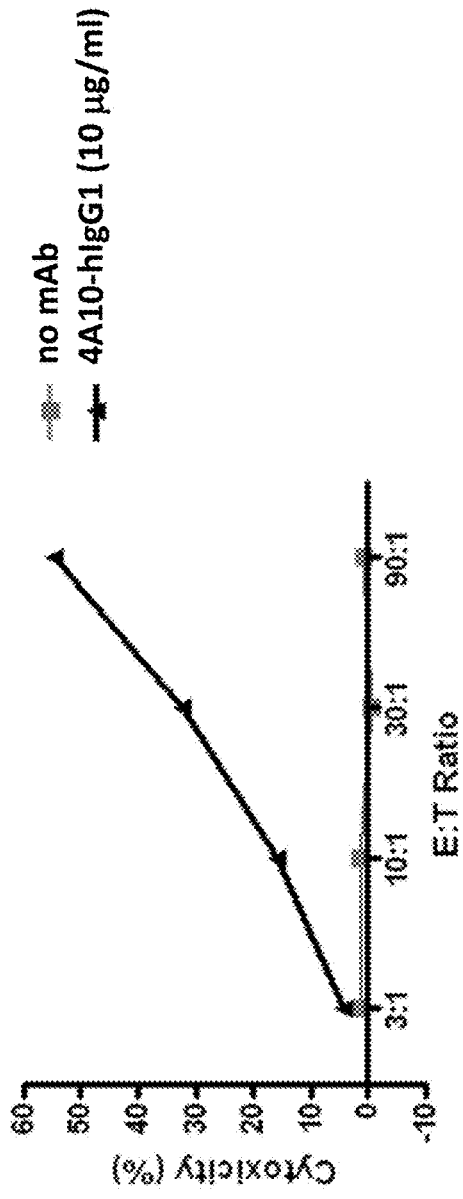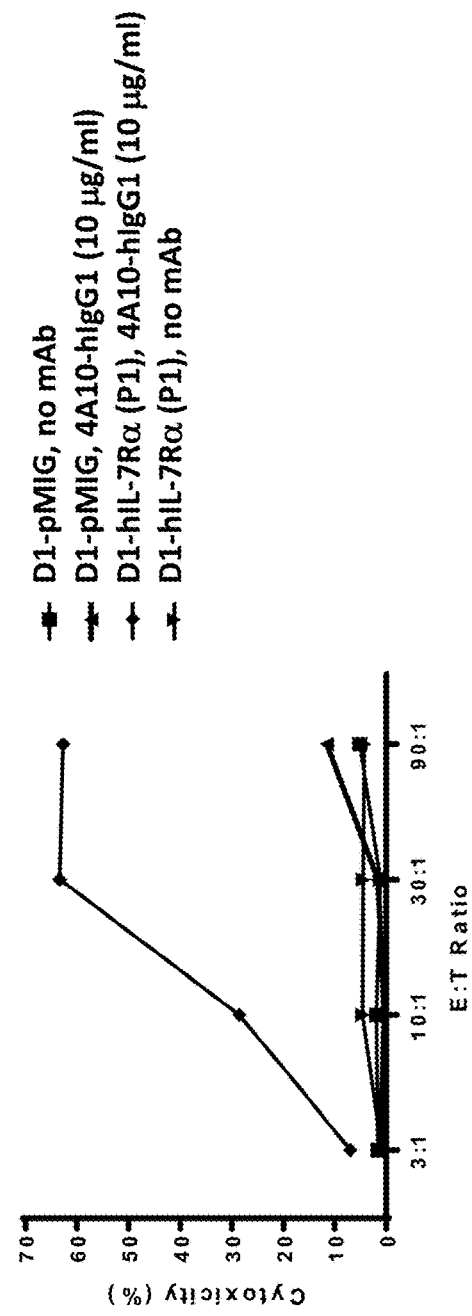
FIG. 8
FIG. 9

4A10-hIgG1 chimera mediates NK-cell killing of T-ALL cells expressing mutant IL-7Rα

4A10-hIgG1 chimera mediates NK-cell killing of normal human T cells

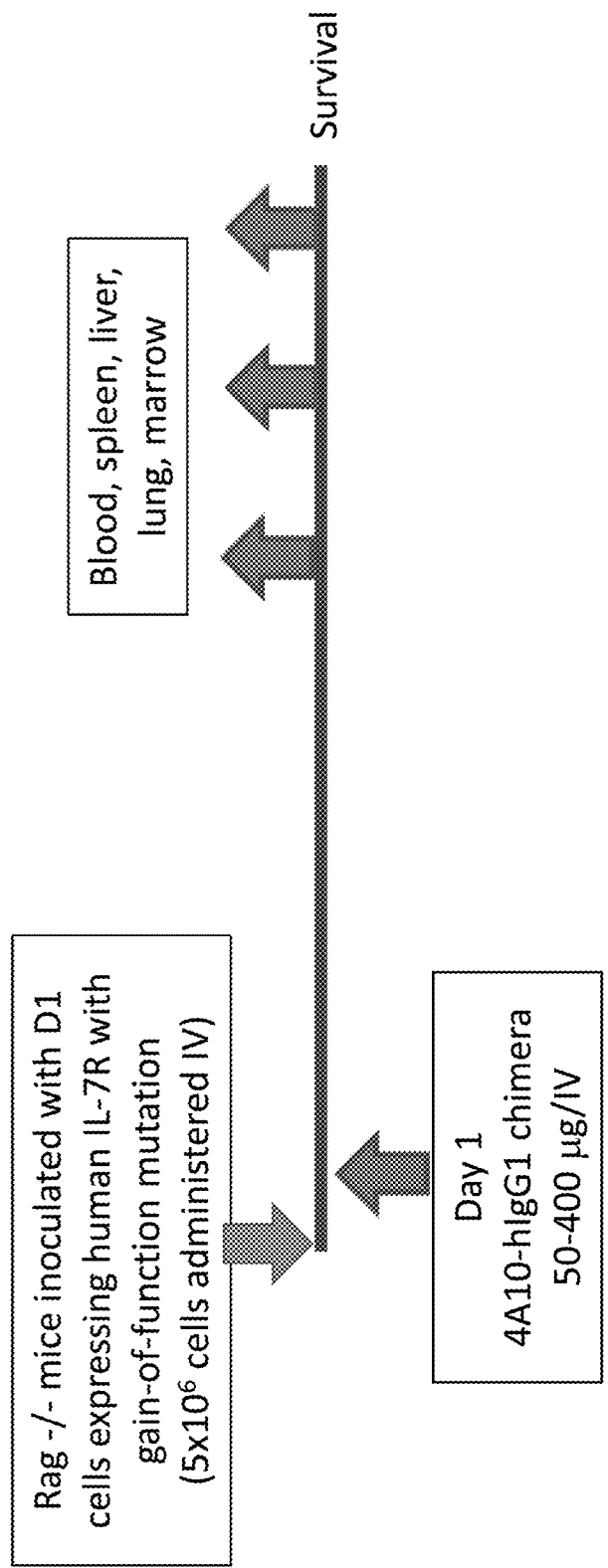

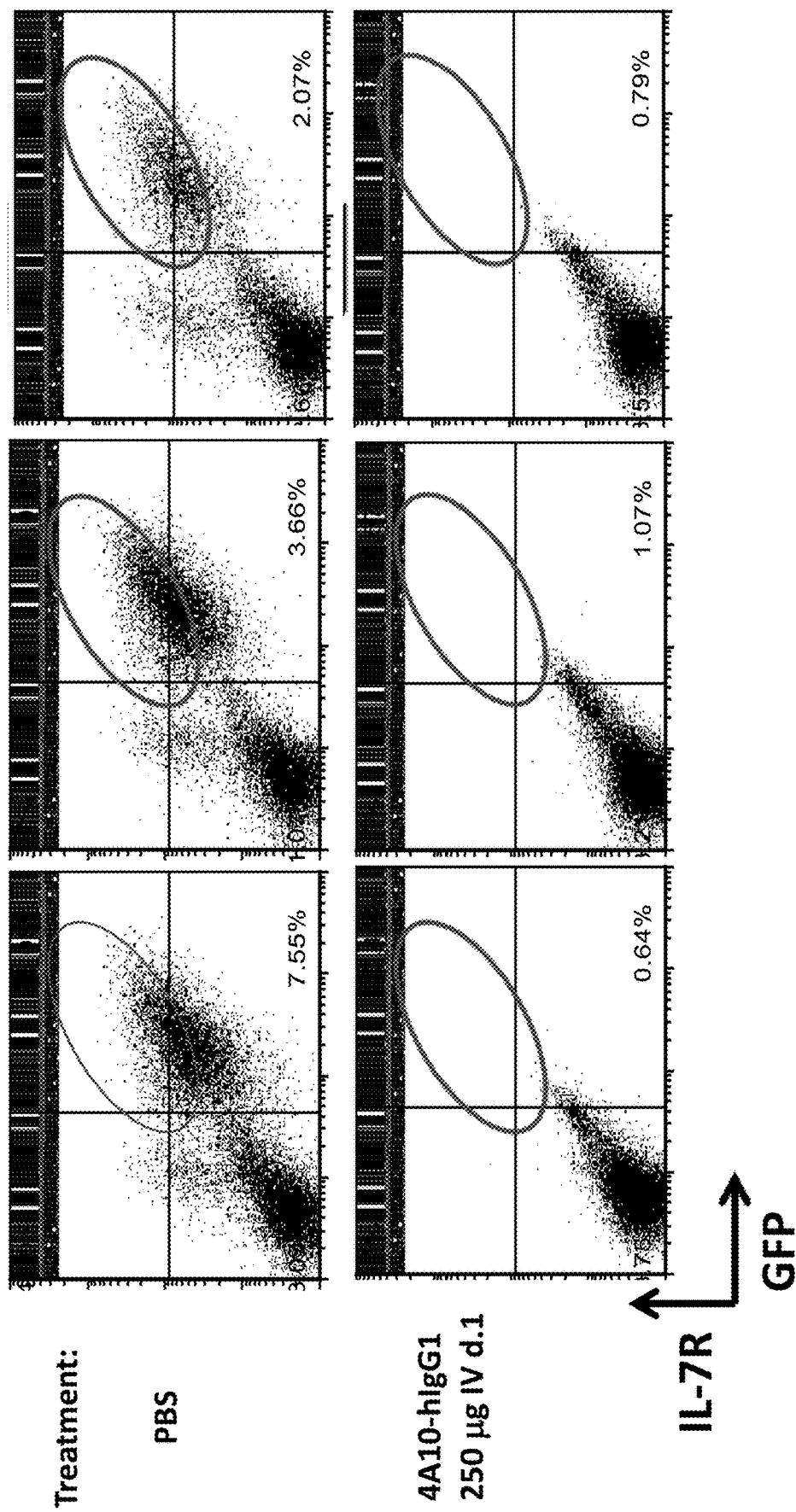
FIG. 12B Spleen assayed day 15

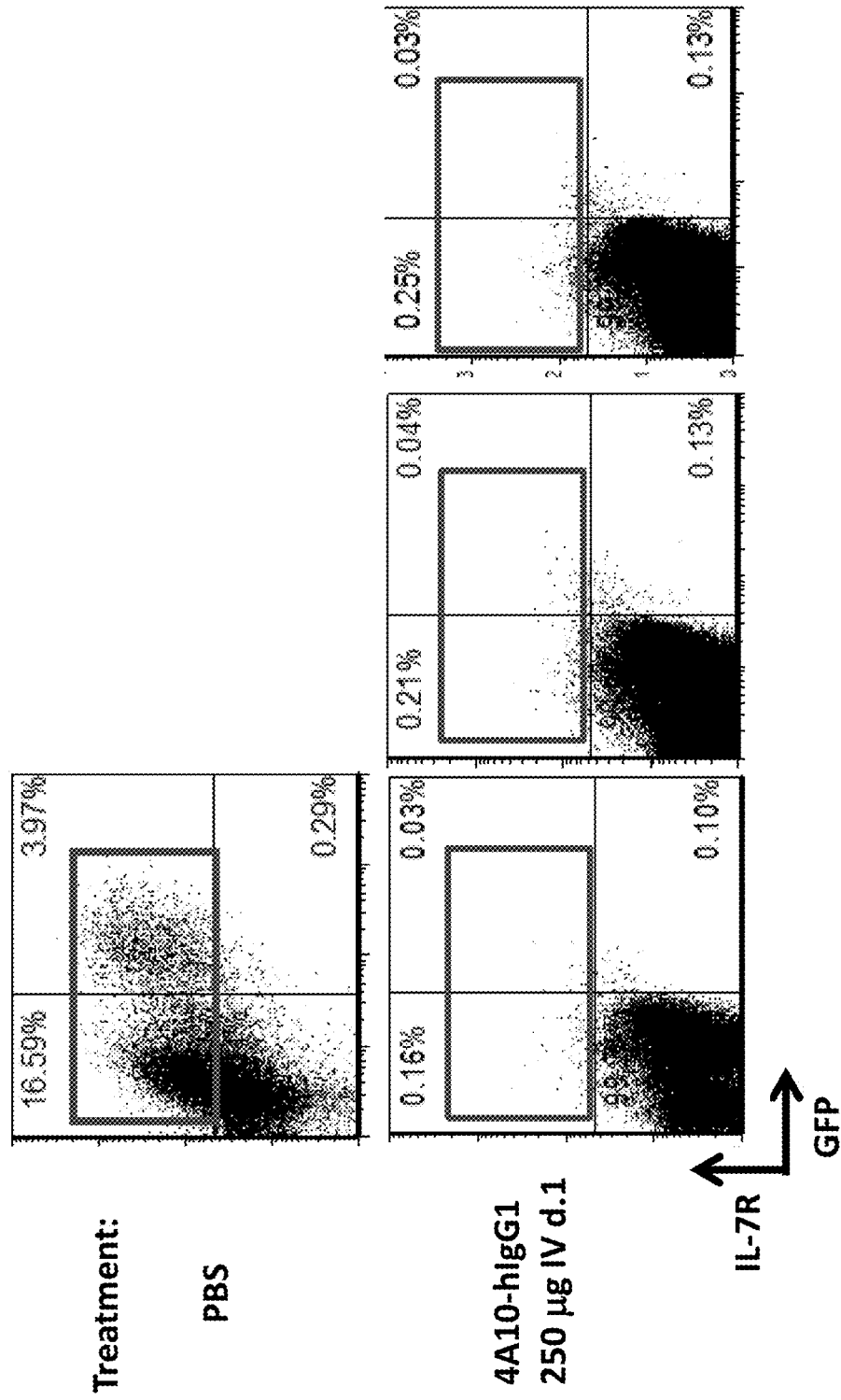

*Spleen* and *Liver* assayed on d.19

4A10-hIgG1 chimera increases survival of Rag1-/- mice inoculated with D1 cells expressing human IL-7Rα with P1 gain-of-function mutation The 4A10-hIgG1 chimera reduces proliferation of T-ALL cells expressing WT IL-7Rα in an *in vivo* model of T-ALL

*Spleen assayed d.33*

Blood assayed d.33

FIG. 14B
Anti-IL-7R reduces human T-ALL xenograft cells in blood of NOD.SCID mice
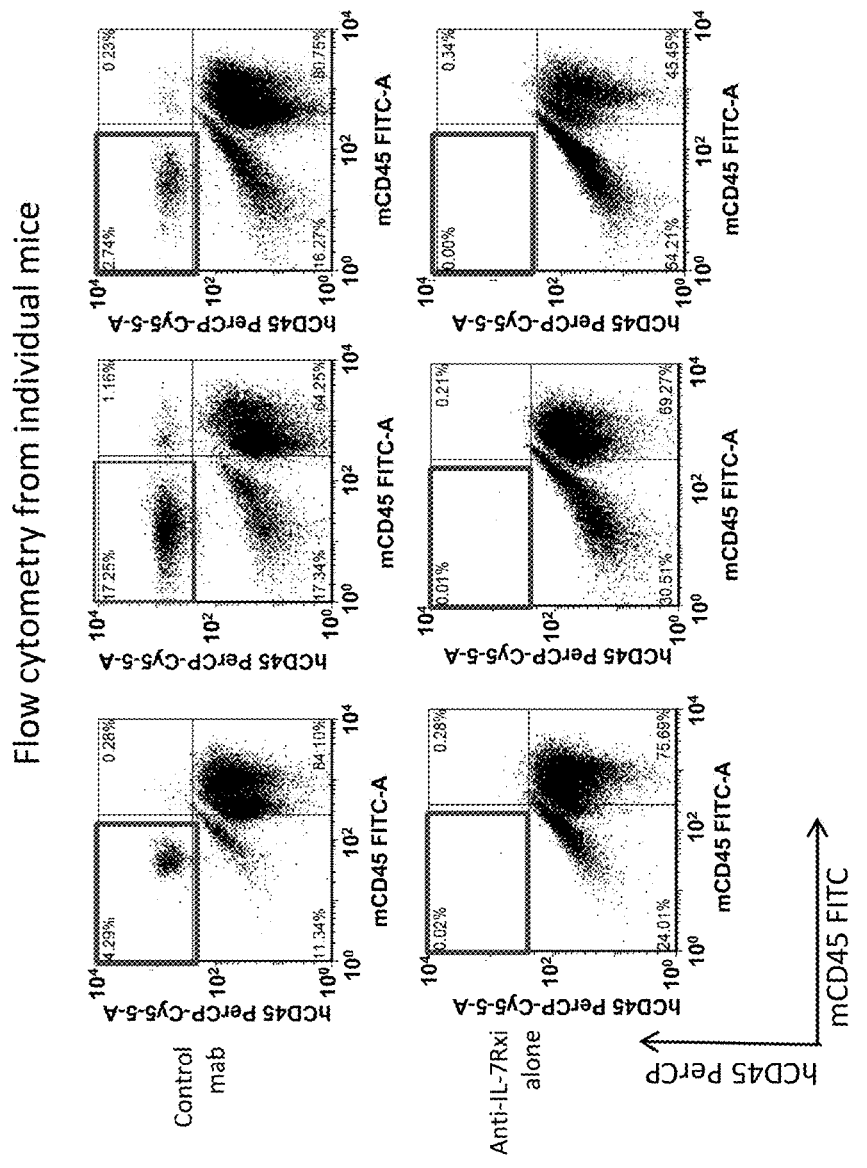
Flow cytometry from individual mice
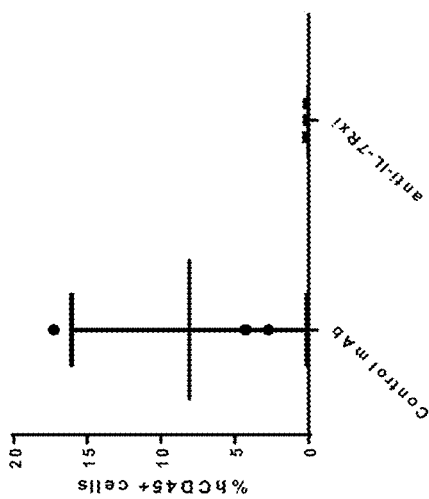
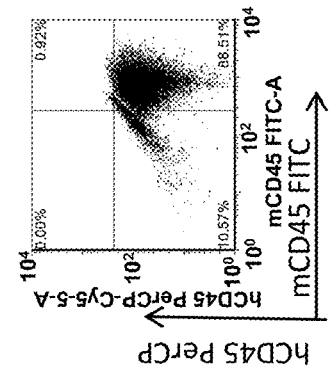

Anti-IL-7R reduces human T-ALL xenograft cells in liver of NOD.SCID mice.

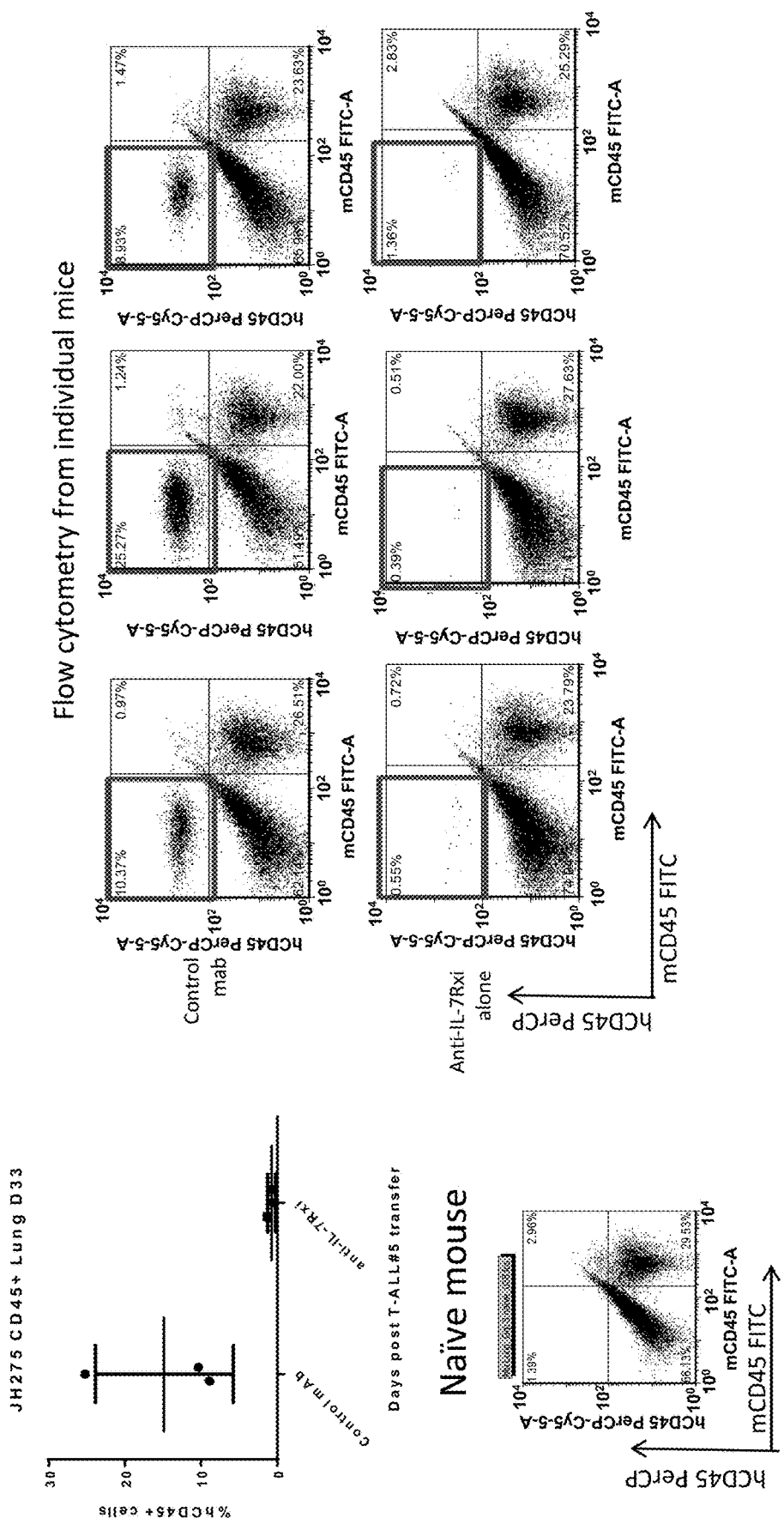

Anti-IL-7R reduces human T-ALL xenograft cells in bone marrow of NOD.SCID mice

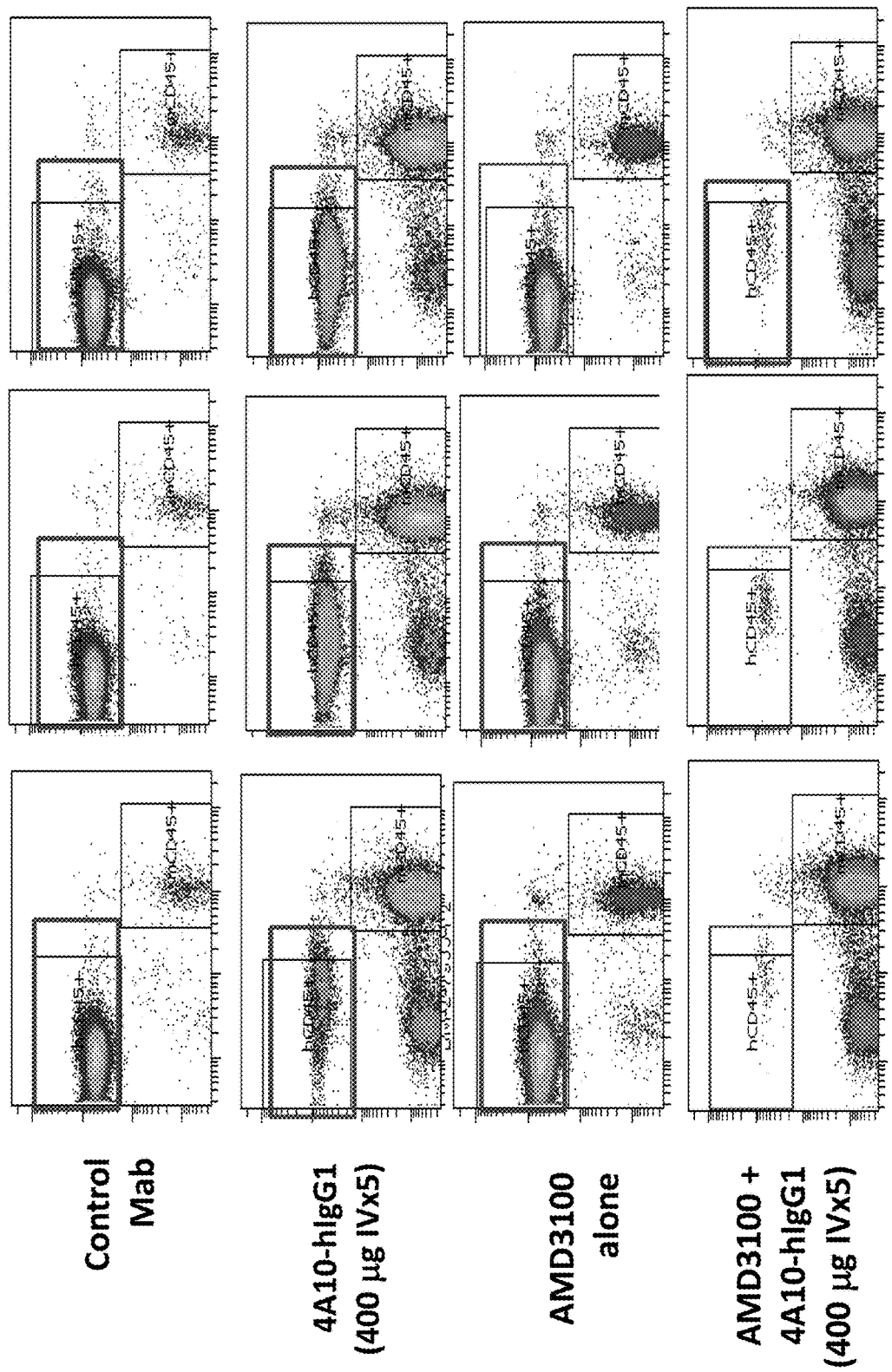

IL-7R-ALPHA SPECIFIC ANTIBODIES FOR TREATING ACUTE LYMPHOBLASTIC LEUKEMIA

CROSS REFERENCE TO RELATED APPLICATIONS

This is a continuation of U.S. patent application Ser. No. 16/459,396, filed Jul. 1, 2019, which is a continuation of U.S. patent application Ser. No. 15/760,193, filed Mar. 14, 2018, issued as U.S. Pat. No. 10,392,441, which is the U.S. national stage of International Application No. PCT/US2016/055957, filed Oct. 7, 2016, which claims the benefit of U.S. Provisional Application No. 62/238,612, filed Oct. 7, 2015. The prior applications are all incorporated by reference herein in their entirety.

FIELD OF THE DISCLOSURE

This relates to monoclonal antibodies and antigen binding fragments that specifically bind to the α chain of the interleukin 7 receptor (IL-7Rα) and their use, for example, in methods of treating a subject with acute lymphoblastic leukemia (ALL), such as T cell ALL (T-ALL).

BACKGROUND

Acute lymphoblastic leukemia (ALL) is the most common cancer in children (with approximately 3250 new cases per year in the United States). Typically, ALL is caused by over-proliferation of immature T cells (T-ALL) or immature B cells (B-ALL). Although treatment for ALL has improved dramatically in recent decades, about 20% of ALL cases are not cured. Accordingly, ALL remains a leading cause of death in children. Further, current therapies for pediatric ALL in growing children is extremely toxic, for example causing cognitive impairment due to the toxicity of chemotherapy on the developing brain. ALL can also occur in adults, and adult ALL has a far less favorable prognosis than pediatric ALL. Thus, there exists a need for new therapies for ALL, particularly for targeted therapies that have reduced cytotoxicity compared to standard chemotherapeutic regimens.

SUMMARY

Isolated monoclonal antibodies and antigen binding fragments that specifically bind to the extracellular domain of IL-7Rα are provided herein. The disclosed antibodies and antigen binding fragments are useful, for example, for treating or preventing ALL (such as T-ALL) in a subject. In some embodiments, the antibody or antigen binding fragment specifically binds to an IL-7Rα extracellular domain and comprises a heavy chain variable region ($V_H$) comprising a HCDR1, a HCDR2, and a HCDR3 of the $V_H$ set forth as SEQ ID NO: 1 (4A10 $V_H$) and/or a light chain variable region ($V_L$) comprising a LCDR1, a LCDR2, and a LCDR3 of the $V_L$ set forth as SEQ ID NO: 2 (4A10 $V_L$). In additional embodiments, the antibody or antigen binding fragment comprises a $V_H$ comprising a HCDR1, a HCDR2, and a HCDR3 of the $V_H$ set forth as SEQ ID NO: 3 (2B8 $V_H$) and/or a $V_L$ comprising a LCDR1, a LCDR2, and a LCDR3 of the $V_L$ set forth as SEQ ID NO: 4 (2B8 $V_H$). In several embodiments, the disclosed antibodies and antigen binding fragments can specifically bind to the IL-7Rα extracellular domain expressed on a cell surface.

The disclosed 4A10 and 2B8 antibodies are non-naturally occurring antibodies that were isolated from a laboratory screen of mouse hybridoma cell lines. Chimeric forms of the 4A10 and 2B8 antibodies are provided, for example, that include the heavy and light chain variable regions of the 4A10 or 2B8 antibody and human IgG (such as human IgG1) constant regions. In several embodiments, the disclosed antibodies and antigen binding fragments (for example chimeric forms of the disclosed antibodies or antigen binding fragments that include human IgG1 constant regions) can mediate antibody-dependent cell cytotoxicity (ADCC) against cells with cell-surface expression of IL-7Rα.

Also disclosed are compositions including the antibodies and antigen binding fragments, nucleic acids encoding the antibodies and antigen binding fragments, expression vectors comprising the nucleic acids, and isolated host cells that comprise the nucleic acids.

The disclosed antibodies potently reduce proliferation of cancer cells in an accepted in vivo model of ALL. Accordingly, a method is disclosed for treating or inhibiting ALL (such as T-ALL) in a subject. The methods include administering a therapeutically effective amount of one or more of the disclosed antibodies, antigen binding fragments, nucleic acid molecules, vectors, or compositions, to the subject, for example to a subject at risk of or having an IL-7Rα-positive cancer, such as ALL, for example T-ALL or B-ALL. In some embodiments, the method comprises administration of a therapeutically effective amount of a combination therapy including administration of one or more of the disclosed IL-7Rα-specific antibodies, antigen binding fragments, nucleic acid molecules, vectors, or compositions in combination with administration of an additional agent, such as a CXCR4 antagonist (for example, AMD3100) to the subject, for example to a subject at risk of or having an IL-7Rα-positive cancer, such as ALL, for example T-ALL or B-ALL.

The antibodies, antigen binding fragments, nucleic acid molecules, vectors, and compositions disclosed herein can be used for a variety of additional purposes, such as for detecting IL-7Rα expression on the surface of a cell, diagnosing an IL-7Rα-positive cancer (such as T-ALL) in a subject, identifying a subject with ALL (such as T-ALL) that will respond to therapy with a disclosed IL-7Rα antibody, or detecting IL-7Rα in a sample.

In additional embodiments, a method is provided for treating or preventing an autoimmune disease in a subject, the method comprising administering a therapeutically effective amount of a disclosed IL-7Rα specific antibody or antigen binding fragment to the subject. Non-limiting examples of autoimmune diseases that can be treated with a disclosed IL-7Rα specific antibody or antigen binding fragment include rheumatoid arthritis, type I diabetes, atopic dermatitis, multiple sclerosis, primary biliary cirrhosis, inflammatory bowel disease, sarcoidosis, or graft versus host disease.

The foregoing and other features and advantages of this disclosure will become more apparent from the following detailed description of several embodiments which proceeds with reference to the accompanying figures.

BRIEF DESCRIPTION OF THE FIGURES

FIG. 8 illustrates that the 4A10-hIgG1 chimera mediates Natural Killer (NK)-cell ADCC against BaF3 cells expressing human IL-7Rα. BaF3 cells are a murine B cell line that does not express human IL-7Rα and is not bound by the 4A10 antibody. The cells were incubated with NK cells isolated from human blood at the indicated effector:target (E:T) ratios and with the 4A10-hIgG1 chimera (10 μg/ml). Release of lactate dehydrogenase (LDH) was measured to evaluate cell lysis (cytotoxicity).

FIG. 9 illustrates that the 4A10-hIgG1 chimera mediates NK-cell ADCC against D1 cells expressing human mutant IL-7Rα from a T-ALL patient. D1 cells are a murine T cell line that does not express human IL-7Rα and is not bound by the 4A10 antibody. The cells were incubated with NK cells isolated from human blood at the indicated E:T ratios and with the 4A10-hIgG1 chimera (10 μg/ml). Release of LDH was measured to evaluate cell lysis (cytotoxicity).

FIGS. 12A-12F illustrate that the 4A10-hIgG1 chimera reduces proliferation of D1 cells expressing human IL-7Rα with a gain-of function mutation in an in vivo assay, and promotes survival of mice inoculated with such cells. D1 cells transfected with mutant (P1) IL-7Rα and GFP were injected intravenously into Rag1$^{-/-}$ mice. The following day, 4A10-hIgG1 chimera (50-400 μg) or PBS (control) was administered intravenously to the mice. Blood and tissue were sampled at various time points post-inoculation, and the overall survival of the mice was also evaluated (FIGS. 12B-12F).

FIGS. 14A-14F illustrate that administration of the 4A10-hIgG1 chimera reduces proliferation of human T-ALL cells expressing WT IL-7Rα in an in vivo assay using NOD.SCID mice which have NK cells but lack T and B cells. (14A) Human T-ALL cells isolated from a patient and expressing WT IL-7Rα were injected intravenously into NOD.SCID mice. 4A10-hIgG1 chimera (250 μg) or PBS (control) were administered intravenously at weekly intervals to the mice totaling five injections. Blood and tissue were sampled at various time points post-inoculation and evaluated by human CD45 staining to assay human T-ALL cell proliferation in blood (FIG. 14B), liver (FIG. 14C), lung (FIG. 14D), and bone marrow (FIG. 14E). Mouse survival is show in FIG. 14F.

FIG. 16 shows a set of graphs illustrating the synergy of combination therapy including the CXCR4 antagonist AMD3100 and the 4A10-hIgG1 chimera against T-ALL in bone marrow of NSG mice which lack NK cells.

SEQUENCE LISTING

Figure 1:
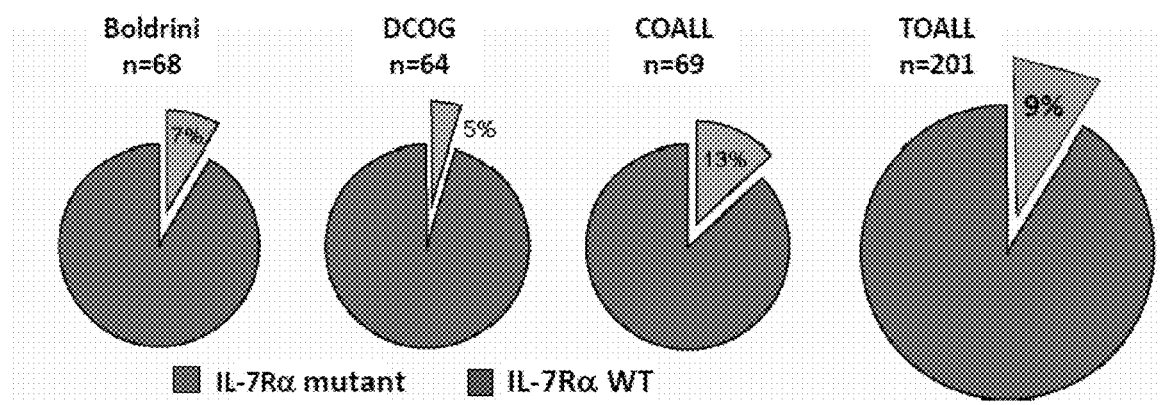
FIG. 1 is a set of graphs illustrating prior findings that mutations in IL-7Rα are found in pediatric T-ALL patients. Three patient cohorts (the Boldrini, DCOG, and COALL patient cohorts) and the total are shown (see Zenatti et al., Nat. Genetics, 43:932-939, 2011).

The nucleic and amino acid sequences are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file in the form of the file named "Sequence.txt" (~51.5 kb), which was created on Aug. 2, 2021 which is incorporated by reference herein. In the accompanying sequence listing:

Bold highlighting in SEQ ID NOs: 1-4 indicates kabat CDR sequences. Bold highlighting in SEQ ID NOs: 17-24 indicates constant region sequences.

SEQ ID NO: 1 is the amino acid sequence of the $V_H$ of the 4A10 mAb.
QVQLQQPGAELVMPGASVKLSCKASGYTFTSYWMHWVKQRPGEGLEWIGEIDPSDSYTNDNQKFKGKATL

TVDKSSSTAYMQLSSLTSEDSAVYYCARRLYSNSYYYAMDYWGQGTSVTVSS

SEQ ID NO: 2 is the amino acid sequence of the $V_L$ of the 4A10 mAb.
DIQMTQSPSSLSASLGGKVTITCKASQDIKKYIAWYQHKPGKGPRLLIHYTSTLQPGIPSRFSGSGSGRD

YSFSISNLEPVDIATYYCLQYDNLLTFGAGTKLELK

SEQ ID NO: 3 is the amino acid sequence of the $V_H$ of the 2B8 mAb.
EVQLQQSGPELVKPGASVKMSCKASGYTFSDYYMHWVKQSHGKSLEWIGYIYPDNGGNGYNQKFKGKATL

TVDKSSSTVYMELRSLTSEDSALYYCARGTYYDGSYFDYWGQGTTLTVSS

SEQ ID NO: 4 is the amino acid sequence of the $V_L$ of the 2B8 mAb.
DIVMTQSHKFMSTLVGDRVSITCKASQDVSTTVAWYQQKPGQSPKLLIYSASYRYTGVPDRFTGSGSGTD

FTFTISSVQAEDLAVYYCQQHYSIPRTEGGGTKLEIK

SEQ ID NOs: 5-16 are amino acid sequences of the kabat CDRs of the 4A10 and 2B8 antibodies.

SEQ ID NO: 17 is the amino acid sequence of the heavy chain of the 4A10 mAb.
QVQLQQPGAELVMPGASVKLSCKASGYTFTSYWMHWVKQRPGEGLEWIGEIDPSDSYTNDNQKFKGKATL

TVDKSSSTAYMQLSSLTSEDSAVYYCARRLYSNSYYYAMDYWGQGTSVTVSSAKTTPPSVYPLAPGSAAQ

TNSMVTLGCLVKGYFPEPVTVTWNSGSLSSGVHTFPAVLQSDLYTLSSSVTVPSSTWPSQTVTCNVAHPA

SSTKVDKKIVPRDCGCKPCICTVPEVSSVFIFPPKPKDVLTITLTPKVTCVVVDISKDDPEVQFSWFVDD

VEVHTAQTKPREEQINSTFRSVSELPIMHQDWLNGKEFKCRVNSAAFPAPIEKTISKTKGRPKAPQVYTI

PPPKEQMAKDKVSLTCMITNFFPEDITVEWQWNGQPAENYKNTQPIMDTDGSYFVYSKLNVQKSNWEAGN

TFTCSVLHEGLHNHHTEKSLSHSPGK

SEQ ID NO: 18 is the amino acid sequence of the light chain of the 4A10 mAb.
DIQMTQSPSSLSASLGGKVTITCKASQDIKKYIAWYQHKPGKGPRLLIHYTSTLQPGIPSRFSGSGSGRD

YSFSISNLEPVDIATYYCLQYDNLLTFGAGTKLELKRADAAPTVSIFPPSSEQLTSGGASVVCFLNNEYP

RDINVKWKIDGSERQNGVLNSWTDQDSKDSTYNMSSTLTLTKDEYERHNSYTCEATHKTSTSPIVKSFNR

NEC

SEQ ID NO: 19 is the amino acid sequence of the heavy chain of the 2B8 mAb.
EVQLQQSGPELVKPGASVKMSCKASGYTESDYYMHWVKQSHGKSLEWIGYTYPDNGGNGYNQKFKGKATL

TVDKSSSTVYMELRSLTSEDSALYYCARGTYYDGSYFDYWGQGTTLTVSSAKTTPPSVYPLAPGSAAQTN

SMVTLGCLVKGYFPEPVTVTWNSGSLSSGVHTFPAVLQSDLYTLSSSVTVPSSTWPSQTVTCNVAHPASS

TKVDKKIVPRDCGCKPCICTVPEVSSVFIFPPKPKDVLTITLTPKVTCVVVDISKDDPEVQFSWFVDDVE

-continued

VHTAQTKPREEQINSTFRSVSELPIMHQDWLNGKEFKCRVNSAAFPAPIEKTISKTKGRPKAPQVYTIPP

PKEQMAKDKVSLTCMITNFFPEDITVEWQWNGQPAENYKNTQPIMDTDGSYFVYSKLNVQKSNWEAGNTF

TCSVLHEGLHNHHTEKSLSHSPGK

SEQ ID NO: 20 is the amino acid sequence of the light chain of the 2B8 mAb.
DIVMTQSHKFMSTLVGDRVSITCKASQDVSTTVAWYQQKPGQSPKLLIYSASYRYTGVPDRFTGSGSGTD

FTFTISSVQAEDLAVYYCQQHYSIPRTEGGGTKLEIKRADAAPTVSIFPPSSEQLTSGGASVVCFLNNFY

PRDINVKWKIDGSERQNGVLNSWTDQDSKDSTYSMSSTLTLTKDEYERHNSYTCEATHKTSTSPIVKSFT

RNEC

SEQ ID NO: 21 is the amino acid sequence of a chimeric heavy chain including the 4A10 V$_H$ and a human IgG1 constant region.
QVQLQQPGAELVMPGASVKLSCKASGYTFTSYWMHWVKQRPGEGLEWIGEIDPSDSYTNDNQKFKGKATL

TVDKSSSTAYMQLSSLTSEDSAVYYCARRLYSNSYYYAMDYWGQGTSVTVSSASTKGPSVFPLAPSSKST

SGGTAALGCLVKDYFPEPVTVSWNSGALTSGVHTFPAVLQSSGLYSLSSVVTVPSSSLGTQTYICNVNHK

PSNTKVDKKVEPKSCDKTHTCPPCPAPELLGGPSVFLFPPKPKDTLMISRTPEVTCVVVDVSHEDPEVKF

NWYVDGVEVHNAKTKPREEQYNSTYRVVSVLTVLHQDWLNGKEYKCKVSNKALPAPIEKTISKAKGQPRE

PQVYTLPPSRDELTKNQVSLTCLVKGFYPSDIAVEWESNGQPENNYKTTPPVLDSDGSFFLYSKLTVDKS

RWQQGNVFSCSVMHEALHNHYTQKSLSLSPGK

SEQ ID NO: 22 is the amino acid sequence of a chimeric light chain including the 4A10 V$_L$ and a human IgG1 constant region.
DIQMTQSPSSLSASLGGKVTITCKASQDIKKYIAWYQHKPGKGPRLLIHYTSTLQPGIPSRFSGSGSGRD

YSFSISNLEPVDIATYYCLQYDNLLTFGAGTKLELKRTVAAPSVFIFPPSDEQLKSGTASVVCLLNNFYP

REAKVQWKVDNALQSGNSQESVTEQDSKDSTYSLSSTLTLSKADYEKHKVYACEVTHQGLSSPVTKSFNR

GEC

SEQ ID NO: 23 is the amino acid sequence of a chimeric heavy chain including the 2B8 V$_H$ and a human IgG1 constant region.
EVQLQQSGPELVKPGASVKMSCKASGYTFSDYYMHWVKQSHGKSLEWIGYIYPDNGGNGYNQKFKGKATL

TVDKSSSTVYMELRSLTSEDSALYYCARGTYYDGSYFDYWGQGTTLTVSSASTKGPSVFPLAPSSKSTSG

GTAALGCLVKDYFPEPVTVSWNSGALTSGVHTFPAVLQSSGLYSLSSVVTVPSSSLGTQTYICNVNHKPS

NTKVDKKVEPKSCDKTHTCPPCPAPELLGGPSVFLFPPKPKDTLMISRTPEVTCVVVDVSHEDPEVKFNW

YVDGVEVHNAKTKPREEQYNSTYRVVSVLTVLHQDWLNGKEYKCKVSNKALPAPIEKTISKAKGQPREPQ

VYTLPPSRDELTKNQVSLTCLVKGFYPSDIAVEWESNGQPENNYKTTPPVLDSDGSFFLYSKLTVDKSRW

QQGNVFSCSVMHEALHNHYTQKSLSLSPGK

SEQ ID NO: 24 is the amino acid sequence of a chimeric light chain including the 2B8 V$_L$ and a human IgG1 constant region.
DIVMTQSHKFMSTLVGDRVSITCKASQDVSTTVAWYQQKPGQSPKLLIYSASYRYTGVPDRFTGSGSGTD

FTFTISSVQAEDLAVYYCQQHYSIPRTFGGGTKLEIKRTVAAPSVFIFPPSDEQLKSGTASVVCLLNNFY

PREAKVQWKVDNALQSGNSQESVTEQDSKDSTYSLSSTLTLSKADYEKHKVYACEVTHQGLSSPVTKSFN

RGEC

SEQ ID NO: 25 is an exemplary nucleic acid sequence encoding the V$_H$ of the 4A10 mAb.
caggtccaactgcagcagcctggggctgagcttgtgatgcctggggcttcagtgaagctgtcctgcaagg cttctggctacaccttcaccagctactggatgcactgggtgaagcagaggcctggagaaggccttgagtg gatcggagagattgatccttctgatagttatactaacgacaatcaaaagttcaagggcaaggccacattg actgtagacaaatcctccagcacagcctacatgcagctcagcagcctgacatctgaggactctgcggtct attactgtgcaagaaggctctatagtaactcttattactatgctatggactactggggtcaaggaacctc agtcaccgtctcctca -continued SEQ ID NO: 26 is an exemplary nucleic acid sequence encoding the V$_L$ of the 4A10 mAb.
gacatccagatgacacagtctccatcctcactgtctgcatctctgggaggcaaagtcaccatcacttgca aggcaagccaagacattaagaagtatatagcttggtaccaacacaagcctggaaaaggtcctaggctgct catacattacacatctacattacagccaggcatcccatcaaggttcagtggaagtgggtctgggagagat tattccttcagcatcagcaacctggagcctgtggatattgcaacttattattgtctgcagtatgataatc ttctcacattcggtgctgggaccaagctggagctgaaa SEQ ID NO: 27 is an exemplary nucleic acid sequence encoding the V$_H$ of the 2B8 mAb.
gaggtccagctgcaacagtctggacctgagttggtgaagcctggggcttcagtgaagatgtcctgcaagg cttctggctacacattcagtgactactacatgcactgggtgaagcagagccatggaaagagccttgagtg gattggatatatttatcctgacaatggtggtaatggctacaaccagaagttcaagggcaaggccacattg actgtagacaagtcctccagcacagtctacatggagctccgcagcctgacatctgaggactctgcactct attactgtgcaagagggacctactatgatggttcctactttgactactggggccaaggcaccactctcac agtctcctca SEQ ID NO: 28 is an exemplary nucleic acid sequence encoding the V$_L$ of the 2B8 mAb.
gacattgtgatgacccagtctcacaaattcatgtccacattagtaggagacagggtcagcatcacctgca aggccagtcaggatgtgagtactactgtagcctggtatcaacagaaaccaggacaatctcctaaactact gatttactcggcatcctaccggtacactggagtccctgatcgcttcactggcagtggatctgggacggat ttcactttcaccatcagcagtgtgcaggctgaagacctggcagtttattactgtcaacaacattatagta ttcctcggacgttcggtggaggcaccaagctggaaatcaaa SEQ ID NO: 29 is an exemplary nucleic acid sequence encoding the heavy chain of the 4A10 mAb.
caggtccaactgcagcagcctggggctgagcttgtgatgcctggggcttcagtgaagctgtcctgcaagg cttctggctacaccttcaccagctactggatgcactgggtgaagcagaggcctggagaaggccttgagtg gatcggagagattgatccttctgatagttatactaacgacaatcaaaagttcaagggcaaggccacattg actgtagacaaatcctccagcacagcctacatgcagctcagcagcctgacatctgaggactctgcggtct attactgtgcaagaaggctctatagtaactcttattactatgctatggactactggggtcaaggaacctc agtcaccgtctcctcagccaaaacgacacccccatctgtctatccactggcccctggatctgctgcccaa actaactccatggtgacctgggatgcctggtcaagggctatttccctgagccagtgacagtgacctgga actctggatccctgtccagcggtgtgcacaccttcccagctgtcctgcagtctgacctctacactctgag cagctcagtgactgtcccctccagcacctgggcccagccagaccgtcacctgcaacgttgcccacccggcc agcagcaccaaggtggacaagaaaattgtgcccagggattgtggttgtaagccttgcatatgtacagtcc cagaagtatcatctgtcttcatcttccccccaaagcccaaggatgtgctcaccattactctgactcctaa ggtcacgtgtgttgtggtagacatcagcaaggatgatcccgaggtccagttcagctggtttgtagatgat gtggaggtgcacacagctcagacgaaaccccgggaggagcagatcaacagcactttccgttcagtcagtg aacttcccatcatgcaccaggactggctcaatggcaaggagttcaaatgcagggtcaacagtgcagcttt ccctgcccccatcgagaaaaccatctccaaaaccaaaggcagaccgaaggctccacaggtgtacaccatt ccacctcccaaggagcagatggccaaggataaagtcagtctgacctgcatgataacaaacttcttccctg aagacattactgtggagtggcagtggaatgggcagccagcggagaactacaagaacactcagcccatcat ggacacagatggctcttacttcgtctacagcaagctcaatgtgcagaagagcaactgggaggcaggaaat actttcacctgctctgtgttacatgagggcctgcacaaccaccatactgagaagagcctctcccactctc ctggtaaa -continued SEQ ID NO: 30 is an exemplary nucleic acid sequence encoding the light chain of the 4A10 mAb.
gacatccagatgacacagtctccatcctcactgtctgcatctctgggaggcaaagtcaccatcacttgca aggcaagccaagacattaagaagtatatagcttggtaccaacacaagcctggaaaaggtcctaggctgct catacattacacatctacattacagccaggcatcccatcaaggttcagtggaagtgggtctgggagagat tattccttcagcatcagcaacctggagcctgtggatattgcaacttattattgtctgcagtatgataatc ttctcacattcggtgctgggaccaagctggagctgaaacgggctgatgctgcaccaactgtatccatctt cccaccatccagtgagcagttaacatctggaggtgcctcagtcgtgtgcttcttgaacaacttctacccc agagacatcaatgtcaagtggaagattgatggcagtgaacgacaaaatggtgtcctgaacagttggactg atcaggacagcaaagacagcacctacaacatgagcagcaccctcacattgaccaaggacgagtatgaacg acataacagctatacctgtgaggccactcacaagacatcaacttcacccatcgtcaagagcttcaacagg aatgagtgt SEQ ID NO: 31 is an exemplary nucleic acid sequence encoding the heavy chain of the 2B8 mAb.
gaggtccagctgcaacagtctggacctgagttggtgaagcctggggcttcagtgaagatgtcctgcaagg cttctggctacacattcagtgactactacatgcactgggtgaagcagagccatggaaagagccttgagtg gattggatatatttatcctgacaatggtggtaatggctacaaccagaagttcaagggcaaggccacattg actgtagacaagtcctccagcacagtctacatggagctccgcagcctgacatctgaggactctgcactct attactgtgcaagagggacctactatgatggttcctactttgactactggggccaaggcaccactctcac agtctcctcagccaaaacgacaccccatctgtctatccactggcccctggatctgctgcccaaactaac tccatggtgaccctgggatgcctggtcaagggctatttccctgagccagtgacagtgacctggaactctg gatccctgtccagcggtgtgcacaccttcccagctgtcctgcagtctgacctctacactctgagcagctc agtgactgtcccctccagcacctggcccagccagaccgtcacctgcaacgttgcccacccggccagcagc accaaggtggacaagaaaattgtgcccagggattgtggttgtaagccttgcatatgtacagtcccagaag tatcatctgtcttcatcttccccccaaagcccaaggatgtgctcaccattactctgactcctaaggtcac gtgtgttgtggtagacatcagcaaggatgatcccgaggtccagttcagctggtttgtagatgatgtggag gtgcacacagctcagacgaaaccccgggaggagcagatcaacagcactttccgttcagtcagtgaacttc ccatcatgcaccaggactggctcaatggcaaggagttcaaatgcagggtcaacagtgcagctttccctgc ccccatcgagaaaaccatctccaaaaccaaaggcagaccgaaggctccacaggtgtacaccattccacct cccaaggagcagatggccaaggataaagtcagtctgacctgcatgataacaaacttcttccctgaagaca ttactgtggagtggcagtggaatgggcagccagcggagaactacaagaacactcagcccatcatggacac agatggctcttacttcgtctacagcaagctcaatgtgcagaagagcaactgggaggcaggaaatactttc acctgctctgtgttacatgagggcctgcacaaccaccatactgagaagagcctctcccactctcctggta aa SEQ ID NO: 32 is an exemplary nucleic acid sequence encoding the light chain of the 2B8 mAb.
gacattgtgatgacccagtctcacaaattcatgtccacattagtaggagacagggtcagcatcacctgca aggccagtcaggatgtgagtactactgtagcctggtatcaacagaaaccaggacaatctcctaaactact gatttactcggcatcctaccggtacactggagtccctgatcgcttcactggcagtggatctgggacggat ttcactttcaccatcagcagtgtgcaggctgaagacctggcagtttattactgtcaacaacattatagta ttcctcggacgttcggtggaggcaccaagctggaaatcaaacgggctgatgctgcaccaactgtatccat cttcccaccatccagtgagcagttaacatctggaggtgcctcagtcgtgtgcttcttgaacaacttctac cccagagacatcaatgtcaagtggaagattgatggcagtgaacgacaaaatggtgtcctgaacagttgga ctgatcaggacagcaaagacagcacctacagcatgagcagcaccctcacattgaccaaggacgagtatga -continued acgacataacagctatacctgtgaggccactcacaagacatcaacttcacccatcgtcaagagcttcaac aggaatgagtgt SEQ ID NO: 33 is an exemplary nucleic acid sequence encoding a
chimeric heavy chain including the 4A10 $V_H$ and a human IgG1 constant
region.
caggtccagctgcagcagcccggagccgaactggtcatgcccggcgccagcgtgaagctgtcctgcaagg cttctggctataccttcacatcctactggatgcactgggtgaagcagagacccggagagggactggagtg gatcggcgagatcgacccatccgattcttataccaacgacaatcagaagtttaagggcaaggccaccctg acagtggataagagctcctctaccgcttatatgcagctgagctccctgacaagcgaggactccgccgtgt actattgcgctcggaggctgtatagcaactcctactattacgccatggattactggggccagggcaccag cgtgacagtgtctagcgccagcaccaagggcccttccgtgttcccactggctccctcctctaaatctacc agcggaggaacagccgctctgggatgtctggtgaaggactacttcccagagcccgtgacagtgtcttgga acagcggcgccctgacctccggcgtgcacacatttcctgctgtgctgcagagctccggcctgtattctct gtctagcgtggtgaccgtgccatcctctagcctgggcacccagacatacatctgcaacgtgaatcacaag ccatccaatacaaaggtggacaagaaggtcgagcccaagtcttgtgataagacccacacatgcccccctt gtcctgctccagagctgctgggaggaccttccgtgttcctgtttccacccaaacctaaggacaccctgat gatcagccggaccccagaggtgacatgcgtggtggtggacgtgtcccacgaggatcccgaggtgaagttt aactggtacgtcgatggcgtggaggtgcacaatgctaagaccaagcccagagaggagcagtataactcta cctaccgggtggtgagcgtgctgacagtgctgcaccaggactggctgaacggcaaggagtacaagtgcaa ggtgtctaataaggccctgcccgctcccatcgagaagaccatcagcaaggccaagggccagcctagggag ccacaggtgtatacactgcctccatctagagacgagctgaccaagaaccaggtgagcctgacatgtctgg tgaagggcttctaccccagcgatatcgccgtggagtgggagtccaatggccagcctgagaacaattataa gaccacaccccctgtgctggactccgatggctcttttctttctgtactccaagctgaccgtggataagtct aggtggcagcagggcaacgtgttcagctgttctgtgatgcacgaagctctgcataatcactacacccaga aaagcctgtccctgtcacctggtaaa SEQ ID NO: 34 is an exemplary nucleic acid sequence encoding a
chimeric light chain including the 4A10 $V_L$ and a human IgG1 constant
region.
gatattcagatgactcagtccccttcttcactgtctgccagcctgggcggcaaggtgaccatcacatgca aggcctcccaggacatcaagaagtacatcgcttggtatcagcacaagcctggcaagggcccacggctgct gatccactacacctctacactgcagccaggcatcccagccggttctccggaagcggaagcggaagggat tactccttttctatcagcaacctggagcccgtggacatcgccacctactattgcctgcagtatgataatc tgctgaccttcggcgctggcacaaagctggagctgaagagaaccgtggccgctcccagcgtgttcatctt tccccttccgacgagcagctgaagtccggcacagcttctgtggtgtgcctgctgaacaacttctaccct cgggaggccaaggtgcagtggaaggtggataacgctctgcagtccggcaattctcaggagagcgtgaccg agcaggactccaaggattctacatatagcctgagctccaccctgacactgtctaaggccgactacgagaa gcacaaggtgtatgcttgtgaagtgactcatcagggtctgtcatcacccgtgactaaatcattcaataga ggcgaatgc SEQ ID NO: 35 is an exemplary nucleic acid sequence encoding a
chimeric heavy chain including the 2B8 $V_H$ and a human IgG1 constant
region.
gaagtccagctgcagcagtctggtcctgaactggtgaagcctggcgcctccgtgaagatgtcttgcaagg ctagcggctacaccttcagcgactactatatgcactgggtgaagcagtcccacggcaagtctctggagtg gatcggctacatctatccagataacggcggcaatggctacaaccagaagtttaagggcaaggccaccctg acagtggacaagagctcctctaccgtgtatatggagctgaggagcctgacatccgaggattctgccctgt -continued

```
actattgcgctagaggcacctactatgacggctcctacttcgattattggggccagggcaccacactgac cgtgagctccgccagcacaaagggcccctccgtgtttccactggctccctcttccaagtctaccagcgga ggaacagccgctctgggatgtctggtgaaggactactttcccagagccgtgaccgtgagctggaacagcg gcgccctgacctccggcgtgcacacatttccagctgtgctgcagtcctctggcctgtactctctgagctc cgtggtgaccgtgccctctagctccctgggcacccagacatatatctgcaacgtgaatcacaagccatcc aacacaaaggtggacaagaaggtcgagcccaagtcttgtgataagacccacacatgcccccccttgtcctg ctcccgagctgctgggaggacctagcgtgttcctgtttcacccaagcctaaggacaccctgatgatcag ccggaccccgaggtgacatgcgtggtggtggacgtgtcccacgaggatcctgaggtgaagttcaattgg tatgtcgatggcgtggaggtgcacaacgctaagacaaagcctcgggaggagcagtacaattctacctata gggtggtgagcgtgctgacagtgctgcaccaggactggctcaatggcaaggagtataagtgcaaggtgtc taacaaggccctgcccgctcctatcgagaagaccatcagcaaggccaagggccagcctagagagccacag gtgtacacactgcctccatctcgggacgagctgaccaagaatcaggtgagcctgacatgtctggtgaagg gcttctatcctagcgatatcgccgtggagtgggagtccaacggccagccagagaacaattacaagaccac accccctgtgctggactctgatggcagcttctttctgtattccaagctgaccgtggataagtctaggtgg cagcagggcaacgtgttttcctgttctgtgatgcacgaagccctgcataatcactatactcagaaatccc tgtcactgtcacctggtaaa
```

SEQ ID NO: 36 is an exemplary nucleic acid sequence encoding a chimeric light chain including the 2B8 V$_L$ and a human IgG1 constant region.

```
gacattgtgatgactcagtcccataaattcatgtctaccctggtgggcgaccgggtgagcatcacatgca aggcctctcaggatgtgagcaccacagtggcttggtaccagcagaagccaggccagtcccccaagctgct gatctattccgcctcttatcggtataccggagtgcctgacaggttcaccggaagcggatccggcacagat ttcacctttacaatcagctccgtgcaggccgaggacctggccgtgtactattgccagcagcactactcta tccctagaacctttggcggcggcacaaagctggagatcaagcggaccgtggccgctccaagcgtgttcat cttcccccttccgacgagcagctgaagtccggcacagcttctgtggtgtgcctgctgaacaatttctac cccagggaggccaaggtccagtggaaggtggataacgctctgcagtctggcaatagccaggagtccgtga ccgagcaggactctaaggatagcacatattccctgtctagcaccctgacactgagcaaggccgattacga gaagcacaaggtgtatgcttgtgaagtcactcatcagggtctgtcttcacctgtcactaagtcttttaac cgaggcgaatgc
```

SEQ ID NOs: 37-46 are amino acid sequences concerning chimeric antigen receptors.

SEQ ID NOs: 47-49 are peptide linker sequences.

SEQ ID NO: 21 is the amino acid sequences of a chimeric heavy chain including the 4A10 V$_H$ and a human IgG1 constant region.

SEQ ID NOs: 37-46 are amino acid sequences concerning chimeric antigen receptors.

SEQ ID NOs: 47-49 are peptide linker sequences.

DETAILED DESCRIPTION

I. Abbreviations

ADC antibody-drug conjugate
ADCC antibody-dependent cellular cytotoxicity
ALL acute lymphoblastic leukemia
CAR chimeric antigen receptor
CD3 cluster of differentiation 3 T cell coreceptor
CDR complementarity determining region
CXC4 C—X—C chemokine receptor type 4
E:T effector:target
HCDR heavy chain complementarity determining region
hIgG human immunoglobulin G
IgG immunoglobulin G
IL-7 interleukin-7
IL-7Rα interleukin-7 receptor c
LCDR light chain complementarity determining region
LDH lactate dehydrogenase
NK natural killer
scFv single chain antibody
T-ALL T cell derived acute lymphoblastic leukemia
B-ALL B cell derived acute lymphoblastic leukemia
TSLP thymic stromal lymphopoietin
V$_H$ heavy chain variable region
V$_L$ light chain variable region

II. Summary of Terms

Unless otherwise noted, technical terms are used according to conventional usage. Definitions of common terms in molecular biology may be found in Benjamin Lewin, Genes X, published by Jones & Bartlett Publishers, 2009; and Meyers et al. (eds.), *The Encyclopedia of Cell Biology and Molecular Medicine*, published by Wiley-VCH in 16 volumes, 2008; and other similar references.

As used herein, the singular forms "a," "an," and "the," refer to both the singular as well as plural, unless the context clearly indicates otherwise. For example, the term "an antigen" includes single or plural antigens and can be considered equivalent to the phrase "at least one antigen." As used herein, the term "comprises" means "includes." It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described herein. In case of conflict, the present specification, including explanations of terms, will control. In addition, the materials, methods, and examples are illustrative only and not intended to be limiting. To facilitate review of the various embodiments, the following explanations of terms are provided:

Acute Lymphoblastic Leukemia (ALL): An acute leukemia involving the overproduction and accumulation of cancerous lymphoblasts (immature B- and/or T cells). ALL is the most common cancer in children. Treatment for ALL has improved dramatically in recent decades, but there remain about 20% of cases that are not cured and it remains a leading cause of death in children. ALL can be subdivided into two broad groups: leukemias derived from immature T cells (T-ALL) and leukemias derived from immature B cells (B-ALL). The majority of T-ALL and B-ALL cells express IL-7Rα and respond to IL-7 in vitro, showing increased survival and proliferation (see, e.g., Barata et al., *Blood*, 98:1524-1531, 2001; Touw et al., *Blood*, 75:2097-2101, 1990).

Methods of diagnosing ALL in a subject, or diagnosing a subject with ALL as having T-ALL or B-ALL are known (see, for example, Chiaretti et al., "Diagnosis and Subclassification of Acute Lymphoblastic Leukemia," *Mediterranean J Hematol Infect Dis*, 6(1): e2014073, 2014).

T-ALL can be caused by gain-of-function mutations in the IL-7Rα gene (see, Zenatti et al., *Nat. Genet.*, 43:932-939, 2011). These mutations are often insertions into exon 6 of IL-7Rα that encode cysteine residues. Additionally, other gain-of-function mutations in the IL-7 pathway that contribute to T cell or B cell proliferation are known (such as gain-of-function mutations in the genes encoding, Jak1, Jak3, Stat5b, Ras or AKT), as well as in B-ALL (such as gain-of-function mutations in the genes encoding TSLPR or Jak2).

Administration: The introduction of a composition into a subject by a chosen route. Administration can be local or systemic. For example, if the chosen route is intravenous, the composition is administered by introducing the composition into a vein of the subject. Exemplary routes of administration include, but are not limited to, oral, injection (such as subcutaneous, intramuscular, intradermal, intraperitoneal, and intravenous), sublingual, rectal, transdermal (for example, topical), intranasal, vaginal, and inhalation routes.

AMD3100: A CXCR4 antagonist currently sold by Genzyme Corporation as an immunostimulants used to mobilize hematopoietic stem cells from bone marrow to the blood stream. AMD3100 is also known as Plerixafor and Mozobil®. The chemical structure of AMD3100 is provided as:

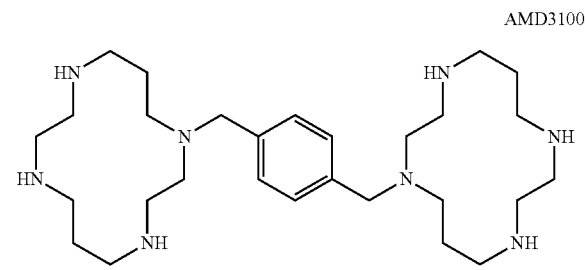 [SMILES: c1cc(CN2CCCNCCNCCCNCC2)ccc1CN1CCCNCCNCCCNCC1]

AMD3100

Use and dosages for AMD3100 are known, see, e.g., Hummel et al., Curr Opin. Hematolog., 21(1):29-36, 2014 and Liu et al., Exp. Hematol. Opin., 5:19, 2016.

Amino acid substitution: The replacement of one amino acid in peptide with a different amino acid.

Antibody: An immunoglobulin, antigen-binding fragment, or derivative thereof, that specifically binds and recognizes an analyte (antigen) such as IL-7Rα. The term "antibody" is used herein in the broadest sense and encompasses various antibody structures, including but not limited to monoclonal antibodies, polyclonal antibodies, multispecific antibodies (e.g., bispecific antibodies), and antibody fragments, so long as they exhibit the desired antigen-binding activity.

Non-limiting examples of antibodies include, for example, intact immunoglobulins and variants and fragments thereof known in the art that retain binding affinity for the antigen. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments. Antibody fragments include antigen binding fragments either produced by the modification of whole antibodies or those synthesized de novo using recombinant DNA methodologies (see, e.g., Kontermann and Dubel (Ed), Antibody Engineering, Vols. 1-2, $2^{nd}$ Ed., Springer Press, 2010).

A single-chain antibody (scFv) is a genetically engineered molecule containing the $V_H$ and $V_L$ domains of one or more antibody(ies) linked by a suitable polypeptide linker as a genetically fused single chain molecule (see, for example, Bird et al., *Science*, 242:423-426, 1988; Huston et al., *Proc. Natl. Acad. Sci.*, 85:5879-5883, 1988; Ahmad et al., *Clin. Dev. Immunol.*, 2012, doi:10.1155/2012/980250; Marbry, *IDrugs*, 13:543-549, 2010). The intramolecular orientation of the $V_H$-domain and the $V_L$-domain in a scFv, is typically not decisive for scFvs. Thus, scFvs with both possible arrangements ($V_H$-domain-linker domain-$V_L$-domain; $V_L$-domain-linker domain-$V_H$-domain) may be used.

In a dsFv the $V_H$ and $V_L$ have been mutated to introduce a disulfide bond to stabilize the association of the chains. Diabodies also are included, which are bivalent, bispecific antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see, for example, Holliger et al., *Proc. Natl. Acad. Sci.*, 90:6444-6448, 1993; Poljak et al., *Structure*, 2:1121-1123, 1994).

Antibodies also include genetically engineered forms such as chimeric antibodies (such as humanized murine antibodies) and heteroconjugate antibodies (such as bispecific antibodies). See also, *Pierce Catalog and Handbook*, 1994-1995 (Pierce Chemical Co., Rockford, IL); Kuby, J., *Immunology*, 3$^{rd}$ Ed., W.H. Freeman & Co., New York, 1997.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. Antibody competition assays are known, and an exemplary competition assay is provided herein.

An antibody may have one or more binding sites. If there is more than one binding site, the binding sites may be identical to one another or may be different. For instance, a naturally occurring immunoglobulin has two identical binding sites, a single-chain antibody or Fab fragment has one binding site, while a bispecific or bifunctional antibody has two different binding sites.

Typically, a naturally occurring immunoglobulin has heavy chains and light chains interconnected by disulfide bonds. Immunoglobulin genes include the kappa, lambda, alpha, gamma, delta, epsilon and mu constant region genes, as well as the myriad immunoglobulin variable domain genes. There are two types of light chain, lambda (λ) and kappa (κ). There are five main heavy chain classes (or isotypes) which determine the functional activity of an antibody molecule: IgM, IgD, IgG, IgA and IgE.

Each heavy and light chain contains a constant region (or constant domain) and a variable region (or variable domain; see, e.g., Kindt et al. Kuby Immunology, 6$^{th}$ ed., W.H. Freeman and Co., page 91 (2007).) In several embodiments, the $V_H$ and $V_L$ Combine to specifically bind the antigen. In additional embodiments, only the $V_H$ is required. For example, naturally occurring camelid antibodies consisting of a heavy chain only are functional and stable in the absence of light chain (see, e.g., Hamers-Casterman et al., *Nature*, 363:446-448, 1993; Sheriff et al., *Nat. Struct. Biol.*, 3:733-736, 1996). References to "$V_H$" or "VH" refer to the variable region of an antibody heavy chain, including that of an antigen binding fragment, such as Fv, scFv, dsFv or Fab. References to "$V_L$" or "VL" refer to the variable domain of an antibody light chain, including that of an Fv, scFv, dsFv or Fab.

The $V_H$ and $V_L$ contain a "framework" region interrupted by three hypervariable regions, also called "complementarity-determining regions" or "CDRs" (see, e.g., Kabat et al., *Sequences of Proteins of Immunological Interest*, U.S. Department of Health and Human Services, 1991). The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The amino acid sequence boundaries of a given CDR can be readily determined using any of a number of well-known schemes, including those described by Kabat et al. ("Sequences of Proteins of Immunological Interest," 5th Ed. Public Health Service, National Institutes of Health, Bethesda, MD, 1991; "Kabat" numbering scheme), Al-Lazikani et al., (JMB 273,927-948, 1997; "Chothia" numbering scheme), and Lefranc et al. ("IMGT unique numbering for immunoglobulin and T cell receptor variable domains and Ig superfamily V-like domains," Dev. Comp. Immunol., 27:55-77, 2003; "IMGT" numbering scheme). The CDRs of each chain are typically referred to as CDR1, CDR2, and CDR3 (from the N-terminus to C-terminus), and are also typically identified by the chain in which the particular CDR is located. Thus, a $V_H$ CDR3 is the CDR3 from the $V_H$ of the antibody in which it is found, whereas a $V_L$ CDR1 is the CDR1 from the $V_L$ of the antibody in which it is found. Light chain CDRs are sometimes referred to as LCDR1, LCDR2, and LCDR3. Heavy chain CDRs are sometimes referred to as HCDR1, HCDR2, and HCDR3.

A "monoclonal antibody" is an antibody obtained from a population of substantially homogeneous antibodies, that is, the individual antibodies comprising the population are identical and/or bind the same epitope, except for possible variant antibodies, for example, containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein. In some examples monoclonal antibodies are isolated from a subject. Monoclonal antibodies can have conservative amino acid substitutions, which have substantially no effect on antigen binding or other immunoglobulin functions. (See, for example, Harlow & Lane, *Antibodies, A Laboratory Manual*, 2$^{nd}$ ed. Cold Spring Harbor Publications, New York (2013).)

A "humanized" antibody or antigen binding fragment includes a human framework region and one or more CDRs from a non-human (such as a mouse, rat, or synthetic) antibody or antigen binding fragment. The non-human antibody or antigen binding fragment providing the CDRs is termed a "donor," and the human antibody or antigen binding fragment providing the framework is termed an "acceptor." In one embodiment, all the CDRs are from the donor immunoglobulin in a humanized immunoglobulin. Constant regions need not be present, but if they are, they can be substantially identical to human immunoglobulin constant regions, such as at least about 85-90%, such as about 95% or more identical. Hence, all parts of a humanized antibody or antigen binding fragment, except possibly the CDRs, are substantially identical to corresponding parts of natural human antibody sequences.

A "chimeric antibody" is an antibody which includes sequences derived from two different antibodies, and are typically of different species. In some examples, a chimeric antibody includes one or more CDRs and/or framework regions from one human antibody and CDRs and/or framework regions from another human antibody. In other embodiments, a chimeric antibody can include the $V_H$ and $V_L$ regions of a mouse monoclonal antibody (such as the 4A10 or 2B8 antibody) and human constant regions, such as human IgG1 regions.

A "fully human antibody" or "human antibody" is an antibody, which includes sequences from (or derived from) the human genome, and does not include sequence from another species. In some embodiments, a human antibody includes CDRs, framework regions, and (if present) an Fc region from (or derived from) the human genome. Human antibodies can be identified and isolated using technologies for creating antibodies based on sequences derived from the human genome, for example by phage display or using transgenic animals (see, e.g., Barbas et al. *Phage display: A Laboratory Manuel.* 1st Ed. New York: Cold Spring Harbor Laboratory Press, 2004. Print.; Lonberg, *Nat. Biotech.,* 23: 1117-1125, 2005; Lonenberg, *Curr. Opin. Immunol.,* 20:450-459, 2008)

Antibody-drug conjugate (ADC): A molecule that includes an antibody (or antigen-binding fragment of an antibody) conjugated to a drug, such as a cytotoxic agent. ADCs can be used to specifically target a cytotoxic agent to cancer cells through specific binding of the antibody to a tumor antigen expressed on the cell surface. Exemplary drugs for use with ADCs include anti-microtubule agents (such as maytansinoids, auristatin E and auristatin F) and interstrand crosslinking agents (e.g., pyrrolobenzodiazepines or PDBs).

Autoimmune disease: A disorder in which the immune system produces an immune response (for example, a B cell or a T cell response) against an endogenous antigen, with consequent injury to tissues. For example, rheumatoid arthritis is an autoimmune disorder, as are Hashimoto's thyroiditis, pernicious anemia, Addison's disease, type I diabetes, systemic lupus erythematosus, Atopic dermatitis, Inhalation Allergy, dermatomyositis, Sjogren's syndrome, dermatomyositis, lupus erythematosus, multiple sclerosis, myasthenia gravis, Reiter's syndrome, Primary Biliary Cirrhosis, Inflammatory bowel disease, and Grave's disease, among others.

Biological sample: A sample obtained from a subject. Biological samples include all clinical samples useful for detection of disease (for example, T-ALL) in subjects, including, but not limited to, cells, tissues, and bodily fluids, such as blood, derivatives and fractions of blood (such as serum), cerebrospinal fluid; as well as biopsied or surgically removed tissue, for example tissues that are unfixed, frozen, or fixed in formalin or paraffin. In a particular example, a biological sample is obtained from a subject having or suspected of having T-ALL.

Bispecific antibody: A recombinant molecule composed of two different antigen binding domains that consequently binds to two different antigenic epitopes. Bispecific antibodies include chemically or genetically linked molecules of two antigen-binding domains. The antigen binding domains can be linked using a linker. The antigen binding domains can be monoclonal antibodies, antigen-binding fragments (e.g., Fab, scFv), or combinations thereof. A bispecific antibody can include one or more constant domains, but does not necessarily include a constant domain.

CD3 (Cluster of differentiation 3 T cell Co-receptor): A specific protein complex including at least four polypeptide chains, which are non-covalently associated with the T cell receptors on the surface of T cells. The four polypeptide chains include two CD3-epsilon chains, a CD3-delta chain and a CD3-gamma chain. CD3 is present on both helper T cells and cytotoxic T cells.

Chemotherapeutic agent: Any chemical agent with therapeutic usefulness in the treatment of diseases characterized by abnormal cell growth. For example, chemotherapeutic agents can be useful for the treatment of cancer, such as T-ALL or B-ALL, such as in combination therapy with one or more of the disclosed IL-7Rα-specific antibodies. Particular examples of chemotherapeutic agents that can be used include microtubule binding agents, DNA intercalators or cross-linkers, DNA synthesis inhibitors, DNA and RNA transcription inhibitors, antibodies, enzymes, enzyme inhibitors, gene regulators, and angiogenesis inhibitors. In one embodiment, a chemotherapeutic agent is a radioactive compound. In another embodiments, the chemotherapeutic agent is a CXCR4 antagonist, such as AMD3100. One of skill in the art can readily identify a chemotherapeutic agent of use (see for example, Slapak and Kufe, *Principles of Cancer Therapy,* Chapter 86 in Harrison's Principles of Internal Medicine, 14th edition; Perry et al., *Chemotherapy,* Ch. 17 in Abeloff, Clinical Oncology $2^{nd}$ ed., © 2000 Churchill Livingstone, Inc; Baltzer, L., Berkery, R. (eds): *Oncology Pocket Guide to Chemotherapy,* 2nd ed. St. Louis, Mosby-Year Book, 1995; Fischer, D. S., Knobf, M. F., Durivage, H. J. (eds): *The Cancer Chemotherapy Handbook,* 4th ed. St. Louis, Mosby-Year Book, 1993; Chabner and Longo, *Cancer Chemotherapy and Biotherapy: Principles and Practice* (4th ed.). Philadelphia: Lippincott Willians & Wilkins, 2005; Skeel, *Handbook of Cancer Chemotherapy* (6th ed.). Lippincott Williams & Wilkins, 2003). Combination chemotherapy is the administration of more than one agent to treat cancer.

Chimeric Antigen Receptor (CAR): An engineered T cell receptor having an extracellular antibody-derived targeting domain (such as an scFv) joined to one or more intracellular signaling domains of a T cell receptor. A "chimeric antigen receptor T cell" is a T cell expressing a CAR, and has antigen specificity determined by the antibody-derived targeting domain of the CAR. Methods of making CARs are available (see, e.g., Park et al., *Trends Biotechnol.,* 29:550-557, 2011; Grupp et al., N Engl J Med., 368:1509-1518, 2013; Han et al., J. Hematol Oncol., 6:47, 2013; PCT Pubs. WO2012/079000, WO2013/059593; and U.S. Pub. 2012/0213783, each of which is incorporated by reference herein in its entirety.) Conditions sufficient to form an immune complex: Conditions which allow an antibody or antigen binding fragment thereof to bind to its cognate epitope to a detectably greater degree than, and/or to the substantial exclusion of, binding to substantially all other epitopes. Conditions sufficient to form an immune complex are dependent upon the format of the binding reaction and typically are those utilized in immunoassay protocols or those conditions encountered in vivo. See Harlow & Lane (*Antibodies, A Laboratory Manual,* $2^{nd}$ ed. Cold Spring Harbor Publications, New York, 2013) for a description of immunoassay formats and conditions. The conditions employed in the methods are "physiological conditions" which include reference to conditions (e.g., temperature, osmolarity, pH) that are typical inside a living mammal or a mammalian cell. While it is recognized that some organs are subject to extreme conditions, the intra-organismal and intracellular environment normally lies around pH 7 (e.g., from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

The formation of an immune complex can be detected through conventional methods known to the skilled artisan, for instance immunohistochemistry, immunoprecipitation, flow cytometry, immunofluorescence microscopy, ELISA, immunoblotting (for example, Western blot), magnetic resonance imaging, CT scans, X-ray and affinity chromatography. Immunological binding properties of selected antibodies may be quantified using methods well known in the art.

Conjugate: A complex of two molecules linked together, for example, linked together by a covalent bond. In one embodiment, an antibody is linked to an effector molecule; for example, an antibody that specifically binds to IL-7Rα covalently linked to an effector molecule. The linkage can be by chemical or recombinant means. In one embodiment, the linkage is chemical, wherein a reaction between the antibody moiety and the effector molecule has produced a covalent bond formed between the two molecules to form one molecule. A peptide linker (short peptide sequence) can optionally be included between the antibody and the effector molecule. Because conjugates can be prepared from two molecules with separate functionalities, such as an antibody and an effector molecule, they are also sometimes referred to as "chimeric molecules."

Conservative variants: "Conservative" amino acid substitutions are those substitutions that do not substantially affect or decrease a function of a protein, such as the ability of the protein to interact with a target protein. For example, an IL-7Rα-specific antibody can include up to 1, 2, 3, 4, 5, 6, 7, 8, 9, or up to 10 conservative substitutions compared to a reference antibody sequence and retain specific binding activity for IL-7Rα. The term conservative variation also includes the use of a substituted amino acid in place of an unsubstituted parent amino acid.

Furthermore, one of ordinary skill will recognize that individual substitutions, deletions or additions which alter, add or delete a single amino acid or a small percentage of amino acids (for instance less than 5%, in some embodiments less than 1%) in an encoded sequence are conservative variations where the alterations result in the substitution of an amino acid with a chemically similar amino acid.

Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Non-conservative substitutions are those that reduce an activity or function of the IL-7Rα-specific antibody, such as the ability to specifically bind to IL-7Rα. For instance, if an amino acid residue is essential for a function of the protein, even an otherwise conservative substitution may disrupt that activity. Thus, a conservative substitution does not alter the basic function of a protein of interest.

Contacting: Placement in direct physical association; includes both in solid and liquid form, which can take place either in vivo or in vitro. Contacting includes contact between one molecule and another molecule, for example the amino acid on the surface of one polypeptide, such as an antigen, that contacts another polypeptide, such as an antibody. Contacting can also include contacting a cell for example by placing an antibody in direct physical association with a cell.

Control: A reference standard. In some embodiments, the control is a negative control, such as sample obtained from a healthy patient that does not have ALL. In other embodiments, the control is a positive control, such as a tissue sample obtained from a patient diagnosed with ALL. In still other embodiments, the control is a historical control or standard reference value or range of values (such as a previously tested control sample, such as a group of ALL patients with known prognosis or outcome, or group of samples that represent baseline or normal values).

A difference between a test sample and a control can be an increase or conversely a decrease. The difference can be a qualitative difference or a quantitative difference, for example a statistically significant difference. In some examples, a difference is an increase or decrease, relative to a control, of at least about 5%, such as at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, or at least about 500%.

CXCR4: C—X—C chemokine receptor type 4 (CXCR4), also known as fusin or cluster of differentiation 184 (CD184). CXCR4 is a seven transmembrane G-protein coupled receptor belonging to Class I GPCR or rhodopsin-like GPCR family. Stromal-derived-factor-1 (SDF-1) is known to be a CXCR4 ligand, and SDF-1 binding to CXCR4 is believed to promote hematopoietic stem cell homing to bone marrow. An exemplary CXCR4 protein sequence is provided as GenBank Accession No. CAA12166.1, which is incorporated by reference herein in its entirety.

CXCR4 antagonist: An agent that decreases CXCR4 signaling activity in cells. Non-limiting examples of CXCR4 antagonists include small molecule inhibitors that of CXCR4 signaling and antibodies that specifically the extracellular region of CXCR4 on the cell surface and inhibit CXCR4 signaling. A specific example of a CXCR4 antagonists includes AMD3100 (Plerixafor, Genzyme Corp.). Additional CXCR4 antagonists are described, for example, in Debnath et al., Theranostics, 3(1):47-75, 2013 and Grande et al., Curr Pharm Des., 14:385-404, 2008, each of which is incorporated by reference herein in its entirety.

Degenerate variant: In the context of the present disclosure, a "degenerate variant" refers to a polynucleotide encoding a protein (for example, an antibody that specifically binds IL-7Rα) that includes a sequence that is degenerate as a result of the genetic code. There are twenty natural amino acids, most of which are specified by more than one codon. Therefore, all degenerate nucleotide sequences are included as long as the amino acid sequence of the antibody that binds IL-7Rα encoded by the nucleotide sequence is unchanged.

Detectable marker: A detectable molecule (also known as a label) that is conjugated directly or indirectly to a second molecule, such as an antibody, to facilitate detection of the second molecule. For example, the detectable marker can be capable of detection by ELISA, spectrophotometry, flow cytometry, microscopy or diagnostic imaging techniques (such as CT scans, MRIs, ultrasound, fiberoptic examination, and laparoscopic examination). Specific, non-limiting examples of detectable markers include fluorophores, chemiluminescent agents, enzymatic linkages, radioactive isotopes and heavy metals or compounds (for example super paramagnetic iron oxide nanocrystals for detection by MRI). In one example, a "labeled antibody" refers to incorporation of another molecule in the antibody. For example, the label is a detectable marker, such as the incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionuclides (such as $^{35}$S or $^{131}$I) fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance. Methods for using detectable markers and guidance in the choice of detectable markers appropriate for various purposes are discussed for example in Sambrook et al. (Molecular Cloning: A Laboratory Manual, 4$^{th}$ ed, Cold Spring Harbor, New York, 2012) and Ausubel et al. (In Current Protocols in Molecular Biology, John Wiley & Sons, New York, through supplement 104, 2013).

Detecting: To identify the existence, presence, or fact of something. General methods of detecting are known to the skilled artisan and may be supplemented with the protocols and reagents disclosed herein. For example, included herein are methods of detecting a cell that expresses IL-7Rα.

Diagnostic: Identifying the presence or nature of a pathologic condition, such as, but not limited to, cancer. Diagnostic methods differ in their sensitivity and specificity. The "sensitivity" of a diagnostic assay is the percentage of diseased individuals who test positive (percent of true positives). The "specificity" of a diagnostic assay is one minus the false positive rate, where the false positive rate is defined as the proportion of those without the disease who test positive. While a particular diagnostic method may not provide a definitive diagnosis of a condition, it suffices if the method provides a positive indication that aids in diagnosis. "Prognostic" is the probability of development (e.g., severity) of a pathologic condition, such as cancer or metastasis.

Drug: Any compound used to treat, ameliorate or prevent a disease or condition in a subject. In some embodiments herein, the drug is a chemotherapeutic agent, for example a cytotoxic agent, such as an anti-mitotic or anti-microtubule agent.

Effector molecule: A molecule intended to have or produce a desired effect; for example, a desired effect on a cell to which the effector molecule is targeted. Effector molecules can include, for example, polypeptides and small molecules. In one non-limiting example, the effector molecule is a chemotherapeutic agent. The skilled artisan will understand that some effector molecules may have or produce more than one desired effect. In one example, an effector molecule is the portion of a chimeric molecule, for example a chimeric molecule that includes a disclosed antibody or fragment thereof, that is intended to have a desired effect on a cell or tissue to which the chimeric molecule is targeted.

Epitope: An antigenic determinant. These are particular chemical groups or peptide sequences on a molecule that are antigenic, i.e. that elicit a specific immune response. An antibody specifically binds a particular antigenic epitope on a polypeptide. In some examples a disclosed antibody specifically binds to an epitope on IL-7Rα.

Expression: Transcription or translation of a nucleic acid sequence. For example, a gene can be expressed when its DNA is transcribed into an RNA or RNA fragment, which in some examples is processed to become mRNA. A gene may also be expressed when its mRNA is translated into an amino acid sequence, such as a protein or a protein fragment. In a particular example, a heterologous gene is expressed when it is transcribed into an RNA. In another example, a heterologous gene is expressed when its RNA is translated into an amino acid sequence. Regulation of expression can include controls on transcription, translation, RNA transport and processing, degradation of intermediary molecules such as mRNA, or through activation, inactivation, compartmentalization or degradation of specific protein molecules after they are produced.

Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see for example, Bitter et al., *Methods in Enzymology* 153:516-544, 1987). For example, when cloning in bacterial systems, inducible promoters such as pL of bacteriophage lambda, plac, ptrp, ptac (ptrp-lac hybrid promoter) and the like may be used. In one embodiment, when cloning in mammalian cell systems, promoters derived from the genome of mammalian cells (such as metallothionein promoter) or from mammalian viruses (such as the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences.

A polynucleotide can be inserted into an expression vector that contains a promoter sequence, which facilitates the efficient transcription of the inserted genetic sequence of the host. The expression vector typically contains an origin of replication, a promoter, as well as specific nucleic acid sequences that allow phenotypic selection of the transformed cells.

Expression vector: A vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

Fc polypeptide: The polypeptide including the constant region of an antibody excluding the first constant region immunoglobulin domain. Fc region generally refers to the last two constant region immunoglobulin domains of IgA, IgD, and IgG, and the last three constant region immunoglobulin domains of IgE and IgM. An Fc region may also include part or all of the flexible hinge N-terminal to these domains. For IgA and IgM, an Fc region may or may not include the tailpiece, and may or may not be bound by the J chain. For IgG, the Fc region includes immunoglobulin domains Cgamma2 and Cgamma3 (Cγ2 and Cγ3) and the lower part of the hinge between Cgamma1 (Cγ1) and Cγ2. Although the boundaries of the Fc region may vary, the human IgG heavy chain Fc region is usually defined to include residues C226 or P230 to its carboxyl-terminus, wherein the numbering is according to the EU index as in Kabat. For IgA, the Fc region includes immunoglobulin domains Calpha2 and Calpha3 (Cα2 and C3) and the lower part of the hinge between Calpha1 (Cα1) and Cα2.

IgA: A polypeptide belonging to the class of antibodies that are substantially encoded by a recognized immunoglobulin alpha gene. In humans, this class or isotype comprises $IgA_1$ and $IgA_2$. IgA antibodies can exist as monomers, polymers (referred to as pIgA) of predominantly dimeric form, and secretory IgA. The constant chain of wild-type IgA contains an 18-amino-acid extension at its C-terminus called the tail piece (tp). Polymeric IgA is secreted by plasma cells with a 15-kDa peptide called the J chain linking two monomers of IgA through the conserved cysteine residue in the tail piece.

IgG: A polypeptide belonging to the class or isotype of antibodies that are substantially encoded by a recognized immunoglobulin gamma gene. In humans, this class comprises $IgG_1$, $IgG_2$, $IgG_3$, and $IgG_4$. In mice, this class comprises $IgG_1$, $IgG_{2a}$, $IgG_{2b}$, $IgG_3$.

Interleukin-7 (IL-7): A product of stromal cells and a ligand for the IL-7 receptor. IL-7 is normally required for T and B cell development and for survival of mature T cells. Binding of IL-7 to its receptor activates the Jak/Stat signaling pathway, leading to cell survival and proliferation.

Interleukin-7 receptor α chain (IL-7Rα): Also known as CD127, IL-7Rα is a type-I cytokine receptor predominantly expressed by lymphocytes and it binds to IL-7 and γc to transduce a signal that increases lymphocyte survival and proliferation. IL-7Rα includes an extracellular domain, a transmembrane domain, and an intracellular domain. IL-7 binding to IL-7Rα leads to heterodimerization with the common γc chain (on T cells). On B cells, IL-7Rα heterodimerizes with TSLP and TSLP receptor. Heterodimerization triggers phosphorlyation events that ultimately lead to Stat5b homodimerization and translocation to the nucleus, where Stat5b serves as a transcription factor that induces genes involved in cell survival and proliferation. Gain-of-function mutations in IL-7Rα are known to cause aberrant IL-7Rα homodimerization and phosphorylation of Stat5b, resulting in lymphocyte overproduction. An exemplary amino acid sequence for IL-7Rα is provided as NCBI Ref. NP_002176.2, which is incorporated by reference herein as present in the database on Sep. 30, 2015.

IL-7Rα-positive cancer: An abnormal (for example, malignant) growth of tissue or cells that express IL-7Rα protein, the abnormal growth of tissue or cells resulting from excessive cell division. In some embodiments, the IL-7Rα-positive cancer comprises cells that over-express IL-7Rα. In additional embodiments, the IL-7Rα positive cancer comprises cells that express an IL-7Rα protein with one or more mutations that result in increased IL-7Rα signaling activity, for example, the increased IL-7Rα signaling activity can result in increased phosphorylation of Stat5b compared to a normal control. In some embodiments, the IL-7Rα-positive cancer can be a hematological cancer or a lymphoid cancer. In some embodiments, the IL-7Rα-positive cancer can be a leukemia that expresses IL-7Rα, such as an acute lymphoblastic leukemia (for example a T-ALL or B-ALL) that expresses IL-7Rα.

Standard methods can be used to determine an expression or signaling activity level of IL-7Rα in a cancer tissue or cell. For example, a sample of the cancer tissue or cells can be taken from a subject and tested for binding to an IL-7Rα-specific antibody to determine IL-7Rα expression, for example, to identify the cancer as having overexpression of IL-7Rα-positive compared to a normal control. In some embodiments, a sample of the cancer can be taken from a subject and tested for Stat5b phosphorylation compared to a normal control to assess IL-7Rα signaling activity.

In some embodiments the IL-7Rα-positive cancer can be a hematological or lymphoid cancer; non-limiting examples include leukemias, for example acute leukemias (such as acute lymphoblastic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), a polycythemia vera, a lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia. In several embodiments, the IL-7Rα-positive cancer can be an acute lymphoblastic leukemia, such as T-ALL or B-ALL.

In some embodiments, the IL-7Rα-positive cancer can be a solid cancer; non-limiting examples include sarcomas and carcinomas, including fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma).

Isolated: A biological component (such as a nucleic acid, peptide, protein or protein complex, for example an antibody) that has been substantially separated, produced apart from, or purified away from other biological components in the cell of the organism in which the component naturally occurs, that is, other chromosomal and extra-chromosomal DNA and RNA, and proteins. Thus, isolated nucleic acids, peptides and proteins include nucleic acids and proteins purified by standard purification methods. The term also embraces nucleic acids, peptides and proteins prepared by recombinant expression in a host cell, as well as, chemically synthesized nucleic acids. A isolated nucleic acid, peptide or protein, for example an antibody, can be at least 50%, at least 60%, at least 70%, at least 80%, at least 90%, at least 95%, at least 96%, at least 97%, at least 98%, or at least 99% pure.

Linker: A bi-functional molecule that can be used to link two molecules into one contiguous molecule, for example, to link an effector molecule to an antibody. In some embodiments, the provided conjugates include a linker between the effector molecule or detectable marker and an antibody. In some cases, a linker is a peptide within an antigen binding fragment (such as an Fv fragment) which serves to indirectly bond the $V_H$ and $V_L$. Non-limiting examples of peptide linkers include a glycine-serine linkers such as GGGGS (SEQ ID NO: 47), GGGGSGGGGS SEQ ID NO: 48), or a GGGGSGGGGSGGGGS (SEQ ID NO: 49) linker.

The terms "conjugating," "joining," "bonding," or "linking" can refer to making two molecules into one contiguous molecule; for example, linking two polypeptides into one contiguous polypeptide, or covalently attaching an effector molecule or detectable marker radionuclide or other molecule to a polypeptide, such as an scFv. In the specific context, the terms include reference to joining a ligand, such as an antibody moiety, to an effector molecule. The linkage can be either by chemical or recombinant means. "Chemical means" refers to a reaction between the antibody moiety and the effector molecule such that there is a covalent bond formed between the two molecules to form one molecule.

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

"cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The nucleotides can be ribonucleotides, deoxyribonucleotides, or modified forms of either nucleotide. The term includes single- and double-stranded forms of DNA.

Operably linked: A first nucleic acid sequence is operably linked with a second nucleic acid sequence when the first nucleic acid sequence is placed in a functional relationship with the second nucleic acid sequence. For instance, a promoter, such as the CMV promoter, is operably linked to a coding sequence if the promoter affects the transcription or expression of the coding sequence.

Generally, operably linked DNA sequences are contiguous and, where necessary to join two protein-coding regions, in the same reading frame.

Pharmaceutically acceptable carriers: The pharmaceutically acceptable carriers of use are conventional. *Remington's Pharmaceutical Sciences*, by E. W. Martin, Mack Publishing Co., Easton, PA, 19th Edition, 1995, describes compositions and formulations suitable for pharmaceutical delivery of the disclosed agents.

In general, the nature of the carrier will depend on the particular mode of administration being employed. For instance, parenteral formulations usually include injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, added preservatives (such as on-natural preservatives), and pH buffering agents and the like, for example sodium acetate or sorbitan monolaurate. In particular examples, the pharmaceutically acceptable carrier is sterile and suitable for parenteral administration to a subject for example, by injection. In some embodiments, the active agent and pharmaceutically acceptable carrier are provided in a unit dosage form such as a pill or in a selected quantity in a vial. Unit dosage forms can include one dosage or multiple dosages (for example, in a vial from which metered dosages of the agents can selectively be dispensed).

Polypeptide: A polymer in which the monomers are amino acid residues that are joined together through amide bonds. When the amino acids are alpha-amino acids, either the L-optical isomer or the D-optical isomer can be used, the L-isomers being preferred. The terms "polypeptide" or "protein" as used herein are intended to encompass any amino acid sequence and include modified sequences such as glycoproteins. A polypeptide includes both naturally occurring proteins, as well as those that are recombinantly or synthetically produced. A polypeptide has an amino terminal (N-terminal) end and a carboxy-terminal end. In some embodiments, the polypeptide is a disclosed antibody or a fragment thereof.

Polypeptide modifications: polypeptides can be modified by a variety of chemical techniques to produce derivatives having essentially the same activity and conformation as the unmodified peptides, and optionally having other desirable properties. For example, carboxylic acid groups of the protein, whether carboxyl-terminal or side chain, may be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring. Amino groups of the peptide, whether amino-terminal or side chain, may be in the form of a pharmaceutically-acceptable acid addition salt, such as the HCl, HBr, acetic, benzoic, toluene sulfonic, maleic, tartaric and other organic salts, or may be modified to $C_1$-$C_{16}$ alkyl or dialkyl amino or further converted to an amide.

Hydroxyl groups of the peptide side chains can be converted to $C_1$-$C_{16}$ alkoxy or to a $C_1$-$C_{16}$ ester using well-recognized techniques. Phenyl and phenolic rings of the peptide side chains can be substituted with one or more halogen atoms, such as F, Cl, Br or I, or with $C_1$-$C_{16}$ alkyl, $C_1$-$C_{16}$ alkoxy, carboxylic acids and esters thereof, or amides of such carboxylic acids. Methylene groups of the peptide side chains can be extended to homologous $C_2$-$C_4$ alkylenes. Thiols can be protected with any one of a number of well-recognized protecting groups, such as acetamide groups.

Recombinant: A recombinant nucleic acid is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, for example, by genetic engineering techniques. A recombinant protein is one that has a sequence that is not naturally occurring or has a sequence that is made by an artificial combination of two otherwise separated segments of sequence. In several embodiments, a recombinant protein is encoded by a heterologous (for example, recombinant) nucleic acid that has been introduced into a host cell, such as a bacterial or eukaryotic cell. The nucleic acid can be introduced, for example, on an expression vector having signals capable of expressing the protein encoded by the introduced nucleic acid or the nucleic acid can be integrated into the host cell chromosome.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a polypeptide will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, MD) and on the internet, for use in connection with the sequence analysis programs blastp, blastn, blastx, tblastn and tblastx. A description of how to determine sequence identity using this program is available on the NCBI website on the internet.

Homologs and variants of a $V_L$ or a $V_H$ of an antibody that specifically binds a polypeptide are typically characterized by possession of at least about 75%, for example at least about 80%, 85%, 90%, 91%, 92%, 93%, 94%, 95%, 96%, 97%, 98% or 99% sequence identity counted over the full length alignment with the amino acid sequence of interest. Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Terms used to describe sequence relationships between two or more nucleotide sequences or amino acid sequences include "reference sequence," "selected from," "comparison window," "identical," "percentage of sequence identity," "substantially identical," "complementary," and "substantially complementary."

For sequence comparison of nucleic acid sequences, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are used. Methods of alignment of sequences for comparison are well known in the art. Optimal alignment of sequences for comparison can be conducted, e.g., by the local homology algorithm of Smith & Waterman, *Adv. Appl. Math.* 2:482, 1981, by the homology alignment algorithm of Needleman & Wunsch, *J. Mol. Biol.* 48:443, 1970, by the search for similarity method of Pearson & Lipman, *Proc. Nat'l. Acad. Sci. USA* 85:2444, 1988, by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., Sambrook et al. (Molecular Cloning: A Laboratory Manual, 4$^{th}$ ed, Cold Spring Harbor, New York, 2012) and Ausubel et al. (In Current Protocols in Molecular Biology, John Wiley & Sons, New York, through supplement 104, 2013). One example of a useful algorithm is PILEUP. PILEUP uses a simplification of the progressive alignment method of Feng & Doolittle, *J. Mol. Evol.* 35:351-360, 1987. The method used is similar to the method described by Higgins & Sharp, *CABIOS* 5:151-153, 1989. Using PILEUP, a reference sequence is compared to other test sequences to determine the percent sequence identity relationship using the following parameters: default gap weight (3.00), default gap length weight (0.10), and unweighted end gaps. PILEUP can be obtained from the GCG sequence analysis software package, e.g., version 7.0 (Devereaux et al., *Nuc. Acids Res.* 12:387-395, 1984.

Another example of algorithms that are suitable for determining percent sequence identity and sequence similarity are the BLAST and the BLAST 2.0 algorithm, which are described in Altschul et al., *J. Mol. Biol.* 215:403-410, 1990 and Altschul et al., *Nucleic Acids Res.* 25:3389-3402, 1977. Software for performing BLAST analyses is publicly available through the National Center for Biotechnology Information (ncbi.nlm.nih.gov). The BLASTN program (for nucleotide sequences) uses as defaults a word length (W) of 11, alignments (B) of 50, expectation (E) of 10, M=5, N=-4, and a comparison of both strands. The BLASTP program (for amino acid sequences) uses as defaults a word length (W) of 3, and expectation (E) of 10, and the BLOSUM62 scoring matrix (see Henikoff & Henikoff, *Proc. Natl. Acad. Sci. USA* 89:10915, 1989). An oligonucleotide is a linear polynucleotide sequence of up to about 100 nucleotide bases in length.

Specifically bind: When referring to an antibody or antigen binding fragment, refers to a binding reaction which determines the presence of a target protein, peptide, or polysaccharide in the presence of a heterogeneous population of proteins and other biologics. Thus, under designated conditions, an antibody binds preferentially to a particular target protein, peptide or polysaccharide (such as IL-7Rα) and does not bind in a significant amount to other proteins or polysaccharides present in the sample or subject. Specific binding can be determined by methods known in the art. With reference to an antibody-antigen complex, specific binding of the antigen and antibody has a $K_D$ of less than about $10^{-7}$ Molar, such as less than about $10^{-8}$ Molar, $10^{-9}$, or even less than about $10^{-10}$ Molar.

$K_D$ refers to the dissociation constant for a given interaction, such as a polypeptide ligand interaction or an antibody antigen interaction. For example, for the bimolecular interaction of an antibody or antigen binding fragment and an antigen it is the concentration of the individual components of the bimolecular interaction divided by the concentration of the complex.

The antibodies disclosed herein specifically bind to a defined target (or multiple targets, in the case of a bispecific antibody). Thus, an antibody that specifically binds to an epitope on IL-7Rα is an antibody that binds substantially to IL-7Rα, including cells or tissue expressing IL-7Rα, substrate to which the IL-7Rα is attached, or IL-7Rα in a biological specimen. It is, of course, recognized that a certain degree of non-specific interaction may occur between an antibody or conjugate including an antibody (such as an antibody that specifically binds IL-7Rα or conjugate including such antibody) and a non-target (such as a cell that does not express IL-7Rα). Typically, specific binding results in a much stronger association between the antibody and protein or cells bearing the antigen than between the antibody and protein or cells lacking the antigen. Specific binding typically results in greater than 2-fold, such as greater than 5-fold, greater than 10-fold, or greater than 100-fold increase in amount of bound antibody (per unit time) to a protein including the epitope or cell or tissue expressing the target epitope as compared to a protein or cell or tissue lacking this epitope. Specific binding to a protein under such conditions requires an antibody that is selected for its specificity for a particular protein. A variety of immunoassay formats are appropriate for selecting antibodies or other ligands specifically immunoreactive with a particular protein. For example, solid-phase ELISA immunoassays are routinely used to select monoclonal antibodies specifically immunoreactive with a protein. See Harlow & Lane, *Antibodies, A Laboratory Manual*, 2$^{nd}$ ed., Cold Spring Harbor Publications, New York (2013), for a description of immunoassay formats and conditions that can be used to determine specific immunoreactivity.

Subject: Living multi-cellular vertebrate organisms, a category that includes human and non-human mammals. In an example, a subject is a human. In a particular example, the subject is a pediatric subject, such as a human child age 2-5 years old. In an additional example, a subject is selected that has ALL (such as T-ALL) or is at risk of having ALL (such as T-ALL).

Therapeutically effective amount: The amount of an agent (such as an IL-7Rα specific antibody or a conjugate including an IL-7Rα specific antibody) that alone, or together with one or more additional agents, induces the desired response, such as, for example treatment of an IL-7Rα-positive cancer, in a subject. When administered to a subject, a dosage will generally be used that will achieve target tissue concentrations that has been shown to achieve a desired in vitro effect. Ideally, a therapeutically effective amount provides a therapeutic effect without causing a substantial cytotoxic effect in the subject.

In one example, a desired response is to decrease the size, volume, or number (such as metastases) of IL-7Rα-positive cancer cells in a subject, and/or neoplastic lesions or number of leukemia cells in blood in a subject. For example, the agent or agents can decrease the size, volume, or number of IL-7Rα-positive cancer cells, and/or neoplastic lesions or number of leukemia cells in blood by a desired amount, for example by at least 5%, at least 10%, at least 15%, at least 20%, at least 25%, at least 30%, at least 50%, at least 75%, at least 90%, or at least 95% as compared to a response in the absence of the agent.

Several preparations disclosed herein are administered in therapeutically effective amounts. A therapeutically effective amount of an antibody that specifically binds IL-7Rα or antigen binding fragment thereof, or conjugate thereof (or a composition including one or more of these molecules) that is administered to a human or veterinary subject will vary depending upon a number of factors associated with that subject, for example the overall health of the subject. A therapeutically effective amount can be determined by varying the dosage and measuring the resulting therapeutic response, such as the regression of an IL-7Rα-positive cancer. Therapeutically effective amounts also can be determined through various in vitro, in vivo or in situ immunoassays. The disclosed agents can be administered in a single dose, or in several doses, as needed to obtain the desired response. However, the therapeutically effective amount of can be dependent on the source applied, the subject being treated, the severity and type of the condition being treated, and the manner of administration.

A therapeutically effective amount encompasses a fractional dose that contributes in combination with previous or subsequent administrations to attaining a therapeutic response. For example, a therapeutically effective amount of an agent can be administered in a single dose, or in several doses, for example daily, during a course of treatment lasting several days or weeks. However, the therapeutically effective amount can depend on the subject being treated, the severity and type of the condition being treated, and the manner of administration. A unit dosage form of the agent can be packaged in a therapeutic amount, or in multiples of the therapeutic amount, for example, in a vial (e.g., with a pierceable lid) or syringe having sterile components.

Toxin: An effector molecule that induces cytotoxicity when it contacts a cell. Specific, non-limiting examples of toxins include, but are not limited to, abrin, ricin, auristatins (such as monomethyl auristatin E (MMAE; see for example, Francisco et al., Blood, 102: 1458-1465, 2003)) and monomethyl auristatin F (MMAF; see, for example, Doronina et al., BioConjugate Chem., 17: 114-124, 2006), maytansinoids (such as DM1; see, for example, Phillips et al., Cancer Res., 68:9280-9290, 2008), *Pseudomonas* exotoxin (PE, such as PE35, PE37, PE38, and PE40), diphtheria toxin (DT), botulinum toxin, saporin, restrictocin or gelonin, or modified toxins thereof, or other toxic agents that directly or indirectly inhibit cell growth or kill cells. For example, PE and DT are highly toxic compounds that typically bring about death through liver toxicity. PE and DT, however, can be modified into a form for use as an immunotoxin by removing the native targeting component of the toxin (such as the domain Ia of PE and the B chain of DT) and replacing it with a different targeting moiety, such as an antibody.

Transformed: A transformed cell is a cell into which a nucleic acid molecule has been introduced by molecular biology techniques. As used herein, the term transformation encompasses all techniques by which a nucleic acid molecule might be introduced into such a cell, including transfection with viral vectors, transformation with plasmid vectors, and introduction of DNA by electroporation, lipofection, and particle gun acceleration.

Treating or Preventing a disease: "Preventing" a disease refers to inhibiting the full development of a disease. "Treating" refers to a therapeutic intervention that ameliorates a sign or symptom of a disease or pathological condition after it has begun to develop, such as a reduction in tumor burden or a decrease in the number of size of metastases. "Ameliorating" refers to the reduction in the number or severity of signs or symptoms of a disease, such as cancer.

Vector: A nucleic acid molecule as introduced into a host cell, thereby producing a transformed host cell. Recombinant DNA vectors are vectors having recombinant DNA. A vector can include nucleic acid sequences that permit it to replicate in a host cell, such as an origin of replication. A vector can also include one or more selectable marker genes and other genetic elements known in the art. Viral vectors are recombinant nucleic acid vectors having at least some nucleic acid sequences derived from one or more viruses. A replication deficient viral vector is a vector that requires complementation of one or more regions of the viral genome required for replication due to a deficiency in at least one replication-essential gene function. For example, such that the viral vector does not replicate in typical host cells, especially those in a human patient that could be infected by the viral vector in the course of a therapeutic method.

III. Description of Several Embodiments

A. Monoclonal Antibodies and Antigen Binding Fragments

Isolated monoclonal antibodies and antigen binding fragments that specifically bind an epitope on the extracellular domain of IL-7Rα are provided. In several embodiments, the antibodies or antigen binding fragments can specifically bind to IL-7Rα on the surface of a cell, such as a T-ALL cell.

This disclosure provides the novel 4A10 and 2B8 antibodies and variants thereof, including antigen binding fragments. Epitope mapping and competition binding studies show that the disclosed antibodies and antigen binding fragments specifically bind to non-overlapping epitopes on the extracellular domain of IL-7Rα.

The disclosed antibodies and antigen binding fragments are surprisingly effective for treatment of ALL, such as T-ALL and B-ALL. For example, as discussed in Example 1, a chimeric antibody including the 4A10 heavy and light chain variable regions and human IgG1 constant regions prolonged survival and mediated ADCC killing of IL-7Rα-positive cancer cells in an in vivo model of T-ALL.

In some embodiments, the antibodies and antigen binding fragments include a $V_H$ and a $V_L$ and specifically bind to IL-7Rα. In some embodiments, the antibody or antigen binding fragment includes a $V_H$ comprising one or more (i.e., one, two or all three) HCDRs from the 4A10 or 2B8 antibody and specifically binds to the extracellular domain of IL-7Rα. In some embodiments, the antibody or antigen binding fragment includes a $V_L$ comprising one or more (i.e., one, two or all three) LCDRs from one of the 4A10 or 2B8 antibody and specifically binds to the extracellular domain of IL-7Rα. In several embodiments, the antibody or antigen binding fragment includes a $V_H$ and a $V_L$ including the HCDR1, HCDR2, and HCDR3, and LCDR1, LCDR2, and LCDR3, respectively, of the 4A10 or 2B8 antibody, and specifically binds to the extracellular domain of IL-7Rα.

In some embodiments, the antibody or antigen binding fragment includes a HCDR1, a HCDR2, a HCDR3, a LCDR1, a LCDR2, and a LCDR3 comprising amino acid sequences that are at least 90%, for example, at least 91%, at least 92%, at least 93%, at least 94%, at least 95%, at least 96%, at least 97%, at least 98%, at least 99% or 100% identical to the amino acid sequences of the CDRs of one of the 4A10 or 2B8 antibody, wherein the antibody specifically binds to the extracellular domain of IL-7Rα.

The person of ordinary skill in the art will understand that various CDR numbering schemes (such as the Kabat, Chothia or IMGT numbering schemes) can be used to determine CDR positions. The amino acid sequence and the CDR positions of the heavy and light chain of the 4A10 and 2B8 antibodies according to the Kabat numbering scheme are shown in Table 1. The discussion of monoclonal antibodies below refers to monoclonal antibodies that include a $V_H$ and a $V_L$ including CDRs with reference to the Kabat numbering scheme (unless the context indicates otherwise). In some embodiments, the antibody or antigen binding fragment includes one or more Kabat CDRs, such as those listed in Table 1.

TABLE 1

Kabat CDR sequences of IL-7Rα specific antibodies.

4A10 $V_H$

| $V_H$ | SEQ ID NO: 1 positions | CDR protein sequence | CDR SEQ ID NO |
|---|---|---|---|
| HCDR1 | 31-35 | SYWMH | 5 |
| HCDR2 | 50-66 | EIDPSDSYTNDNQKFKG | 6 |
| HCDR3 | 99-111 | RLYSNSYYYAMDY | 7 |

4A10 $V_L$

| $V_L$ | SEQ ID NO: 2 positions | A.A. Sequence | CDR SEQ ID NO |
|---|---|---|---|
| LCDR1 | 24-34 | KASQDIKKYIA | 8 |
| LCDR2 | 50-56 | YTSTLQP | 9 |
| LCDR3 | 89-96 | LQYDNLLT | 10 |

2B8 $V_H$

| $V_H$ | SEQ ID NO: 3 positions | CDR protein sequence | CDR SEQ ID NO |
|---|---|---|---|
| HCDR1 | 31-35 | DYYMH | 11 |
| HCDR2 | 50-66 | YIYPDNGGNGYNQKFKG | 12 |
| HCDR3 | 99-109 | GTYYDGSYFDY | 13 |

2B8 $V_L$

| $V_L$ | SEQ ID NO: 4 positions | A.A. Sequence | CDR SEQ ID NO |
|---|---|---|---|
| LCDR1 | 24-34 | KASQDVSTTVA | 14 |
| LCDR2 | 50-56 | SASYRYT | 15 |
| LCDR3 | 89-97 | QQHYSIPRT | 16 |

4A10

In some embodiments, the antibody or antigen binding fragment can be based on or derived from the 4A10 antibody. For example, in some embodiments, the antibody or antigen binding fragment includes a $V_H$ including a HCDR1, a HCDR2, and/or a HCDR3 including amino acids 31-35, 50-66, and 99-111 of SEQ ID NO: 1, respectively, wherein the antibody or antigen binding fragment specifically binds to the extracellular domain of IL-7Rα. In further embodiments, the antibody or antigen binding fragment includes a $V_L$ including a LCDR1, a LCDR2, and/or a LCDR3 including amino acids 24-34, 50-56, and 89-96 of SEQ ID NO: 2, respectively, wherein the antibody or antigen binding fragment specifically binds to the extracellular domain of IL-7Rα. In additional embodiments, the antibody or antigen binding fragment includes a $V_H$ including a HCDR1, a HCDR2, and/or a HCDR3 including amino acids 31-35, 50-66, and 99-111 of SEQ ID NO: 1, respectively, and a $V_L$ including a LCDR1, a LCDR2, and/or a LCDR3 including amino acids 24-34, 50-56, and 89-96 of SEQ ID NO: 2, respectively, wherein the antibody or antigen binding fragment specifically binds to the extracellular domain of IL-7Rα.

In some embodiments, the antibody or antigen binding fragment includes a $V_H$ including a HCDR1, a HCDR2, and a HCDR3 including amino acids 31-35, 50-66, and 99-111 of SEQ ID NO: 1, respectively, wherein the antibody or antigen binding fragment specifically binds to the extracellular domain of IL-7Rα. In further embodiments, the antibody or antigen binding fragment includes a $V_L$ including a LCDR1, a LCDR2, and a LCDR3 including amino acids 24-34, 50-56, and 89-96 of SEQ ID NO: 2, respectively, wherein the antibody or antigen binding fragment specifically binds to the extracellular domain of IL-7Rα. In additional embodiments, the antibody or antigen binding fragment includes a $V_H$ including a HCDR1, a HCDR2, and a HCDR3 including amino acids 31-35, 50-66, and 99-111 of SEQ ID NO: 1, respectively, and a $V_L$ including a LCDR1, a LCDR2, and a LCDR3 including amino acids 24-34, 50-56, and 89-96 of SEQ ID NO: 2, respectively, wherein the antibody or antigen binding fragment specifically binds to the extracellular domain of IL-7Rα.

In some embodiments, an isolated antibody or antigen binding fragment includes at least one CDR with a sequence that has at least 95% sequence identity to any one of SEQ ID NOs: 5-10, wherein the antibody specifically binds to IL-7Rα. In some embodiments, the antibody or antigen binding fragment includes a $V_H$ including a HCDR1, a HCDR2, and a HCDR3 including amino acid sequences at least 90% (such as at least 95%, at least 96%, at least 97%, at least 98%, or at least 99%) identical to amino acids 31-35, 50-66, and 99-111, respectively, of SEQ ID NO: 1, wherein the antibody or antigen binding fragment specifically binds to the extracellular domain of IL-7Rα. In some embodiments, the antibody or antigen binding fragment includes a $V_L$ including a LCDR1, a LCDR2, and a LCDR3 including amino acid sequences at least 90% (such as at least 95%, at least 96%, at least 97%, at least 98%, or at least 99%) identical to amino acids amino acids 24-34, 50-56, and 89-96, respectively, of SEQ ID NO: 2, wherein the antibody or antigen binding fragment specifically binds to the extracellular domain of IL-7Rα. In additional embodiments, the antibody or antigen binding fragment includes a $V_H$ including a HCDR1, a HCDR2, and a HCDR3 including amino acid sequences at least 90% (such as at least 95%, at least 96%, at least 97%, at least 98%, or at least 99%) identical to amino acids 31-35, 50-66, and 99-111, respectively, of SEQ ID NO: 1, and a $V_L$ including a LCDR1, a LCDR2, and a LCDR3 including amino acid sequences at least 90% (such as at least 95%, at least 96%, at least 97%, at least 98%, or at least 99%) identical to amino acids amino acids 24-34, 50-56, and 89-96, respectively, of SEQ ID NO: 2, wherein the antibody or antigen binding fragment specifically binds to the extracellular domain of IL-7Rα.

In some embodiments, the antibody or antigen binding fragment includes a $V_H$ including an amino acid sequence at least 90% (such as at least 95%, at least 96%, at least 97%, at least 98%, or at least 99%) to the amino acid sequence set forth as SEQ ID NO: 1, wherein the antibody or antigen binding fragment specifically binds to the extracellular domain of IL-7Rα. In more embodiments, the antibody or antigen binding fragment includes a $V_L$ including an amino acid sequence at least 90% (such as at least 95%, at least 96%, at least 97%, at least 98%, or at least 99%) to the amino acid sequence set forth as SEQ ID NO: 2, wherein the antibody or antigen binding fragment specifically binds to the extracellular domain of IL-7Rα. In additional embodiments, the antibody or antigen binding fragment includes a $V_H$ including an amino acid sequence at least 90% (such as at least 95%, at least 96%, at least 97%, at least 98%, or at least 99%) to the amino acid sequence set forth as SEQ ID NO: 1, and a $V_L$ including an amino acid sequence at least 90% (such as at least 95%, at least 96%, at least 97%, at least 98%, or at least 99%) to the amino acid sequence set forth as SEQ ID NO: 2, wherein the antibody or antigen binding fragment specifically binds to the extracellular domain of IL-7Rα.

In additional embodiments, the antibody or antigen binding fragment includes a $V_H$ including the amino acid sequence set forth as one of SEQ ID NO: 1, wherein the antibody or antigen binding fragment specifically binds to the extracellular domain of IL-7Rα. In more embodiments, the antibody or antigen binding fragment includes a $V_L$ including the amino acid sequence set forth as SEQ ID NO: 2, wherein the antibody or antigen binding fragment specifically binds to the extracellular domain of IL-7Rα. In some embodiments, the antibody or antigen binding fragment includes a $V_H$ and a $V_L$ including the amino acid sequences set forth as SEQ ID NOs: 1 and 2, respectively, wherein the antibody or antigen binding fragment specifically binds to the extracellular domain of IL-7Rα.

In some embodiments, the antibody or antigen binding fragment includes a HCDR1, a HCDR2, and a HCDR3, comprising the amino acid sequences set forth as SEQ ID NOs: 5, 6, and 7, respectively, wherein the antibody or antigen binding fragment specifically binds to the extracellular domain of IL-7Rα. In some embodiments, the antibody or antigen binding fragment includes a LCDR1, a LCDR2, and a LCDR3, comprising the amino acid sequences set forth as SEQ ID NOs: 8, 9, and 10, respectively, wherein the antibody or antigen binding fragment specifically binds to the extracellular domain of IL-7Rα. In some embodiments, the antibody or antigen binding fragment includes a HCDR1, a HCDR2, a HCDR3, a LCDR1, a LCDR2, and a LCDR3, comprising the amino acid sequences set forth as SEQ ID NOs: 5, 6, 7, 8, 9, and 10, respectively, wherein the antibody or antigen binding fragment specifically binds to the extracellular domain of IL-7Rα.

2B8

In some embodiments, the antibody or antigen binding fragment can be based on or derived from the 4A10 antibody. For example, in some embodiments, the antibody or antigen binding fragment includes a $V_H$ including a HCDR1, a HCDR2, and/or a HCDR3 including amino acids 31-35, 50-66, and 99-109 of SEQ ID NO: 3, respectively, wherein the antibody or antigen binding fragment specifically binds to the extracellular domain of IL-7Rα. In further embodiments, the antibody or antigen binding fragment includes a $V_L$ including a LCDR1, a LCDR2, and/or a LCDR3 including amino acids 24-34, 50-56, and 89-97 of SEQ ID NO: 4, respectively, wherein the antibody or antigen binding fragment specifically binds to the extracellular domain of IL-7Rα. In additional embodiments, the antibody or antigen binding fragment includes a $V_H$ including a HCDR1, a HCDR2, and/or a HCDR3 including amino acids 31-35, 50-66, and 99-109 of SEQ ID NO: 3, respectively, and a $V_L$ including a LCDR1, a LCDR2, and/or a LCDR3 including amino acids 24-34, 50-56, and 89-97 of SEQ ID NO: 4, respectively, wherein the antibody or antigen binding fragment specifically binds to the extracellular domain of IL-7Rα.

In some embodiments, the antibody or antigen binding fragment includes a $V_H$ including a HCDR1, a HCDR2, and a HCDR3 including amino acids 31-35, 50-66, and 99-109 of SEQ ID NO: 3, respectively, wherein the antibody or antigen binding fragment specifically binds to the extracellular domain of IL-7Rα. In further embodiments, the antibody or antigen binding fragment includes a $V_L$ including a LCDR1, a LCDR2, and a LCDR3 including amino acids 24-34, 50-56, and 89-97 of SEQ ID NO: 4, respectively, wherein the antibody or antigen binding fragment specifically binds to the extracellular domain of IL-7Rα. In additional embodiments, the antibody or antigen binding fragment includes a $V_H$ including a HCDR1, a HCDR2, and a HCDR3 including amino acids 31-35, 50-66, and 99-109 of SEQ ID NO: 3, respectively, and a $V_L$ including a LCDR1, a LCDR2, and a LCDR3 including amino acids 24-34, 50-56, and 89-97 of SEQ ID NO: 4, respectively, wherein the antibody or antigen binding fragment specifically binds to the extracellular domain of IL-7Rα.

In some embodiments, an isolated antibody or antigen binding fragment includes at least one CDR with a sequence that has at least 95% sequence identity to any one of SEQ ID NOs: 11-16, wherein the antibody specifically binds to IL-7Rα. In some embodiments, the antibody or antigen binding fragment includes a $V_H$ including a HCDR1, a HCDR2, and a HCDR3 including amino acid sequences at least 90% (such as at least 95%, at least 96%, at least 97%, at least 98%, or at least 99%) identical to amino acids 31-35, 50-66, and 99-109, respectively, of SEQ ID NO: 3, wherein the antibody or antigen binding fragment specifically binds to the extracellular domain of IL-7Rα. In some embodiments, the antibody or antigen binding fragment includes a $V_L$ including a LCDR1, a LCDR2, and a LCDR3 including amino acid sequences at least 90% (such as at least 95%, 96%, 97%, 98%, or 99%) identical to amino acids amino acids 24-34, 50-56, and 89-97, respectively, of SEQ ID NO: 4, wherein the antibody or antigen binding fragment specifically binds to the extracellular domain of IL-7Rα. In additional embodiments, the antibody or antigen binding fragment includes a $V_H$ including a HCDR1, a HCDR2, and a HCDR3 including amino acid sequences at least 90% (such as at least 95%, at least 96%, at least 97%, at least 98%, or at least 99%) identical to amino acids 31-35, 50-66, and 99-109, respectively, of SEQ ID NO: 3, and a $V_L$ including a LCDR1, a LCDR2, and a LCDR3 including amino acid sequences at least 90% (such as at least 95%, at least 96%, at least 97%, at least 98%, or at least 99%) identical to amino acids amino acids 24-34, 50-56, and 89-97, respectively, of SEQ ID NO: 4, wherein the antibody or antigen binding fragment specifically binds to the extracellular domain of IL-7Rα.

In some embodiments, the antibody or antigen binding fragment includes a $V_H$ including an amino acid sequence at least 90% (such as at least 95%, at least 96%, at least 97%, at least 98%, or at least 99%) to the amino acid sequence set forth as SEQ ID NO: 3, wherein the antibody or antigen binding fragment specifically binds to the extracellular domain of IL-7Rα. In more embodiments, the antibody or antigen binding fragment includes a $V_L$ including an amino acid sequence at least 90% (such as at least 95%, at least 96%, at least 97%, at least 98%, or at least 99%) identical to the amino acid sequence set forth as SEQ ID NO: 4, wherein the antibody or antigen binding fragment specifically binds to the extracellular domain of IL-7Rα. In additional embodiments, the antibody or antigen binding fragment includes a $V_H$ including an amino acid sequence at least 90% (such as at least 95%, at least 96%, at least 97%, at least 98%, or at least 99%) identical to the amino acid sequence set forth as SEQ ID NO: 3, and a $V_L$ including an amino acid sequence at least 90% (such as at least 95%, at least 96%, at least 97%, at least 98%, or at least 99%) identical to the amino acid sequence set forth as SEQ ID NO: 4, wherein the antibody or antigen binding fragment specifically binds to the extracellular domain of IL-7Rα.

In additional embodiments, the antibody or antigen binding fragment includes a $V_H$ including the amino acid sequence set forth as one of SEQ ID NO: 3, wherein the antibody or antigen binding fragment specifically binds to the extracellular domain of IL-7Rα. In more embodiments, the antibody or antigen binding fragment includes a $V_L$ including the amino acid sequence set forth as SEQ ID NO: 4, wherein the antibody or antigen binding fragment specifically binds to the extracellular domain of IL-7Rα. In some embodiments, the antibody or antigen binding fragment includes a $V_H$ and a $V_L$ including the amino acid sequences set forth as SEQ ID NOs: 3 and 4, respectively, wherein the antibody or antigen binding fragment specifically binds to the extracellular domain of IL-7Rα.

In some embodiments, the antibody or antigen binding fragment includes a HCDR1, a HCDR2, and a HCDR3, comprising the amino acid sequences set forth as SEQ ID NOs: 11, 12, and 13, respectively, wherein the antibody or antigen binding fragment specifically binds to the extracellular domain of IL-7Rα. In some embodiments, the antibody or antigen binding fragment includes a LCDR1, a LCDR2, and a LCDR3, comprising the amino acid sequences set forth as SEQ ID NOs: 14, 15, and 16, respectively, wherein the antibody or antigen binding fragment specifically binds to the extracellular domain of IL-7Rα. In some embodiments, the antibody or antigen binding fragment includes a HCDR1, a HCDR2, a HCDR3, a LCDR1, a LCDR2, and a LCDR3, comprising the amino acid sequences set forth as SEQ ID NOs: 11, 12, 13, 14, 15, and 16, respectively, wherein the antibody or antigen binding fragment specifically binds to the extracellular domain of IL-7Rα.

1. Additional Description of Antibodies and Antigen Binding Fragments

The 4A10 and 2B8 antibodies were originally isolated from mouse hybridoma cell lines. In some embodiments, a humanized antibody is provided that includes the CDRs of the 4A10 or 2B8 antibody and human framework regions. Chimeric antibodies (for example, including mouse variable regions and human constant regions) are also provided. The antibody or antigen binding fragment can include any suitable framework region, such as (but not limited to) a human framework region. Human framework regions, and mutations that can be made in a human antibody framework regions, are known in the art (see, for example, in U.S. Pat. No. 5,585,089, which is incorporated herein by reference). Alternatively, a heterologous framework region, such as, but not limited to a mouse or monkey framework region, can be included in the heavy or light chain of the antibodies. (See, for example, Jones et al., *Nature* 321:522, 1986; Riechmann et al., *Nature* 332:323, 1988; Verhoeyen et al., *Science* 239:1534, 1988; Carter et al., *Proc. Natl. Acad. Sci. U.S.A.* 89:4285, 1992; Sandhu, *Crit. Rev. Biotech.* 12:437, 1992; and Singer et al., *J. Immunol.* 150:2844, 1993.)

The antibody can be of any isotype. The antibody can be, for example, an IgM or an IgG antibody, such as $IgG_1$, $IgG_2$, $IgG_3$, or $IgG_4$. The class of an antibody that specifically binds IL-7Rα can be switched with another. In one aspect, a nucleic acid molecule encoding $V_L$ or $V_H$ is isolated using methods well-known in the art, such that it does not include any nucleic acid sequences encoding the constant region of the light or heavy chain, respectively. In a non-limiting example, the $V_H$ amino acid sequence is set forth as SEQ ID NO: 1, and the $V_L$ amino acid sequence is set forth as SEQ ID NO: 2. In another non-limiting example, the $V_H$ amino acid sequence is set forth as SEQ ID NO: 3, and the $V_L$ amino acid sequence is set forth as SEQ ID NO: 4. A nucleic acid molecule encoding $V_L$ or $V_H$ is then operatively linked to a nucleic acid sequence encoding a $C_L$ or $C_H$ from a different class of immunoglobulin molecule. This can be achieved using a vector or nucleic acid molecule that comprises a $C_L$ or $C_H$ chain, as known in the art. For example, an antibody that specifically binds IL-7Rα, that was originally IgG may be class switched to an IgM. Class switching can be used to convert one IgG subclass to another, such as from $IgG_1$ to $IgG_2$, $IgG_3$, or $IgG_4$.

In some examples, the disclosed antibodies are oligomers of antibodies, such as dimers, trimers, tetramers, pentamers, hexamers, septamers, octomers and so on.

In several embodiments, the disclosed antibody can mediate ADCC killing of IL-7Rα positive cells, such as T-ALL cells. In some embodiments, the disclosed antibody can inhibit IL-7 induced signaling through the IL-7R in cells, such as T-ALL cells. Methods of evaluating IL-7-induced signaling through the IL-7® are known and include, for example, evaluation of pSTAT5 induction in the presence of IL-7.

(A) Binding Affinity

In several embodiments, the antibody or antigen binding fragment can specifically bind IL-7Rα with an affinity (e.g., measured by $K_D$) of no more than $1.0 \times 10^{-8}$ M, no more than $5.0 \times 10^{-8}$ M, no more than $1.0 \times 10^{-9}$ M, no more than $5.0 \times 10^{-9}$ M, no more than $1.0 \times 10^{-10}$ M, no more than $5.0 \times 10^{-10}$ M, or no more than $1.0 \times 10^{-11}$ M. $K_D$ can be measured, for example, by a radiolabeled antigen binding assay (RIA) performed with the Fab version of an antibody of interest and its antigen using known methods. In one assay, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g, Chen et al, *J. Mol. Biol.* 293:865-881 (1999)). To establish conditions for the assay, MICROTITER® multi-well plates (Thermo Scientific) are coated overnight with 5 μg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 μM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20@) in PBS. When the plates have dried, 150 μl/well of scintillant (MICROSCINT-20™; Packard) is added, and the plates are counted on a TOP-COUNT™ gamma counter (Packard) for ten minutes. Concentrations of each Fab that give less than or equal to 20% of maximal binding are chosen for use in competitive binding assays.

In another assay, $K_D$ can be measured using surface plasmon resonance assays using a Biacore™ T-100 or a Biacore™-3000 instrument (GE Life Sciences, Inc., Piscataway, N.J.) at 25° C. with immobilized antigen CM5 chips at ~10 response units (RU). Briefly, carboxymethylated dextran biosensor chips (CM5, GE Life Sciences, Inc.) are activated with N-ethyl-N'-(3-dimethylaminopropyl)-carbodiimide hydrochloride (EDC) and N-hydroxysuccinimide (NIS) according to the supplier's instructions. Antigen is diluted with 10 mM sodium acetate, pH 4.8, to 5 μg/ml (~0.2 μM) before injection at a flow rate of 5 μl/min to achieve approximately 10-50 response units (RUs) of coupled protein. Following the injection of antigen, 1 M ethanolamine is injected to block unreacted amino groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 μl/min. Association rates ($k_{on}$) and dissociation rates ($k_{off}$) are calculated using a simple one-to-one Langmuir binding model (Biacore™ Evaluation Software version 3.2) by simultaneously fitting the association and dissociation phases of the sensorgrams. The equilibrium dissociation constant ($K_d$) is calculated as the ratio $k_{off}/k_{on}$. See, e.g., Chen et at, *J. Mol. Biol.* 293:865-881 (1999). If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

(b) Multispecific Antibodies

In some embodiments, the antibody or antigen binding fragment is included on a multispecific antibody, such as a bi-specific antibody. Such multispecific antibodies can be produced by known methods, such as crosslinking two or more antibodies, antigen binding fragments (such as scFvs) of the same type or of different types. Exemplary methods of making multispecific antibodies include those described in PCT Pub. No. WO2013/163427, which is incorporated by reference herein in its entirety. Suitable crosslinkers include those that are heterobifunctional, having two distinctly reactive groups separated by an appropriate spacer (such as m-maleimidobenzoyl-N-hydroxysuccinimide ester) or homobifunctional (such as disuccinimidyl suberate). Such linkers are available from Pierce Chemical Company, Rockford, Ill.

In some embodiments, the antibody or antigen binding fragment is included on a bispecific antibody that that specifically binds to IL-7Rα and further specifically binds to CD3, such as in the context of a B-specific T cell engager (BiTE). Examples of CD3 binding domains that can be included on the bispecific antibody or antigen binding fragment are known and include those disclosed in PCT Pub. No. WO2013/163427, which is incorporated by reference herein in its entirety.

Various types of multi-specific antibodies are known. Bispecific single chain antibodies can be encoded by a single nucleic acid molecule. Examples of bispecific single chain antibodies, as well as methods of constructing such antibodies are known in the art (see, e.g., U.S. Pat. Nos. 8,076,459, 8,017,748, 8,007,796, 7,919,089, 7,820,166, 7,635,472, 7,575,923, 7,435,549, 7,332,168, 7,323,440, 7,235,641, 7,229,760, 7,112,324, 6,723,538, incorporated by reference herein). Additional examples of bispecific single chain antibodies can be found in PCT application No. WO 99/54440; Mack, *J. Immunol.*, 158:3965-3970, 1997; Mack, *PNAS*, 92:7021-7025, 1995; Kufer, *Cancer Immunol. Immunother.*, 45:193-197, 1997; Loffler, *Blood*, 95:2098-2103, 2000; and Bruhl, *J. Immunol.*, 166:2420-2426, 2001. Production of bispecific Fab-scFv ("bibody") molecules are described, for example, in Schoonjans et al. (J. Immunol. 165:7050-57, 2000) and Willems et al. (J Chromatogr B Analyt Technol Biomed Life Sci. 786:161-76, 2003). For bibodies, a scFv molecule can be fused to one of the VL-CL (L) or VH-CH1 chains, e.g., to produce a bibody one scFv is fused to the C-term of a Fab chain.

(c) Fragments

Antigen binding fragments are encompassed by the present disclosure, such as Fab, F(ab')$_2$, and Fv which include a $V_H$ and $V_L$ (for example, with the CDRs of the 4A10 or 2B8 mAb) and specifically bind IL-7Rα. These antibody fragments retain the ability to selectively bind with the antigen and are "antigen-binding" fragments. Non-limiting examples of such fragments include:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, a genetically engineered fragment containing the V$_L$ and V$_L$ expressed as two chains; and (5) Single chain antibody (such as scFv), defined as a genetically engineered molecule containing the V$_H$ and the V$_L$ linked by a suitable polypeptide linker as a genetically fused single chain molecule (see, e.g., Ahmad et al., Clin. Dev. Immunol., 2012, doi:10.1155/2012/980250; Marbry, IDrugs, 13:543-549, 2010). The intramolecular orientation of the V$_H$-domain and the V$_L$-domain in a scFv, is not decisive for the provided antibodies (e.g., for the provided multispecific antibodies). Thus, scFvs with both possible arrangements (V$_H$-domain-linker domain-V$_L$-domain; V$_L$-domain-linker domain-V$_H$-domain) may be used.

(6) A dimer of a single chain antibody (scFV$_2$), defined as a dimer of a scFV. This has also been termed a "miniantibody."

Methods of making these fragments are known in the art (see for example, Harlow and Lane, *Antibodies: A Laboratory Manual*, 2$^{nd}$, Cold Spring Harbor Laboratory, New York, 2013).

In some embodiments, the antibody binding fragment can be an Fv antibody, which is typically about 25 kDa and contain a complete antigen-binding site with three CDRs per each heavy chain and each light chain. To produce Fv antibodies, the V$_H$ and the V$_L$ can be expressed from two individual nucleic acid constructs in a host cell. In another example, the V$_H$ amino acid sequence of the antigen binding fragment includes the CDRs from SEQ ID NO: 1 and/or the sequence set forth as one of SEQ ID NO: 1, and the V$_L$ amino acid sequence of the antigen binding fragment includes the CDRs from SEQ ID NO: 2, and/or the sequence set forth as SEQ ID NO: 2. In another example, the V$_H$ amino acid sequence of the antigen binding fragment includes the CDRs from SEQ ID NO: 3 and/or the sequence set forth as one of SEQ ID NO: 3, and the V$_L$ amino acid sequence of the antigen binding fragment includes the CDRs from SEQ ID NO: 4, and/or the sequence set forth as SEQ ID NO: 4.

If the V$_H$ and the V$_L$ are expressed non-contiguously, the chains of the Fv antibody are typically held together by noncovalent interactions. However, these chains tend to dissociate upon dilution, so methods have been developed to crosslink the chains through glutaraldehyde, intermolecular disulfides, or a peptide linker. Thus, in one example, the Fv can be a disulfide stabilized Fv (dsFv), wherein the V$_H$ and the V$_L$ are chemically linked by disulfide bonds.

In an additional example, the Fv fragments include V$_H$ and V$_L$ chains connected by a peptide linker. These single-chain antigen binding proteins (scFv) can be prepared by constructing a nucleic acid molecule encoding the V$_H$ and V$_L$ domains connected by an oligonucleotide. The nucleic acid molecule is inserted into an expression vector, which is subsequently introduced into a host cell such as a mammalian cell. The recombinant host cells synthesize a single polypeptide chain with a linker peptide bridging the two V domains. Methods for producing scFvs are known in the art (see Whitlow et al., *Methods: a Companion to Methods in Enzymology*, Vol. 2, page 97, 1991; Bird et al., *Science* 242:423, 1988; U.S. Pat. No. 4,946,778; Pack et al., *Bio/Technology* 11:1271, 1993; Ahmad et al., *Clin. Dev. Immunol.*, 2012, doi: 10.1155/2012/980250; Marbry, *IDrugs*, 13:543-549, 2010). Dimers of a single chain antibody (scFV$_2$), are also contemplated.

Antigen binding fragments can be prepared by proteolytic hydrolysis of the antibody or by expression in a host cell (such as an *E. coli* cell) of DNA encoding the fragment. Antigen binding fragments can also be obtained by pepsin or papain digestion of whole antibodies by conventional methods. For example, antigen binding fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see U.S. Pat. Nos. 4,036,945 and 4,331,647, and references contained therein; Nisonhoff et al., *Arch. Biochem. Biophys.* 89:230, 1960; Porter, *Biochem. J.* 73:119, 1959; Edelman et al., *Methods in Enzymology*, Vol. 1, page 422, Academic Press, 1967; and Coligan et al. at sections 2.8.1-2.8.10 and 2.10.1-2.10.4).

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

In some embodiments, one or more (such as all) of the heavy chain and/or light chain CDRs from a disclosed antibody (such as the 4A10 or 2B8) is expressed on the surface of another protein, such as a scaffold protein. The expression of domains of antibodies on the surface of a scaffolding protein are known in the art (see e.g., Liu et al., *J. Virology* 85(17): 8467-8476, 2011). Such expression creates a chimeric protein that retains the binding for IL-7Rα. In some specific embodiments, one or more of the heavy chain CDRs is grafted onto a scaffold protein, such as one or more of heavy chain CDR1, CDR2, and/or CDR3. One or more CDRs can also be included in a diabody or another type of single chain antibody molecule.

(d) Variants

In certain embodiments, amino acid sequence variants of the antibodies provided herein are provided. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

In certain embodiments, antibody variants having one or more amino acid substitutions are provided. Sites of interest for substitutional mutagenesis include the CDRs and the framework regions. Amino acid substitutions may be introduced into an antibody of interest and the products screened for a desired activity, e.g., retained/improved antigen binding, decreased immunogenicity, or improved ADCC or CDC.

The variants typically retain amino acid residues necessary for correct folding and stabilizing between the V$_H$ and the V$_L$ regions, and will retain the charge characteristics of the residues in order to preserve the low pI and low toxicity of the molecules. Amino acid substitutions can be made in the V$_H$ and the V$_L$ regions to increase yield.

In some embodiments, the $V_H$ and $V_L$ of the antibody or antigen binding fragment each include up to 10 (such as up to 1, up to 2, up to 3, up to 4, up to 5, up to 6, up to 7, up to 8, or up to 9) amino acid substitutions (such as conservative amino acid substitutions) compared to the amino acid sequences set forth as SEQ ID NOs: 1 and 2, respectively, and the antibody or antigen binding fragment maintains specific binding activity for IL-7Rα. In some embodiments, the $V_H$ and $V_L$ of the antibody or antigen binding fragment each include up to 10 (such as up to 1, up to 2, up to 3, up to 4, up to 5, up to 6, up to 7, up to 8, or up to 9) amino acid substitutions (such as conservative amino acid substitutions) compared to the amino acid sequences set forth as SEQ ID NOs: 3 and 4, respectively, and the antibody or antigen binding fragment maintains specific binding activity for IL-7Rα.

In some embodiments, the antibody or antigen binding fragment can include up to 10 (such as up to 1, up to 2, up to 3, up to 4, up to 5, up to 6, up to 7, up to 8, or up to 9) amino acid substitutions (such as conservative amino acid substitutions) in the framework regions of the heavy chain of the antibody, or the light chain of the antibody, or the heavy and light chains of the antibody, compared to a known framework region, or compared to the framework regions of the 410 or 2B8 antibody, and maintains the specific binding activity for IL-7Rα.

In certain embodiments, substitutions, insertions, or deletions may occur within one or more CDRs so long as such alterations do not substantially reduce the ability of the antibody to bind antigen. For example, conservative alterations (e.g., conservative substitutions as provided herein) that do not substantially reduce binding affinity may be made in CDRs. In certain embodiments of the variant $V_H$ and $V_L$ sequences provided above, each CDR either is unaltered, or contains no more than one, two or three amino acid substitutions.

To increase binding affinity of the antibody, the $V_L$ and $V_H$ segments can be randomly mutated, such as within H-CDR3 region or the L-CDR3 region, in a process analogous to the in vivo somatic mutation process responsible for affinity maturation of antibodies during a natural immune response. Thus in vitro affinity maturation can be accomplished by amplifying $V_H$ and $V_L$ regions using PCR primers complementary to the H-CDR3 or L-CDR3, respectively. In this process, the primers have been "spiked" with a random mixture of the four nucleotide bases at certain positions such that the resultant PCR products encode $V_H$ and $V_L$ segments into which random mutations have been introduced into the $V_H$ and/or $V_L$ CDR3 regions. These randomly mutated $V_H$ and $V_L$ segments can be tested to determine the binding affinity for IL-7Rα. In particular examples, the $V_H$ amino acid sequence is one of SEQ ID NOs: 1 or 3. In other examples, the $V_L$ amino acid sequence is one of SEQ ID NOs: 2 or 4. Methods of in vitro affinity maturation are known (see, e.g., Chowdhury, *Methods Mol. Biol.* 207:179-196 (2008)), and Hoogenboom et al. in *Methods in Molecular Biology* 178:1-37 (O'Brien et al., ed., Human Press, Totowa, N.J., (2001)).

A useful method for identification of residues or regions of an antibody that may be targeted for mutagenesis is called "alanine scanning mutagenesis" as described by Cunningham and Wells (1989) *Science*, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex is used to identify contact points between the antibody and antigen. Such contact residues and neighboring residues may be targeted or eliminated as candidates for substitution. Variants may be screened to determine whether they contain the desired properties.

In certain embodiments, an antibody or antigen binding fragment is altered to increase or decrease the extent to which the antibody or antigen binding fragment is glycosylated. Addition or deletion of glycosylation sites may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the $CH_2$ domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region; however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lee 13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

In several embodiments, the constant region of the antibody includes one or more amino acid substitutions to optimize in vivo half-life of the antibody. The serum half-life of IgG Abs is regulated by the neonatal Fc receptor (FcRn). Thus, in several embodiments, the antibody includes an amino acid substitution that increases binding to the FcRn. Several such substitutions are known to the person of ordinary skill in the art, such as substitutions at IgG constant regions T250Q and M428L (see, e.g., Hinton et al., *J Immunol.*, 176:346-356, 2006); M428L and N434S (the "LS" mutation, see, e.g., Zalevsky, et al., *Nature Biotechnology*, 28:157-159, 2010); N434A (see, e.g., Petkova et al., *Int. Immunol.*, 18:1759-1769, 2006); T307A, E380A, and N434A (see, e.g., Petkova et al., *Int. Immunol.*, 18:1759-1769, 2006); and M252Y, S254T, and T256E (see, e.g., Dall'Acqua et al., *J. Biol. Chem.*, 281:23514-23524, 2006). The disclosed antibodies and antigen binding fragments can be linked to a Fc polypeptide including any of the substitutions listed above, for example, the Fc polypeptide can be an IgG including the M428L and N434S substitutions.

In some embodiments, the constant region of the antibody includes one of more amino acid substitutions to optimize antibody-dependent cell-mediated cytotoxicity (ADCC). ADCC is mediated primarily through a set of closely related Fcγ receptors. In some embodiments, the antibody includes one or more amino acid substitutions that increase binding to FcγRIIIa. Several such substitutions are known to the person of ordinary skill in the art, such as IgG substitutions at constant regions S239D and I332E (see, e.g., Lazar et al., *Proc. Natl., Acad. Sci. U.S.A.*, 103:4005-4010, 2006); and S239D, A330L, and I332E (see, e.g., Lazar et al., *Proc. Natl., Acad. Sci. U.S.A.*, 103:4005-4010, 2006).

Combinations of the above substitutions are also included, to generate an IgG constant region with increased binding to FcRn and FcγRIIIa. The combinations increase antibody half-life and ADCC. For example, such combination include antibodies with the following amino acid substitution in the Fc region:

(1) S239D/I332E and T250Q/M428L;
(2) S239D/I332E and M428L/N434S;
(3) S239D/I332E and N434A;
(4) S239D/I332E and T307A/E380A/N434A;
(5) S239D/I332E and M252Y/S254T/T256E;
(6) S239D/A330L/I332E and T250Q/M428L;
(7) S239D/A330L/I332E and M428L/N434S;
(8) S239D/A330L/I332E and N434A;
(9) S239D/A330L/I332E and T307A/E380A/N434A; or
(10) S239D/A330L/I332E and M252Y/S254T/T256E.

In some examples, the antibodies, or an antigen binding fragment thereof is modified such that it is directly cytotoxic to infected cells, or uses natural defenses such as complement, antibody dependent cellular cytotoxicity (ADCC), or phagocytosis by macrophages.

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

The antibody or antigen binding fragment can be derivatized or linked to another molecule (such as another peptide or protein). In general, the antibody or antigen binding fragment is derivatized such that the binding to IL-7Rα is not affected adversely by the derivatization or labeling. For example, the antibody or antigen binding fragment can be functionally linked (by chemical coupling, genetic fusion, noncovalent association or otherwise) to one or more other molecular entities, such as another antibody (for example, a bi-specific antibody or a diabody), a detectable marker, an effector molecule, or a protein or peptide that can mediate association of the antibody or antibody portion with another molecule (such as a streptavidin core region or a polyhistidine tag).

B. Conjugates

The antibodies and antigen binding fragments that specifically bind to an epitope on IL-7Rα can be conjugated to an agent, such as an effector molecule or detectable marker, using any number of means known to those of skill in the art. Both covalent and noncovalent attachment means may be used. One of skill in the art will appreciate that various effector molecules and detectable markers can be used, including (but not limited to) toxins and radioactive agents such as $^{125}$I, $^{32}$P, $^{14}$C, $^{3}$H and $^{35}$S and other labels, target moieties and ligands, etc.

The choice of a particular effector molecule or detectable marker depends on the particular target molecule or cell, and the desired biological effect. Thus, for example, the effector molecule can be a cytotoxin that is used to bring about the death of a particular target cell (such as a T-ALL cell).

The procedure for attaching an effector molecule or detectable marker to an antibody or antigen binding fragment varies according to the chemical structure of the effector. Polypeptides typically contain a variety of functional groups; such as carboxylic acid (COOH), free amine (—NH$_2$) or sulfhydryl (—SH) groups, which are available for reaction with a suitable functional group on a polypeptide to result in the binding of the effector molecule or detectable marker. Alternatively, the antibody or antigen binding fragment is derivatized to expose or attach additional reactive functional groups. The derivatization may involve attachment of any of a number of known linker molecules such as those available from Pierce Chemical Company, Rockford, IL. The linker can be any molecule used to join the antibody or antigen binding fragment to the effector molecule or detectable marker. The linker is capable of forming covalent bonds to both the antibody or antigen binding fragment and to the effector molecule or detectable marker. Suitable linkers are well known to those of skill in the art and include, but are not limited to, straight or branched-chain carbon linkers, heterocyclic carbon linkers, or peptide linkers. Where the antibody or antigen binding fragment and the effector molecule or detectable marker are polypeptides, the linkers may be joined to the constituent amino acids through their side groups (such as through a disulfide linkage to cysteine) or to the alpha carbon amino and carboxyl groups of the terminal amino acids.

In several embodiments, the linker can include a spacer element, which, when present, increases the size of the linker such that the distance between the effector molecule or the detectable marker and the antibody or antigen binding fragment is increased. Exemplary spacers are known to the person of ordinary skill, and include those listed in U.S. Pat. Nos. 7,964,667, 498,298, 6,884,869, 6,323,315, 6,239,104, 6,034,065, 5,780,588, 5,665,860, 5,663,149, 5,635,483, 5,599,902, 5,554,725, 5,530,097, 5,521,284, 5,504,191, 5,410,024, 5,138,036, 5,076,973, 4,986,988, 4,978,744, 4,879,278, 4,816,444, and 4,486,414, as well as U.S. Pat. Pub. Nos. 20110212088 and 20110070248, each of which is incorporated by reference in its entirety.

In some embodiments, the linker is cleavable under intracellular conditions, such that cleavage of the linker releases the effector molecule or detectable marker from the antibody or antigen binding fragment in the intracellular environment. In yet other embodiments, the linker is not cleavable and the effector molecule or detectable marker is released, for example, by antibody degradation. In some embodiments, the linker is cleavable by a cleaving agent that is present in the intracellular environment (for example, within a lysosome or endosome or caveolea). The linker can be, for example, a peptide linker that is cleaved by an intracellular peptidase or protease enzyme, including, but not limited to, a lysosomal or endosomal protease. In some embodiments, the peptide linker is at least two amino acids long or at least three amino acids long. However, the linker can be 4, 5, 6, 7, 8, 9, 10, 11, 12, 13, 14 or 15 amino acids long, such as 1-2, 1-3, 2-5, 3-10, 3-15, 1-5, 1-10, 1-15, amino acids long. Proteases can include cathepsins B and D and plasmin, all of which are known to hydrolyze dipeptide drug derivatives resulting in the release of active drug inside target cells (see, for example, Dubowchik and Walker, 1999, Pharm. Therapeutics 83:67-123). For example, a peptide linker that is cleavable by the thiol-dependent protease cathepsin-B, can be used (for example, a Phenylalanine-Leucine or a Glycine-Phenylalanine-Leucine-Glycine linker). Other examples of such linkers are described, for example, in U.S. Pat. No. 6,214,345, incorporated herein by reference. In a specific embodiment, the peptide linker cleavable by an intracellular protease is a Valine-Citruline linker or a Phenylalanine-Lysine linker (see, for example, U.S. Pat. No. 6,214,345, which describes the synthesis of doxorubicin with the Valine-Citruline linker).

In other embodiments, the cleavable linker is pH-sensitive, i.e., sensitive to hydrolysis at certain pH values. Typically, the pH-sensitive linker is hydrolyzable under acidic conditions. For example, an acid-labile linker that is hydrolyzable in the lysosome (for example, a hydrazone, semicarbazone, thiosemicarbazone, cis-aconitic amide, orthoester, acetal, ketal, or the like) can be used. (See, for example, U.S. Pat. Nos. 5,122,368; 5,824,805; 5,622,929; Dubowchik and Walker, 1999, Pharm. Therapeutics 83:67-123; Neville et al., 1989, Biol. Chem. 264:14653-14661.) Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, for example, a thioether attached to the therapeutic agent via an acylhydrazone bond (see, for example, U.S. Pat. No. 5,622,929).

In yet other embodiments, the linker is cleavable under reducing conditions (for example, a disulfide linker). A variety of disulfide linkers are known in the art, including, for example, those that can be formed using SATA (N-succinimidyl-S-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio) toluene)-, SPDB and SMPT. (See, for example, Thorpe et al., 1987, Cancer Res. 47:5924-5931; Wawrzynczak et al., In Immunoconjugates: Antibody Conjugates in Radioimagery and Therapy of Cancer (C. W. Vogel ed., Oxford U. Press, 1987); Phillips et al., Cancer Res. 68:92809290, 2008). See also U.S. Pat. No. 4,880,935.)

In yet other specific embodiments, the linker is a malonate linker (Johnson et al., 1995, Anticancer Res. 15:1387-93), a maleimidobenzoyl linker (Lau et al., 1995, Bioorg-Med-Chem. 3(10):1299-1304), or a 3'-N-amide analog (Lau et al., 1995, Bioorg-Med-Chem. 3(10):1305-12).

In several embodiments, the linker is resistant to cleavage in an extracellular environment. Whether or not a linker is resistant to cleavage in an extracellular environment can be determined, for example, by incubating the conjugate containing the linker of interest with plasma for a predetermined time period (for example, 2, 4, 8, 16, or 24 hours) and then quantitating the amount of free effector molecule or detectable marker present in the plasma. A variety of exemplary linkers that can be used in conjugates are described in WO 2004010957, U.S. Publication No. 2006/0074008, U.S. Publication No. 20050238649, and U.S. Publication No. 2006/0024317, each of which is incorporated by reference herein in its entirety.

In view of the large number of methods that have been reported for attaching a variety of radiodiagnostic compounds, radiotherapeutic compounds, labels (such as enzymes or fluorescent molecules), toxins, and other agents to antibodies one skilled in the art will be able to determine a suitable method for attaching a given agent to an antibody or antigen binding fragment or other polypeptide. For example, the antibody or antigen binding fragment can be conjugated with effector molecules such as small molecular weight drugs such as Monomethyl Auristatin E (MMAE), Monomethyl Auristatin F (MMAF), maytansine, maytansine derivatives, including the derivative of maytansine known as DM1 (also known as mertansine), or other agents to make an antibody drug conjugate (ADC). In several embodiments, conjugates of an antibody or antigen binding fragment and one or more small molecule toxins, such as a calicheamicin, maytansinoids, dolastatins, auristatins, a trichothecene, and CC1065, and the derivatives of these toxins that have toxin activity, are provided.

The antibody or antigen binding fragment can be conjugated with a detectable marker; for example, a detectable marker capable of detection by ELISA, spectrophotometry, flow cytometry, microscopy or diagnostic imaging techniques (such as computed tomography (CT), computed axial tomography (CAT) scans, magnetic resonance imaging (MRI), nuclear magnetic resonance imaging NMRI), magnetic resonance tomography (MTR), ultrasound, fiberoptic examination, and laparoscopic examination). Specific, non-limiting examples of detectable markers include fluorophores, chemiluminescent agents, enzymatic linkages, radioactive isotopes and heavy metals or compounds (for example super paramagnetic iron oxide nanocrystals for detection by MRI). For example, useful detectable markers include fluorescent compounds, including fluorescein, fluorescein isothiocyanate, rhodamine, 5-dimethylamine-1-napthalenesulfonyl chloride, phycoerythrin, lanthanide phosphors and the like. Bioluminescent markers are also of use, such as luciferase, Green fluorescent protein (GFP), Yellow fluorescent protein (YFP). An antibody or antigen binding fragment can also be conjugated with enzymes that are useful for detection, such as horseradish peroxidase, β-galactosidase, luciferase, alkaline phosphatase, glucose oxidase and the like. When an antibody or antigen binding fragment is conjugated with a detectable enzyme, it can be detected by adding additional reagents that the enzyme uses to produce a reaction product that can be discerned. For example, when the agent horseradish peroxidase is present the addition of hydrogen peroxide and diaminobenzidine leads to a colored reaction product, which is visually detectable. An antibody or antigen binding fragment may also be conjugated with biotin, and detected through indirect measurement of avidin or streptavidin binding. It should be noted that the avidin itself can be conjugated with an enzyme or a fluorescent label.

The antibody or antigen binding fragment can be conjugated with a paramagnetic agent, such as gadolinium. Paramagnetic agents such as superparamagnetic iron oxide are also of use as labels. Antibodies can also be conjugated with lanthanides (such as europium and dysprosium), and manganese. An antibody or antigen binding fragment may also be labeled with a predetermined polypeptide epitopes recognized by a secondary reporter (such as leucine zipper pair sequences, binding sites for secondary antibodies, metal binding domains, epitope tags).

The antibody or antigen binding fragment can also be conjugated with a radiolabeled amino acid. The radiolabel may be used for both diagnostic and therapeutic purposes. For instance, the radiolabel may be used to detect IL-7Rα and IL-7Rα expressing cells by x-ray, emission spectra, or other diagnostic techniques. Examples of labels for polypeptides include, but are not limited to, the following radioisotopes or radionucleotides: $^{3}$H, $^{14}$C, $^{15}$N, $^{35}$S, $^{90}$Y $^{99}$Tc, $^{111}$n, $^{125}$I, $^{131}$I.

Means of detecting such detectable markers are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

The average number of effector molecule or detectable marker moieties per antibody or antigen binding fragment in a conjugate can range, for example, from 1 to 20 moieties per antibody or antigen binding fragment. In certain embodiments, the average number of effector molecule or detectable marker moieties per antibody or antigen binding fragment in a conjugate range from about 1 to about 2, from about 1 to about 3, about 1 to about 8; from about 2 to about 6; from about 3 to about 5; or from about 3 to about 4. The loading (for example, effector molecule/antibody ratio) of an conjugate may be controlled in different ways, for example, by: (i) limiting the molar excess of effector molecule-linker intermediate or linker reagent relative to antibody, (ii) limiting the conjugation reaction time or temperature, (iii) partial or limiting reductive conditions for cysteine thiol modification, (iv) engineering by recombinant techniques the amino acid sequence of the antibody such that the number and position of cysteine residues is modified for control of the number or position of linker-effector molecule attachments.

C. Chimeric Antigen Receptors (CARs)

Also disclosed herein are chimeric antigen receptor (CARs) that are artificially constructed chimeric proteins including an extracellular antigen binding domain (e.g., single chain variable fragment (scFv)) that specifically binds to IL-7Rα, linked to a transmembrane domain, linked to one or more intracellular T cell signaling domains. Characteristics of the disclosed CARs include their ability to redirect T cell specificity and reactivity towards IL-7Rα expressing cells in a non-MHC-restricted manner. The non-MHC-restricted IL-7Rα recognition gives T cells expressing a disclosed CAR the ability to recognize antigen independent of antigen processing.

The intracellular T cell signaling domains can include, for example, a T cell receptor signaling domain, a T cell costimulatory signaling domain, or both. The T cell receptor signaling domain refers to a portion of the CAR comprising the intracellular domain of a T cell receptor, such as the intracellular portion of the CD3 zeta protein. The costimulatory signaling domain refers to a portion of the CAR comprising the intracellular domain of a costimulatory molecule, which is a cell surface molecule other than an antigen receptor or their ligands that are required for an efficient response of lymphocytes to antigen.

1. Extracellular Region

Several embodiments provide a CAR including an antigen binding domain that specifically binds to IL-7Rα as disclosed herein (see, e.g., section III.A). For example, the antigen binding domain can be a scFv including the $V_H$ and the $V_L$ of any of the 4A10 or 2B8 antibody, or a humanized or chimeric version thereof. In some embodiment, the antigen binding domain can include a $V_H$ and a $V_L$ including the HCDR1, HCDR2, HCDR3, LCDR1, LCDR2, and LCDR3 of the $V_H$ and $V_L$, respectively, of the 4A10 or the 2B8 antibody (e.g., as set forth in Table 1).

In some embodiments, the antigen binding domain includes a $V_H$ and a $V_L$ including the amino acid sequences set forth as SEQ ID NOs: 1 and 2, respectively; or SEQ ID NOs: 3 and 4, respectively. In several embodiments, the antigen binding domain can be a scFv. In some embodiments, the scFv includes a $V_H$ and a $V_L$ joined by a peptide linker, such as a linker including the amino acid sequence set forth as GGGGSGGGGSGGGGS (SEQ ID NO: 37).

The CAR can include a signal peptide sequence, e.g., N-terminal to the antigen binding domain. The signal peptide sequence may comprise any suitable signal peptide sequence. In an embodiment, the signal peptide sequence is a human granulocyte-macrophage colony-stimulating factor (GM-CSF) receptor sequence, such as an amino acid sequence including or consisting of LLVTSLLLCEL-PHPAFLLIPDT (SEQ ID NO: 38). While the signal peptide sequence may facilitate expression of the CAR on the surface of the cell, the presence of the signal peptide sequence in an expressed CAR is not necessary in order for the CAR to function. Upon expression of the CAR on the cell surface, the signal peptide sequence may be cleaved off of the CAR. Accordingly, in some embodiments, the CAR lacks a signal peptide sequence.

Between the antigen binding domain and the transmembrane domain of the CAR, there may be a spacer domain, which includes a polypeptide sequence. The spacer domain may comprise up to 300 amino acids, preferably 10 to 100 amino acids and most preferably 25 to 50 amino acids. In some embodiments, the spacer domain can include an immunoglobulin domain, such as a human immunoglobulin sequence. In an embodiment, the immunoglobulin domain comprises an immunoglobulin CH2 and CH3 immunoglobulin G (IgG1) domain sequence (CH2CH3). In this regard, the spacer domain can include an immunoglobulin domain comprising or consisting of the amino acid sequence set forth as SEQ ID NO: 39:

EPKSCDKTHTCPPCPAPELLGGPSVFLFPPKPKDTLMISRTPEVTCVVVDV

SHEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTCL

VKGFYPSDIAVEWESNGQPENNYKTTPPVLDSDGSFFLYSKLTVDKSRWQQ

GNVFSCSVMHEALHNHYTQKSLSLSPGKKDPK

Without being bound to a particular theory, it is believed that the CH2CH3 domain extends the antigen binding domain of the CAR away from the membrane of CAR-expressing cells and may more accurately mimic the size and domain structure of a native TCR.

2. Transmembrane Domain

With respect to the transmembrane domain, the CAR can be designed to comprise a transmembrane domain that is fused to the extracellular domain of the CAR. In one embodiment, the transmembrane domain that naturally is associated with one of the domains in the CAR is used.

The transmembrane domain may be derived either from a natural or from a synthetic source. Where the source is natural, the domain may be derived from any membrane-bound or transmembrane protein. Exemplary transmembrane domains for use in the disclosed CARs can include at least the transmembrane region(s) of) the alpha, beta or zeta chain of the T cell receptor, CD28, CD3 epsilon, CD45, CD4, CD5, CD8, CD9, CD 16, CD22, CD33, CD37, CD64, CD80, CD86, CD 134, CD137, CD154. Alternatively the transmembrane domain may be synthetic, in which case it will comprise predominantly hydrophobic residues such as leucine and valine. In several embodiments, a triplet of phenylalanine, tryptophan and valine will be found at each end of a synthetic transmembrane domain.

Optionally, a short oligo- or polypeptide linker, preferably between 2 and 10 amino acids in length may form the linkage between the transmembrane domain and the intracellular T cell signaling domain and/or T cell costimulatory domain of the CAR. An exemplary linker sequence includes one or more glycine-serine doublets.

In some embodiments, the transmembrane domain comprises the transmembrane domain of a T cell receptor, such as a CD8 transmembrane domain. Thus, the CAR can include a CD8 transmembrane domain including or consisting of SEQ ID NO: 40: TTTPAPRPPTPAPTIASQPLSLRPE ACRPAAGGAVHTRGLDFACDIYIWAPLAGTCGVLLLSLVITLYC In another embodiment, the transmembrane domain comprises the transmembrane domain of a T cell costimulatory molecule, such as CD137 or CD28. Thus, the CAR can include a CD28 transmembrane domain including or consisting of SEQ ID NO: 41: IEVMYPPPYLDNEKSNGTIIHVKGK HLCPSPLFPGPSKPFWVLVVVGGVLACYSLLVTVAFIIFWVR 3. Intracellular Region The intracellular region of the CAR includes one or more intracellular T cell signaling domains responsible for activation of at least one of the normal effector functions of a T cell in which the CAR is expressed or placed in. Exemplary T cell signaling domains are provided herein, and are known to the person of ordinary skill in the art.

While an entire intracellular T cell signaling domain can be employed in a CAR, in many cases it is not necessary to use the entire chain. To the extent that a truncated portion of the intracellular T cell signaling domain is used, such truncated portion may be used in place of the intact chain as long as it transduces the relevant T cell effector function signal.

Examples of intracellular T cell signaling domains for use in the CAR include the cytoplasmic sequences of the T cell receptor (TCR) and co-stimulatory molecules that act in concert to initiate signal transduction following antigen receptor engagement, as well as any derivative or variant of these sequences and any synthetic sequence that has the same functional capability.

T cell receptor signaling domains regulate primary activation of the T cell receptor complex either in a stimulatory way, or in an inhibitory way. The disclosed CARs can include primary cytoplasmic signaling sequences that act in a stimulatory manner, which may contain signaling motifs that are known as immunoreceptor tyrosine-based activation motifs or ITAMs. Examples of ITAM containing primary cytoplasmic signaling sequences that can be included in a disclosed CAR include those from CD3 zeta, FcR gamma, FcR beta, CD3 gamma, CD3 delta, CD3 epsilon, CDS, CD22, CD79a, CD79b, and CD66d proteins. In several embodiments, the cytoplasmic signaling molecule in the CAR includes an intracellular T cell signaling domain from CD3 zeta.

The intracellular region of the CAR can include the ITAM containing primary cytoplasmic signaling domain (such as CD3-zeta) by itself or combined with any other desired cytoplasmic domain(s) useful in the context of a CAR. For example, the cytoplasmic domain of the CAR can include a CD3 zeta chain portion and an intracellular costimulatory signaling domain. The costimulatory signaling domain refers to a portion of the CAR comprising the intracellular domain of a costimulatory molecule. A costimulatory molecule is a cell surface molecule other than an antigen receptor or their ligands that is required for an efficient response of lymphocytes to an antigen. Examples of such molecules include CD27, CD28, 4-1BB (CD137), OX40 (CD134), CD30, CD40, PD-1, ICOS, lymphocyte function-associated antigen 1 (LFA-1), CD2, CD7, LIGHT, NKG2C, and B7-H3. An additional example of a signaling domain that can be included in a disclosed CARs is a Tumor necrosis factor receptor superfamily member 18 (TNFRSF18; also known as glucocorticoid-induced TNFR-related protein, GITR) signaling domain.

In some embodiments, the CAR can include a CD3 zeta signaling domain, a CD8 signaling domain, a CD28 signaling domain, a CD137 signaling domain or a combination of two or more thereof. In one embodiment, the cytoplasmic domain includes the signaling domain of CD3-zeta and the signaling domain of CD28. In another embodiment, the cytoplasmic domain includes the signaling domain of CD3 zeta and the signaling domain of CD137. In yet another embodiment, the cytoplasmic domain includes the signaling domain of CD3-zeta and the signaling domain of CD28 and CD137. The order of the one or more T cell signaling domains on the CAR can be varied as needed by the person of ordinary skill in the art.

Exemplary amino acid sequences for such T cell signaling domains are provided. For example, the CD3 zeta signaling domain can include or consist of the amino acid sequence set forth as SEQ ID NO: 42 (RVKFSRSADAPA-YQQGQNQLYNELNLGRREEYDVLDKRR-GRDPEMGGKPRRKNPQEG LYNELQKDKMAEAYSEI-GMKGERRRGKGHDGLYQGLSTATKDTYDALHMQALP-PR), the CD8 signaling domain can include or consist of the amino acid sequence set forth as SEQ ID NO: 43 (FVPVFL-PAKPTTTPAPRPPTPAPTIASQPLSLRPEACR-PAAGGAVHTRGLDFACDIYIWAP LAGTCGVLLLSLVITLYCNHRNR), the CD28 signaling domain can include or consist of the amino acid sequence set forth as SEQ ID NO: 44 (SKRSRLLHSDYMNMT-PRRPGPTRKHYQPYA PPRDFAAYRS), the CD137 signaling domain can include or consist of the amino acid sequences set forth as SEQ ID NO: 45 (KRGRKKLLY-IFKQPFMRPVQTTQEEDGCSCRFPEEEEGGC EL) or SEQ ID NO: 46 (RFSVVKRGRKKLLY-IFKQPFMRPVQTTQEEDGCSCRFPEEEEGGCEL).

The cytoplasmic signaling sequences within the cytoplasmic signaling portion of the CAR of the invention may be linked to each other in a random or specified order. Optionally, a short polypeptide linker, preferably between 2 and 10 amino acids in length may form the linkage. A glycine-serine doublet provides a particularly suitable linker. Further, between the signaling domain and the transmembrane domain of the CAR, there may be a spacer domain, which includes a polypeptide sequence. The spacer domain may comprise up to 300 amino acids, preferably 10 to 100 amino acids and most preferably 25 to 50 amino acids.

4. Additional Description of CARs

Also provided are functional portions of the CARs described herein. The term "functional portion" when used in reference to a CAR refers to any part or fragment of the CAR, which part or fragment retains the biological activity of the CAR of which it is a part (the parent CAR). Functional portions encompass, for example, those parts of a CAR that retain the ability to recognize target cells, or detect, treat, or prevent a disease, to a similar extent, the same extent, or to a higher extent, as the parent CAR. In reference to the parent CAR, the functional portion can comprise, for instance, about 10%, 25%, 30%, 50%, 68%, 80%, 90%, 95%, or more, of the parent CAR.

The CAR or functional portion thereof, can include additional amino acids at the amino or carboxy terminus, or at both termini, which additional amino acids are not found in the amino acid sequence of the parent CAR. Desirably, the additional amino acids do not interfere with the biological function of the CAR or functional portion, e.g., recognize target cells, detect cancer, treat or prevent cancer, etc. More desirably, the additional amino acids enhance the biological activity, as compared to the biological activity of the parent CAR.

Also provided are functional variants of the CARs described herein, which have substantial or significant sequence identity or similarity to a parent CAR, which functional variant retains the biological activity of the CAR of which it is a variant. Functional variants encompass, for example, those variants of the CAR described herein (the parent CAR) that retain the ability to recognize target cells to a similar extent, the same extent, or to a higher extent, as the parent CAR. In reference to the parent CAR, the functional variant can, for instance, be at least about 30%, about 50%, about 75%, about 80%, about 85%, about 90%, about 91%, about 92%, about 93%, about 94%, about 95%, about 96%), about 97%, about 98%, about 99% or more identical in amino acid sequence to the parent CAR.

A functional variant can, for example, comprise the amino acid sequence of the parent CAR with at least one conservative amino acid substitution. Alternatively or additionally, the functional variants can comprise the amino acid sequence of the parent CAR with at least one non-conservative amino acid substitution. In this case, it is preferable for the non-conservative amino acid substitution to not interfere with or inhibit the biological activity of the functional variant. The non-conservative amino acid substitution may enhance the biological activity of the functional variant, such that the biological activity of the functional variant is increased as compared to the parent CAR.

The CARs (including functional portions and functional variants) can be of any length, i.e., can comprise any number of amino acids, provided that the CARs (or functional portions or functional variants thereof) retain their biological activity, e.g., the ability to specifically bind to antigen, detect diseased cells in a mammal, or treat or prevent disease in a mammal, etc. For example, the CAR can be about 50 to about 5000 amino acids long, such as 50, 70, 75, 100, 125, 150, 175, 200, 300, 400, 500, 600, 700, 800, 900, 1000 or more amino acids in length.

The CARs (including functional portions and functional variants of the invention) can comprise synthetic amino acids in place of one or more naturally-occurring amino acids. Such synthetic amino acids are known in the art, and include, for example, aminocyclohexane carboxylic acid, norleucine, a-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, oc-aminocycloheptane carboxylic acid, -(2-amino-2-norbomane)-carboxylic acid, γ-diaminobutyric acid, α,β-diaminopropionic acid, homophenylalanine, and α-tert-butylglycine.

The CARs (including functional portions and functional variants) can be glycosylated, amidated, carboxylated, phosphorylated, esterified, N-acylated, cyclized via, e.g., a disulfide bridge, or converted into an acid addition salt and/or optionally dimerized or polymerized, or conjugated.

Methods of generating chimeric antigen receptors, T cells including such receptors, and their use (e.g., for treatment of cancer) are known in the art and further described herein (see, e.g., Brentjens et al., 2010, Molecular Therapy, 18:4, 666-668; Morgan et al., 2010, Molecular Therapy, published online Feb. 23, 2010, pages 1-9; Till et al., 2008, Blood, 1 12:2261-2271; Park et al., *Trends Biotechnol.,* 29:550-557, 2011; Grupp et al., N Engl J Med., 368:1509-1518, 2013; Han et al., J. Hematol Oncol., 6:47, 2013; PCT Pub. WO2012/079000, WO2013/126726; and U.S. Pub. 2012/0213783, each of which is incorporated by reference herein in its entirety.) For example, a nucleic acid molecule encoding a disclosed chimeric antigen binding receptor can be included in an expression vector (such as a lentiviral vector) for expression in a host cell, such as a T cell, to make the disclosed CAR. In some embodiments, methods of using the chimeric antigen receptor include isolating T cells from a subject, transforming the T cells with an expression vector (such as a lentiviral vector) encoding the chimeric antigen receptor, and administering the engineered T cells expressing the chimeric antigen receptor to the subject for treatment, for example for treatment of a IL-7Rα-positive cancer in the subject.

D. Polynucleotides and Expression

Nucleic acids molecules (for example, cDNA molecules) encoding the amino acid sequences of antibodies, antibody binding fragments, CARs and conjugates that specifically bind IL-7Rα are provided. Nucleic acids encoding these molecules can readily be produced by one of skill in the art, using the amino acid sequences provided herein (such as the CDR sequences and $V_H$ and $V_L$ sequences), sequences available in the art (such as framework or constant region sequences), and the genetic code. In several embodiments, a nucleic acid molecules can encode the $V_H$, the $V_L$, or both the $V_H$ and $V_L$ (for example in a bicistronic expression vector) of a disclosed antibody or antigen binding fragment, or a humanized version thereof. In several embodiments, the nucleic acid molecules can be expressed in a host cell (such as a mammalian cell) to produce a disclosed antibody or antigen binding fragment.

One of skill in the art can readily use the genetic code to construct a variety of functionally equivalent nucleic acids, such as nucleic acids which differ in sequence but which encode the same antibody sequence, or encode a conjugate or fusion protein including the $V_L$ and/or $V_H$ nucleic acid sequence.

In a non-limiting example, an isolated nucleic acid molecule encodes the $V_H$ of a disclosed antibody or antigen binding fragment and includes the nucleic acid sequence set forth as any one of SEQ ID NOs: 25 or 27. In a non-limiting example, an isolated nucleic acid molecule encodes the $V_L$ of a disclosed antibody or antigen binding fragment and includes the nucleic acid sequence set forth as any one of SEQ ID NOs: 26 or 28. In a non-limiting example, an isolated nucleic acid molecule encodes the $V_H$ and $V_L$ of a disclosed antibody or antigen binding fragment and includes the nucleic acid sequences set forth as any one of SEQ ID NOs: 25 and 26, respectively, or 27 and 28, respectively.

Nucleic acid sequences encoding the antibodies, antibody binding fragments, CARs and conjugates that specifically bind IL-7Rα can be prepared by any suitable method including, for example, cloning of appropriate sequences or by direct chemical synthesis by methods such as the phosphotriester method of Narang et al., *Meth. Enzymol.* 68:90-99, 1979; the phosphodiester method of Brown et al., *Meth. Enzymol.* 68:109-151, 1979; the diethylphosphoramidite method of Beaucage et al., *Tetra. Lett.* 22:1859-1862, 1981; the solid phase phosphoramidite triester method described by Beaucage & Caruthers, *Tetra. Letts.* 22(20):1859-1862, 1981, for example, using an automated synthesizer as described in, for example, Needham-VanDevanter et al., *Nucl. Acids Res.* 12:6159-6168, 1984; and, the solid support method of U.S. Pat. No. 4,458,066. Chemical synthesis produces a single stranded oligonucleotide. This can be converted into double stranded DNA by hybridization with a complementary sequence or by polymerization with a DNA polymerase using the single strand as a template.

Exemplary nucleic acids can be prepared by cloning techniques. Examples of appropriate cloning and sequencing techniques, and instructions sufficient to direct persons of skill through many cloning exercises are known (see, e.g, Sambrook et al. (Molecular Cloning: A Laboratory Manual, 4$^{th}$ ed, Cold Spring Harbor, New York, 2012) and Ausubel et al. (In Current Protocols in Molecular Biology, John Wiley & Sons, New York, through supplement 104, 2013). Product information from manufacturers of biological reagents and experimental equipment also provide useful information. Such manufacturers include the SIGMA Chemical Company (Saint Louis, MO), R&D Systems (Minneapolis, MN), Pharmacia Amersham (Piscataway, NJ), CLONTECH Laboratories, Inc. (Palo Alto, CA), Chem Genes Corp., Aldrich Chemical Company (Milwaukee, WI), Glen Research, Inc., GIBCO BRL Life Technologies, Inc. (Gaithersburg, MD), Fluka Chemica-Biochemika Analytika (Fluka Chemie AG, Buchs, Switzerland), Invitrogen (Carlsbad, CA), and Applied Biosystems (Foster City, CA), as well as many other commercial sources known to one of skill.

Nucleic acids can also be prepared by amplification methods. Amplification methods include polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

In some embodiments, the nucleic acid molecule encodes a CAR as provided herein for expression in a T cell to generate a chimeric antigen receptor T cell. The nucleic acid molecule encoding the chimeric antigen binding receptor can be included in a vector (such as a lentiviral vector) for expression in a host cell, such as a T cell. Exemplary cells include a T cell, a Natural Killer (NK) cell, a cytotoxic T lymphocyte (CTL), and a regulatory T cell. Methods of generating nucleic acid molecules encoding chimeric antigen receptors and T cells including such receptors are known in the art (see, e.g., Brentjens et al., 2010, Molecular Therapy, 18:4, 666-668; Morgan et al., 2010, Molecular Therapy, published online Feb. 23, 2010, pages 1-9; Till et al., 2008, Blood, 1 12:2261-2271; Park et al., *Trends Biotechnol.*, 29:550-557, 2011; Grupp et al., N Engl J Med., 368:1509-1518, 2013; Han et al., J. Hematol Oncol., 6:47, 2013; PCT Pub. WO2012/079000, WO2013/126726; and U.S. Pub. 2012/0213783, each of which is incorporated by reference herein in its entirety.)

The nucleic acid molecules can be expressed in a recombinantly engineered cell such as bacteria, plant, yeast, insect and mammalian cells. The antibodies, antigen binding fragments, and conjugates can be expressed as individual $V_H$ and/or $V_L$ chain (linked to an effector molecule or detectable marker as needed), or can be expressed as a fusion protein. Methods of expressing and purifying antibodies and antigen binding fragments are known and further described herein (see, e.g., Al-Rubeai (ed), *Antibody Expression and Production*, Springer Press, 2011). An immunoadhesin can also be expressed. Thus, in some examples, nucleic acids encoding a $V_H$ and $V_L$, and immunoadhesin are provided. The nucleic acid sequences can optionally encode a leader sequence.

To create a scFv the $V_H$- and $V_L$-encoding DNA fragments can be operatively linked to another fragment encoding a flexible linker, e.g., encoding the amino acid sequence (Gly$_4$-Ser)$_3$, such that the $V_H$ and $V_L$ sequences can be expressed as a contiguous single-chain protein, with the $V_L$ and $V_H$ domains joined by the flexible linker (see, e.g., Bird et al., *Science* 242:423-426, 1988; Huston et al., *Proc. Natl. Acad. Sci. USA* 85:5879-5883, 1988; McCafferty et al., *Nature* 348:552-554, 1990; Kontermann and Dubel (Ed), Antibody Engineering, Vols. 1-2, 2$^{nd}$ Ed., Springer Press, 2010; Harlow and Lane, *Antibodies: A Laboratory Manual*, $2^{nd}$, Cold Spring Harbor Laboratory, New York, 2013,). Optionally, a cleavage site can be included in a linker, such as a furin cleavage site.

The single chain antibody may be monovalent, if only a single $V_H$ and $V_L$ are used, bivalent, if two $V_H$ and $V_L$ are used, or polyvalent, if more than two $V_H$ and $V_L$ are used. Bispecific or polyvalent antibodies may be generated that bind specifically to IL-7Rα and another antigen, such as, but not limited to CD3. The encoded $V_H$ and $V_L$ optionally can include a furin cleavage site between the $V_H$ and $V_L$ domains.

The nucleic acid encoding a $V_H$ and/or the $V_L$ optionally can encode an Fc domain (immunoadhesin). The Fc domain can be an IgA, IgM or IgG Fc domain. The Fc domain can be an optimized Fc domain, as described in U.S. Published Patent Application No. 20100/093979, incorporated herein by reference. In one example, the immunoadhesin is an $IgG_1$ Fc.

Those of skill in the art are knowledgeable in the numerous expression systems available for expression of proteins including E. coli, other bacterial hosts, yeast, and various higher eukaryotic cells such as the COS, CHO, HeLa and myeloma cell lines.

One or more DNA sequences encoding the antibodies, antibody binding fragments, CARs or conjugates can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art. Hybridomas expressing the antibodies of interest are also encompassed by this disclosure.

The expression of nucleic acids encoding the antibodies and antigen binding fragments described herein can be achieved by operably linking the DNA or cDNA to a promoter (which is either constitutive or inducible), followed by incorporation into an expression cassette. The promoter can be any promoter of interest, including a cytomegalovirus promoter and a human T cell lymphotrophic virus promoter (HTLV)-1. Optionally, an enhancer, such as a cytomegalovirus enhancer, is included in the construct. The cassettes can be suitable for replication and integration in either prokaryotes or eukaryotes. Typical expression cassettes contain specific sequences useful for regulation of the expression of the DNA encoding the protein. For example, the expression cassettes can include appropriate promoters, enhancers, transcription and translation terminators, initiation sequences, a start codon (i.e., ATG) in front of a protein-encoding gene, splicing signal for introns, sequences for the maintenance of the correct reading frame of that gene to permit proper translation of mRNA, and stop codons. The vector can encode a selectable marker, such as a marker encoding drug resistance (for example, ampicillin or tetracycline resistance).

To obtain high level expression of a cloned gene, it is desirable to construct expression cassettes which contain, at the minimum, a strong promoter to direct transcription, a ribosome binding site for translational initiation (internal ribosomal binding sequences), and a transcription/translation terminator. For E. coli, this can include a promoter such as the T7, trp, lac, or lambda promoters, a ribosome binding site, and preferably a transcription termination signal. For eukaryotic cells, the control sequences can include a promoter and/or an enhancer derived from, for example, an immunoglobulin gene, HTLV, SV40 or cytomegalovirus, and a polyadenylation sequence, and can further include splice donor and/or acceptor sequences (for example, CMV and/or HTLV splice acceptor and donor sequences). The cassettes can be transferred into the chosen host cell by well-known methods such as transformation or electroporation for E. coli and calcium phosphate treatment, electroporation or lipofection for mammalian cells. Cells transformed by the cassettes can be selected by resistance to antibiotics conferred by genes contained in the cassettes, such as the amp, gpt, neo and hyg genes.

When the host is a eukaryote, such methods of transfection of DNA as calcium phosphate coprecipitates, conventional mechanical procedures such as microinjection, electroporation, insertion of a plasmid encased in liposomes, or virus vectors may be used. Eukaryotic cells can also be cotransformed with polynucleotide sequences encoding the antibody, labeled antibody, or antigen biding fragment, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, Viral Expression Vectors, Springer press, Muzyczka ed., 2011). One of skill in the art can readily use an expression systems such as plasmids and vectors of use in producing proteins in cells including higher eukaryotic cells such as the COS, CHO, HeLa and myeloma cell lines.

For purposes of producing a recombinant CAR, the host cell may be a mammalian cell. The host cell may be a human cell. In some embodiments, the host cell may be a peripheral blood lymphocyte (PBL) or a peripheral blood mononuclear cell (PBMC), or a T cell. The T cell can be any T cell, such as a cultured T cell, e.g., a primary T cell, or a T cell from a cultured T cell line, e.g., Jurkat, SupTl, etc., or a T cell obtained from a mammal (such as a human patient to which the CAR-T cell will later be administered). If obtained from a mammal, the T cell can be obtained from numerous sources, including but not limited to blood, bone marrow, lymph node, the thymus, or other tissues or fluids. T cells can also be enriched for or purified. The T cell may be a human T cell. The T cell may be a T cell isolated from a human. The T cell can be any type of T cell and can be of any developmental stage, including but not limited to, $CD4^+/CD8^+$ double positive T cells, $CD4^+$ helper T cells, e.g., $Th_1$ and $Th_2$ cells, $CD8^+$ T cells (e.g., cytotoxic T cells), tumor infiltrating cells, memory T cells, naive T cells, and the like. The T cell may be a $CD8^+$ T cell or a $CD4^+$ T cell.

Also provided is a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cell, a muscle cell, a brain cell, etc. Alternatively, the population of cells can be a substantially homogeneous population, in which the population comprises mainly host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein Modifications can be made to a nucleic acid encoding a polypeptide described herein without diminishing its biological activity. Some modifications can be made to facilitate the cloning, expression, or incorporation of the targeting molecule into a fusion protein. Such modifications are well known to those of skill in the art and include, for example, termination codons, a methionine added at the amino terminus to provide an initiation, site, additional amino acids placed on either terminus to create conveniently located restriction sites, or additional amino acids (such as poly His) to aid in purification steps. In addition to recombinant methods, the immunoconjugates, effector moieties, and antibodies of the present disclosure can also be constructed in whole or in part using standard peptide synthesis well known in the art.

Once expressed, the antibodies, antigen binding fragments, and conjugates can be purified according to standard procedures in the art, including ammonium sulfate precipitation, affinity columns, column chromatography, and the like (see, generally, Simpson ed., Basic methods in Protein Purification and Analysis: A laboratory Manual, Cold Harbor Press, 2008). The antibodies, antigen binding fragment, and conjugates need not be 100% pure. Once purified, partially or to homogeneity as desired, if to be used therapeutically, the polypeptides should be substantially free of endotoxin.

Methods for expression of the antibodies, antigen binding fragments, and conjugates, and/or refolding to an appropriate active form, from mammalian cells, and bacteria such as E. coli have been described and are well-known and are applicable to the antibodies disclosed herein. See, e.g., Harlow and Lane, *Antibodies: A Laboratory Manual*, $2^{nd}$, Cold Spring Harbor Laboratory, New York, 2013, Simpson ed., Basic methods in Protein Purification and Analysis: A laboratory Manual, Cold Harbor Press, 2008, and Ward et al., *Nature* 341:544, 1989.

E. Methods and Compositions
1. Therapeutic Methods
Cancer

The IL-7Rα-specific antibodies, antigen binding fragments, conjugates, and CAR T cells disclosed herein can be administered a subject to slow or inhibit the growth of cancer cells expressing IL-7Rα, such as proliferating T or B cells. In these applications, an IL-7Rα-specific antibody, antigen binding fragment, conjugate, or CAR T cell as disclosed herein is administered to a subject in an amount sufficient to inhibit growth, replication, or metastasis of the cancer cells expressing IL-7Rα, or to inhibit a sign or a symptom of the cancer. Suitable subjects include those diagnosed with an IL-7Rα-positive cancer (that is, a cancer including cells that expresses IL-7Rα protein), such as, but not limited to, ALL, for example, T-ALL or B-ALL.

In one non-limiting embodiment, provided herein is a method of treating a subject with an IL-7R-positive cancer by selecting a subject having a cancer that expresses IL-7Rα protein and administering to the subject a therapeutically effective amount of an IL-7Rα-specific antibody, antigen binding fragment, conjugate, or CAR T cell as disclosed herein. Also provided herein is a method of inhibiting growth or metastasis of IL-7Rα-positive cancer cells by selecting a subject having an IL-7Rα-positive cancer and administering to the subject a therapeutically effective amount of an IL-7Rα-specific antibody, antigen binding fragment, conjugate, or CAR T cell as disclosed herein.

A therapeutically effective amount of an IL-7Rα-specific antibody, antigen binding fragment, conjugate, or CAR T cell as disclosed herein will depend upon the severity of the disease and the general state of the patient's health. A therapeutically effective amount is that which provides either subjective relief of a symptom(s) or an objectively identifiable improvement as noted by the clinician or other qualified observer. In some examples, therapeutic amounts are amounts which eliminate or reduce the patient's tumor burden, or which prevent or reduce the proliferation of metastatic cells (such as IL-7Rα-positive cancer cells).

Subjects that can benefit from the disclosed methods include human and veterinary subjects. Subjects can be screened prior to initiating the disclosed therapies, for example to determine whether the subject has an IL-7Rα-positive cancer such as ALL. The presence of the IL-7Rα cancer indicates that the subject can be treated using the methods provided herein.

Administration of the antibodies, antigen binding fragments, conjugates, CAR T cells, or compositions can be accompanied by administration of other anti-cancer agents or therapeutic treatments (such as surgical resection of a tumor or radiation therapy). Any suitable anti-cancer agent can be administered in combination with the antibodies and conjugates disclosed herein. Exemplary anti-cancer agents include, but are not limited to, chemotherapeutic agents, such as, for example, mitotic inhibitors, alkylating agents, anti-metabolites, intercalating antibiotics, growth factor inhibitors, cell cycle inhibitors, enzymes, topoisomerase inhibitors, anti-survival agents, biological response modifiers, anti-hormones (e.g. anti-androgens) and anti-angiogenesis agents. Other anti-cancer treatments include radiation therapy and other antibodies that specifically target cancer cells.

Non-limiting examples of alkylating agents include nitrogen mustards (such as mechlorethamine, cyclophosphamide, melphalan, uracil mustard or chlorambucil), alkyl sulfonates (such as busulfan), nitrosoureas (such as carmustine, lomustine, semustine, streptozocin, or dacarbazine).

Non-limiting examples of antimetabolites include folic acid analogs (such as methotrexate), pyrimidine analogs (such as 5-FU or cytarabine), and purine analogs, such as mercaptopurine or thioguanine.

Non-limiting examples of natural products include vinca alkaloids (such as vinblastine, vincristine, or vindesine), epipodophyllotoxins (such as etoposide or teniposide), antibiotics (such as dactinomycin, daunorubicin, doxorubicin, bleomycin, plicamycin, or mitomycin C), and enzymes (such as L-asparaginase).

Non-limiting examples of miscellaneous agents include platinum coordination complexes (such as cis-diamine-dichloroplatinum II also known as cisplatin), substituted ureas (such as hydroxyurea), methyl hydrazine derivatives (such as procarbazine), and adrenocrotical suppressants (such as mitotane and aminoglutethimide).

Non-limiting examples of hormones and antagonists include adrenocorticosteroids (such as prednisone, prednisolone), progestins (such as hydroxyprogesterone caproate, medroxyprogesterone acetate, and magestrol acetate), estrogens (such as diethylstilbestrol and ethinyl estradiol), anti-estrogens (such as tamoxifen), and androgens (such as testerone proprionate and fluoxymesterone).

Examples of the most commonly used chemotherapy drugs include Adriamycin, Alkeran, Ara-C, BiCNU, Busulfan, CCNU, Carboplatinum, Cisplatinum, Cytoxan, Daunorubicin, DTIC, 5-FU, Fludarabine, Hydrea, Idarubicin, Ifosfamide, Methotrexate, Mithramycin, Mitomycin, Mitoxantrone, Nitrogen Mustard, Taxol (or other taxanes, such as docetaxel), Velban, Vincristine, VP-16, while some more newer drugs include Gemcitabine (Gemzar), Herceptin®, Irinotecan (Camptosar, CPT-11), Leustatin, Navelbine, Rituxan STI-571, Taxotere, Topotecan (Hycamtin), Xeloda (Capecitabine), Zevelin and calcitriol.

Non-limiting examples of immunomodulators that can be used include AS-101 (Wyeth-Ayerst Labs.), bropirimine (Upjohn), gamma interferon (Genentech), GM-CSF (granulocyte macrophage colony stimulating factor; Genetics Institute), IL-2 (Cetus or Hoffman-LaRoche), human immune globulin (Cutter Biological), IMREG (from Imreg of New Orleans, La.), SK&F 106528, and TNF (tumor necrosis factor; Genentech).

Another common treatment for some types of cancer is surgical treatment, for example surgical resection of the cancer or a portion of it. Another example of a treatment is radiotherapy, for example administration of radioactive material or energy (such as external beam therapy) to the cancer site to help eradicate the cancer or shrink it prior to surgical resection.

In another aspect, a therapeutically effective amount of a combination therapy including administration of any of the IL-7Rα-specific antibodies, antigen binding fragments, conjugates, CAR T cells, or compositions described herein with administration a CXCR4 antagonist can be provided to a patient. As described in the Examples, combination therapy including an IL-7Rα antibody and a CXCR4 antagonist synergistically depleted T-ALL xenograft cells from bone marrow in a mouse model of T-ALL. In some embodiments, the combination therapy can include the administration of an IL-7Rα-specific antibody, antigen binding fragment, conjugate, or CAR T cell as described herein as well as administration of the CXCR4 antagonist AMD3100 (plerixafor, Genzyme Corp.).

Accordingly, the combination therapy may provide synergy and prove synergistic, that is, the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation, a synergistic effect may be attained when the compounds are administered or delivered sequentially, for example by different injections in separate syringes. In general, during alternation, an effective dosage of each active ingredient is administered sequentially, i.e. serially, whereas in combination therapy, effective dosages of two or more active ingredients are administered together. The synergy allows for reduced dosages of the active agents in combination as compared to the dosages for either active individually. The reduced dosage can help reduce any side effects that may appear. One of skill in medicine can best determine the appropriate dose of the additional therapeutic agent by considering the state of the patient, the recommended dose, the severity of disease, and any synergistic effect of the combination.

In some examples, a subject is administered the DNA encoding the antibody or antigen binding fragments thereof, to provide in vivo antibody production, for example using the cellular machinery of the subject. Immunization by nucleic acid constructs is well known in the art and taught, for example, in U.S. Pat. Nos. 5,643,578, and 5,593,972 and 5,817,637. U.S. Pat. No. 5,880,103 describes several methods of delivery of nucleic acids encoding to an organism.

One approach to administration of nucleic acids is direct administration with plasmid DNA, such as with a mammalian expression plasmid. The nucleotide sequence encoding the disclosed antibody, or antigen binding fragments thereof, can be placed under the control of a promoter to increase expression. The methods include liposomal delivery of the nucleic acids. Such methods can be applied to the production of an antibody, or antigen binding fragments thereof, by one of ordinary skill in the art. In some embodiments, a disclosed antibody or antigen binding fragment is expressed in a subject using the pVRC8400 vector (described in Barouch et al., J. Virol, 79, 8828-8834, 2005, which is incorporated by reference herein).

The nucleic acid molecules encoding the disclosed antibodies or antigen binding fragments can be included in a viral vector, for example for expression of the antibody or antigen binding fragment in a host cell, or a subject (such as a subject with or at risk of T-ALL). A number of viral vectors have been constructed, that can be used to express the disclosed antibodies or antigen binding fragments, such as a retroviral vector, an adenoviral vector, or an adeno-associated virus (AAV) vector. In several examples, the viral vector can be replication-competent. For example, the viral vector can have a mutation in the viral genome that does not inhibit viral replication in host cells. The viral vector also can be conditionally replication-competent. In other examples, the viral vector is replication-deficient in host cells.

In several embodiments, a subject (such as a human subject with or at risk of T-ALL) can be administered a therapeutically effective amount of an adeno-associated virus (AAV) viral vector that includes one or more nucleic acid molecules encoding a disclosed antibody or antigen binding fragment. The AAV viral vector is designed for expression of the nucleic acid molecules encoding a disclosed antibody or antigen binding fragment, and administration of the therapeutically effective amount of the AAV viral vector to the subject leads to expression of a therapeutically effective amount of the antibody or antigen binding fragment in the subject. Non-limiting examples of AAV viral vectors that can be used to express a disclosed antibody or antigen binding fragment in a subject include those provided in Johnson et al ("Vector-mediated gene transfer engenders long-lived neutralizing activity and protection against SIV infection in monkeys," Nat. Med., 15(8):901-906, 2009) and Gardner et al. ("AAV-expressed eCD4-Ig provides durable protection from multiple SHIV challenges," Nature, 519 (7541): 87-91, 2015), each of which is incorporated by reference herein in its entirety.

In one embodiment, a nucleic acid encoding a disclosed antibody, or antigen binding fragments thereof, is introduced directly into cells. For example, the nucleic acid can be loaded onto gold microspheres by standard methods and introduced into the skin by a device such as Bio-Rad's HELIOS™ Gene Gun. The nucleic acids can be "naked," consisting of plasmids under control of a strong promoter.

Typically, the DNA is injected into muscle, although it can also be injected directly into other sites. Dosages for injection are usually around 0.5 g/kg to about 50 mg/kg, and typically are about 0.005 mg/kg to about 5 mg/kg (see, e.g., U.S. Pat. No. 5,589,466).

Autoimmune Disorders

In additional embodiments, a method is provided for preventing or treating an autoimmune disorder in a subject by administering to the subject a therapeutically effective amount of an IL-7Rα specific antibody or antigen binding fragment as provided herein. Polymorphisms within components of the IL-7 pathway are known to alter risk of an autoimmune disorder. For example, an allele encoding a threonine at position 244 of IL-7Rα is a high risk allele for autoimmunity, but an allele encoding an isoleucine at the same position is a low risk allele for autoimmunity. The position 244 polymorphism lies in the same region in exon 6 identified for gain-of-function oncogenic mutations. One non-limiting explanation for the increase in autoimmunity risk due to particular polymorphisms in the IL-7Rα gene is that these mutations may lead to increased IL-7R signaling activity. Accordingly, targeting the IL-7R pathway may have therapeutic benefit in numerous diseases with autoimmune or immune excess components. A non-limiting list of autoimmune diseases for which an association of IL-7Rα polymorphism and autoimmunity risk has been shown is provided in the following table.

example, fatigue, fever, weight loss, weight gain, joint pain, joint stiffness, joint swelling, malar rash, skin lesions, mouth sores, nose ulcers, hair loss, Raynaud's phenomenon, shortness of breath, chest pain, dry eyes, bruising, anxiety, depression and memory loss.

In some embodiments, administration of the therapeutically effective amount of the IL-7Rα specific antibody or antigen binding fragment to a subject with multiple sclerosis can reduce or prevent one or more symptoms of the multiple sclerosis including, for example, limb paralysis, tremors, difficulty walking, swallowing difficulties, blindness, blurring vision, and muscle weakness.

In some embodiments, administration of the therapeutically effective amount of the IL-7Rα specific antibody or antigen binding fragment to a subject with graft versus host disease can reduce or prevent one or more symptoms of the

| Disease | IL-7Rα polymorphism | reference |
|---|---|---|
| multiple sclerosis | T244I (exon 6) | Hafler et al., *N. Engl. J. Med.*, 357:851-62, 2007 |
|  |  | Gregory et al., *Nat. Genet.*, 39:1083-91, 2007 |
|  |  | Lundmark et al., *Neuroimmunol.*, 192:171-73, 2007 |
| Type I diabetes | T244I (exon 6) | Todd et al., *Nat. Genet.*, 39:857-64, 2007 |
|  |  | Santiago et al., *Diabetologia*, 51:1653-58, 2008 |
| rheumatoid arthritis | T244I (exon 6) | O'Doherty et al., *Tissue Antigens*, 74:429-31, 2009 |
| Sarcoidosis | T244I (exon 6) | Heron et al., *Genes Immun.*, 10:647-53, 2009 |
| Atopic dermatitis | T244I (exon 6) and T46I (exon 2) | Hoffjan et al., *J. Dermatol Sci.*, 55:138-40, 2009 |
| Inhalation allergy | T244I (exon 6) and I118V (exon 4) | Shamim et al., *Int. J. Immunogenet.*, 34:149-51, 2007 |
| graft versus host disease | T46I (exon 2) and I118V (exon 4) | Shamim et al., *Transplantation*, 91:731-36, 2011 |
| Primary Biliary Cirrhosis | (possible T244I) | Mells et al., *Nat. Genet.*, 43:329-32, 2011 |
| Inflammatory bowel disease | (non 244) | Anderson et al., *Nat. Genet.*, 43:246-52, 2011 |

Accordingly, in some embodiments, the disclosed antibodies and antigen binding fragments can be used to treat or prevent an autoimmune disorder such as multiple sclerosis, type 1 diabetes, rheumatoid arthritis, sarcoidosis, atopic dermatitis, inhalation allergy, primary biliary cirrhosis, or inflammatory bowel disease, in a subject, the method comprising administering to the subject a therapeutically effective amount of a disclosed antibody or antigen binding fragment that specifically binds to IL-7Rα. In some embodiments, the disclosed antibodies and antigen binding fragments can be used to treat or prevent graft versus host disease in a subject, the method comprising administering to the subject a therapeutically effective amount of a disclosed antibody or antigen binding fragment that specifically binds to IL-7Rα.

In some embodiments, administration of the therapeutically effective amount of the IL-7Rα specific antibody or antigen binding fragment to a subject with type I diabetes can reduce or prevent one or more symptoms of the type I diabetes including, for example, a reduction in blood glucose level and/or improved glucose tolerance in the subject.

In some embodiments, administration of the therapeutically effective amount of the IL-7Rα specific antibody or antigen binding fragment to a subject with rheumatoid arthritis can reduce or prevent one or more symptoms of the rheumatoid arthritis including, for example, joint stiffness, joint swelling, joint pain, and/or joint redness and warmth.

In some embodiments, administration of the therapeutically effective amount of the IL-7Rα specific antibody or antigen binding fragment to a subject with lupus can reduce or prevent one or more symptoms of the lupus including, for graft versus host disease including, for example, abdominal pain, abdominal cramps, fever, jaundice, skin rash, vomiting, weight loss, dry eyes, dry mouth, hair loss, hepatitis, lung disorders, and digestive tract disorders.

In some embodiments, administration of the therapeutically effective amount of the IL-7Rα specific antibody or antigen binding fragment to a subject with acute graft versus host disease can reduce or prevent one or more symptoms of the acute graft versus host disease including, for example, pneumonitis, intestinal inflammation, diarrhea, abdominal pain, abdominal cramps, fever, jaundice, nausea, vomiting, liver damage, skin rash, skin damage, damage to the mucosa, sloughing of the mucosal membrane, damage to the gastrointestinal tract, weight loss, maculopapular rash, elevated bilirubin levels, morbidity and mortality.

In some embodiments, administration of the therapeutically effective amount of the IL-7Rα specific antibody or antigen binding fragment to a subject with chronic graft versus host disease can reduce or prevent one or more symptoms of the chronic graft versus host disease including, for example, dry eyes, dry mouth, hair loss, hepatitis, lung disorders, digestive tract disorders, skin rash, oral ulcer, oral atrophy, onchodystrophy, sicca syndrome, sclerosis, lichenplanus-like lesions, poikiloderma, esophageal webs, fasciitis and bronchiolitis obliterans, and damage to the liver, skin and mucosa, connective tissue, exocrine glands and/or the gastrointestinal tract.

2. Dosages

A therapeutically effective amount of a IL-7Rα-specific antibody, antigen binding fragment, conjugate, CAR, T cell expressing a CAR, or nucleic acid molecule encoding such molecules, will depend upon the severity of the disease and the general state of the patient's health. A therapeutically effective amount is that which provides either subjective relief of a symptom(s) or an objectively identifiable improvement as noted by the clinician or other qualified observer. The IL-7Rα-specific antibody, antigen binding fragment, conjugate, CAR, T cell expressing a CAR, or nucleic acid molecule encoding such molecules, can be administered in conjunction with another therapeutic agent, either simultaneously or sequentially.

Single or multiple administrations of a composition including a disclosed IL-7Rα-specific antibody, antigen binding fragment, conjugate, CAR, T cell expressing a CAR, or nucleic acid molecule encoding such molecules, can be administered depending on the dosage and frequency as required and tolerated by the patient. Compositions including the IL-7Rα-specific antibody, antigen binding fragment, conjugate, CAR, T cell expressing a CAR, or nucleic acid molecule encoding such molecules, should provide a sufficient quantity of at least one of the IL-7Rα-specific antibody, antigen binding fragment, conjugate, CAR, T cell expressing a CAR, or nucleic acid molecule encoding such molecules to effectively treat the patient. The dosage can be administered once, but may be applied periodically until either a therapeutic result is achieved or until side effects warrant discontinuation of therapy. In one example, a dose of the antibody or antigen binding fragment is infused for thirty minutes every other day. In this example, about one to about ten doses can be administered, such as three or six doses can be administered every other day. In a further example, a continuous infusion is administered for about five to about ten days. The subject can be treated at regular intervals, such as monthly, until a desired therapeutic result is achieved. Generally, the dose is sufficient to treat or ameliorate symptoms or signs of disease without producing unacceptable toxicity to the patient.

Data obtained from cell culture assays and animal studies can be used to formulate a range of dosage for use in humans. The dosage normally lies within a range of circulating concentrations that include the $ED_{50}$, with little or minimal toxicity. The dosage can vary within this range depending upon the dosage form employed and the route of administration utilized. The therapeutically effective dose can be determined from cell culture assays and animal studies.

In certain embodiments, the antibody or antigen binding fragment that specifically binds IL-7Rα, or conjugate thereof, or a nucleic acid molecule or vector encoding such a molecule, or a composition including such molecules, is administered at a dose in the range of from about 5 or 10 nmol/kg to about 300 nmol/kg, or from about 20 nmol/kg to about 200 nmol/kg, or at a dose of about 5, 10, 15, 20, 25, 30, 35, 40, 45, 50, 55, 60, 65, 70, 75, 80, 85, 90, 95, 100, 110, 120, 125, 130, 140, 150, 160, 170, 175, 180, 190, 200, 210, 220, 230, 240, 250, 260, 270, 280, 290, 300, 350, 400, 450, 500, 750, 1000, 1250, 1500, 1750 or 2000 nmol/kg, or at a dose of about 5, 10, 20, 30, 40, 50, 60, 70, 80, 90, 100, 110, 120, 130, 140, 150, 160, 170, 180, 190, 200, 250, 300, 350, 400, 450, 500, 550, 600, 650, 700, 750, 800, 850, 900, 950 or 1000 μg/kg, or about 1, 1.25, 1.5, 2, 2.5, 3, 3.5, 4, 4.5, 5, 5.5, 6, 6.5, 7, 7.5, 8, 8.5, 9, 9.5 or 10 mg/kg, or other dose deemed appropriate by the treating physician. The doses described herein can be administered according to the dosing frequency/frequency of administration described herein, including without limitation daily, 2 or 3 times per week, weekly, every 2 weeks, every 3 weeks, monthly, etc.

In some embodiments, a disclosed therapeutic agent is administered may be administered intravenously, subcutaneously or by another mode daily or multiple times per week for a period of time, followed by a period of no treatment, then the cycle is repeated. In some embodiments, the initial period of treatment (e.g., administration of the therapeutic agent daily or multiple times per week) is for 3 days, 1 week, 2 weeks, 3 weeks, 4 weeks, 5 weeks, 6 weeks, 7 weeks, 8 weeks, 9 weeks, 10 weeks, 11 weeks or 12 weeks. In a related embodiment, the period of no treatment lasts for 3 days, 1 week, 2 weeks, 3 weeks or 4 weeks. In certain embodiments, the dosing regimen of the therapeutic agent is daily for 3 days followed by 3 days off; or daily or multiple times per week for 1 week followed by 3 days or 1 week off; or daily or multiple times per week for 2 weeks followed by 1 or 2 weeks off; or daily or multiple times per week for 3 weeks followed by 1, 2 or 3 weeks off; or daily or multiple times per week for 4, 5, 6, 7, 8, 9, 10, 11 or 12 weeks followed by 1, 2, 3 or 4 weeks off.

3. Modes of Administration

An IL-7Rα-specific antibody, antigen binding fragment, conjugate, CAR, T cell expressing a CAR, or nucleic acid molecule encoding such molecules, or a composition including such molecules, as well as additional agents, can be administered to subjects in various ways, including local and systemic administration, such as, e.g., by injection subcutaneously, intravenously, intra-arterially, intraperitoneally, intramuscularly, intradermally, or intrathecally. In an embodiment, a therapeutic agent is administered by a single subcutaneous, intravenous, intra-arterial, intraperitoneal, intramuscular, intradermal or intrathecal injection once a day. The therapeutic agent can also be administered by direct injection at or near the site of disease.

The therapeutic agent may also be administered orally in the form of microspheres, microcapsules, liposomes (uncharged or charged (e.g., cationic)), polymeric microparticles (e.g., polyamides, polylactide, polyglycolide, poly(lactide-glycolide)), microemulsions, and the like.

A further method of administration is by osmotic pump (e.g., an Alzet pump) or mini-pump (e.g., an Alzet mini-osmotic pump), which allows for controlled, continuous and/or slow-release delivery of the therapeutic agent or pharmaceutical composition over a pre-determined period. The osmotic pump or mini-pump can be implanted subcutaneously, or near a target site.

It will be apparent to one skilled in the art that the therapeutic agent or compositions thereof can also be administered by other modes. Determination of the most effective mode of administration of the therapeutic agent or compositions thereof is within the skill of the skilled artisan. The therapeutic agent can be administered as pharmaceutical formulations suitable for, e.g., oral (including buccal and sublingual), rectal, nasal, topical, pulmonary, vaginal or parenteral (including intramuscular, intraarterial, intrathecal, subcutaneous and intravenous) administration, or in a form suitable for administration by inhalation or insufflation. Depending on the intended mode of administration, the pharmaceutical formulations can be in the form of solid, semi-solid or liquid dosage forms, such as tablets, suppositories, pills, capsules, powders, liquids, suspensions, emulsions, creams, ointments, lotions, and the like. The formulations can be provided in unit dosage form suitable for single administration of a precise dosage. The formulations comprise an effective amount of a therapeutic agent, and one or more pharmaceutically acceptable excipients, carriers and/or diluents, and optionally one or more other biologically active agents.

4. Compositions

Compositions are provided that include one or more of the IL-7Rα-specific antibody, antigen binding fragment, conjugate, CAR, T cell expressing a CAR, or nucleic acid molecule encoding such molecules, that are disclosed herein in a carrier. The compositions are useful, for example, for example, for the treatment or prevention of ALL (such as T-ALL or B-ALL) in a subject. The compositions can be prepared in unit dosage forms for administration to a subject. The amount and timing of administration are at the discretion of the treating physician to achieve the desired purposes. The IL-7Rα-specific antibody, antigen binding fragment, conjugate, CAR, T cell expressing a CAR, or nucleic acid molecule encoding such molecules can be formulated for systemic or local administration. In one example, the IL-7Rα-specific antibody, antigen binding fragment, conjugate, CAR, T cell expressing a CAR, or nucleic acid molecule encoding such molecules, is formulated for parenteral administration, such as intravenous administration.

In some embodiments, the compositions comprise an antibody, antigen binding fragment, or conjugate thereof, in at least 70% (such as at least 75%, at least 80%, at least 85%, at least 90%, at least 95%, at least 96%, at least 97%, at least 98% or at least 99% purity. In certain embodiments, the compositions contain less than 10% (such as less than 5%, less than 4%, less than 3%, less than 2%, less than 1%, less than 0.5%, or even less) of macromolecular contaminants, such as other mammalian (e.g., human) proteins.

The compositions for administration can include a solution of the IL-7Rα-specific antibody, antigen binding fragment, conjugate, CAR, T cell expressing a CAR, or nucleic acid molecule encoding such molecules, dissolved in a pharmaceutically acceptable carrier, such as an aqueous carrier. A variety of aqueous carriers can be used, for example, buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of antibody in these formulations can vary widely, and will be selected primarily based on fluid volumes, viscosities, body weight and the like in accordance with the particular mode of administration selected and the subject's needs.

A typical composition for intravenous administration includes about 0.01 to about 30 mg/kg of antibody or antigen binding fragment or conjugate per subject per day (or the corresponding dose of a conjugate including the antibody or antigen binding fragment). Actual methods for preparing administrable compositions will be known or apparent to those skilled in the art and are described in more detail in such publications as *Remington's Pharmaceutical Science*, 19th ed., Mack Publishing Company, Easton, PA (1995). In some embodiments, the composition can be a liquid formulation including one or more antibodies, antigen binding fragments (such as an antibody or antigen binding fragment that specifically binds to IL-7Rα), in a concentration range from about 0.1 mg/ml to about 20 mg/ml, or from about 0.5 mg/ml to about 20 mg/ml, or from about 1 mg/ml to about 20 mg/ml, or from about 0.1 mg/ml to about 10 mg/ml, or from about 0.5 mg/ml to about 10 mg/ml, or from about 1 mg/ml to about 10 mg/ml.

Antibodies, or an antigen binding fragment thereof or a conjugate or a nucleic acid encoding such molecules, can be provided in lyophilized form and rehydrated with sterile water before administration, although they are also provided in sterile solutions of known concentration. The antibody solution, or an antigen binding fragment or a nucleic acid encoding such antibodies or antibody binding fragments, can then be added to an infusion bag containing 0.9% sodium chloride, USP, and typically administered at a dosage of from 0.5 to 15 mg/kg of body weight. Considerable experience is available in the art in the administration of antibody drugs, which have been marketed in the U.S. since the approval of RITUXAN® in 1997. Antibodies, antigen binding fragments, conjugates, or a nucleic acid encoding such molecules, can be administered by slow infusion, rather than in an intravenous push or bolus. In one example, a higher loading dose is administered, with subsequent, maintenance doses being administered at a lower level. For example, an initial loading dose of 4 mg/kg may be infused over a period of some 90 minutes, followed by weekly maintenance doses for 4-8 weeks of 2 mg/kg infused over a 30 minute period if the previous dose was well tolerated.

Controlled-release parenteral formulations can be made as implants, oily injections, or as particulate systems. For a broad overview of protein delivery systems see, Banga, A. J., *Therapeutic Peptides and Proteins: Formulation, Processing, and Delivery Systems*, Technomic Publishing Company, Inc., Lancaster, PA, (1995). Particulate systems include microspheres, microparticles, microcapsules, nanocapsules, nanospheres, and nanoparticles. Microcapsules contain the therapeutic protein, such as a cytotoxin or a drug, as a central core. In microspheres the therapeutic is dispersed throughout the particle. Particles, microspheres, and microcapsules smaller than about 1 m are generally referred to as nanoparticles, nanospheres, and nanocapsules, respectively. Capillaries have a diameter of approximately 5 m so that only nanoparticles are administered intravenously. Microparticles are typically around 100 m in diameter and are administered subcutaneously or intramuscularly. See, for example, Kreuter, J., *Colloidal Drug Delivery Systems*, J. Kreuter, ed., Marcel Dekker, Inc., New York, NY, pp. 219-342 (1994); and Tice & Tabibi, *Treatise on Controlled Drug Delivery*, A. Kydonieus, ed., Marcel Dekker, Inc. New York, NY, pp. 315-339, (1992).

Polymers can be used for ion-controlled release of the antibody compositions disclosed herein. Various degradable and nondegradable polymeric matrices for use in controlled drug delivery are known in the art (Langer, *Accounts Chem. Res.* 26:537-542, 1993). For example, the block copolymer, polaxamer 407, exists as a viscous yet mobile liquid at low temperatures but forms a semisolid gel at body temperature. It has been shown to be an effective vehicle for formulation and sustained delivery of recombinant interleukin-2 and urease (Johnston et al., *Pharm. Res.* 9:425-434, 1992; and Pec et al., *J. Parent. Sci. Tech.* 44(2):58-65, 1990). Alternatively, hydroxyapatite has been used as a microcarrier for controlled release of proteins (Ijntema et al., *Int. J. Pharm.* 112:215-224, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, PA (1993)). Numerous additional systems for controlled delivery of therapeutic proteins are known (see U.S. Pat. Nos. 5,055,303; 5,188,837; 4,235,871; 4,501,728; 4,837,028; 4,957,735; 5,019,369; 5,055,303; 5,514,670; 5,413,797; 5,268,164; 5,004,697; 4,902,505; 5,506,206; 5,271,961; 5,254,342 and 5,534,496).

5. Methods of Detection and Diagnosis

Methods are also provided for the detection of the expression of IL-7Rα in vitro or in vivo. In one example, expression of IL-7Rα is detected in a biological sample, and can be used to detect the presence of a cell with cell-surface expression of IL-7Rα in the sample. The sample can be any sample, including, but not limited to, tissue from biopsies, autopsies and pathology specimens. Biological samples also include sections of tissues, for example, frozen sections taken for histological purposes. Biological samples further include body fluids, such as blood, serum, plasma, sputum, spinal fluid or urine. The method of detection can include contacting a cell or sample, or administering to a subject, an antibody or antigen binding fragment that specifically binds to IL-7Rα, or conjugate there of (e.g. a conjugate including a detectable marker) under conditions sufficient to form an immune complex, and detecting the immune complex (e.g., by detecting a detectable marker conjugated to the antibody or antigen binding fragment.

One embodiment provides a method of determining if a subject has cancer by contacting a sample from the subject with a monoclonal antibody (or conjugate) disclosed herein; and detecting binding of the antibody to the sample. An increase in binding of the antibody to the sample as compared to binding of the antibody to a control sample identifies the subject as having cancer.

Another embodiment provides a method of confirming a diagnosis of cancer in a subject by contacting a sample from a subject diagnosed with cancer with a monoclonal antibody (or conjugate) disclosed herein; and detecting binding of the antibody to the sample. An increase in binding of the antibody to the sample as compared to binding of the antibody to a control sample confirms the diagnosis of cancer in the subject.

In some embodiments, the cancer is ALL, such as T-ALL or B-ALL. In some embodiments the cancer is one that expresses IL-7Rα. In some examples, the control sample is a sample from a subject without cancer. In particular examples, the sample is a blood or tissue sample.

In one embodiment, the antibody or antigen binding fragment is directly labeled with a detectable marker. In another embodiment, the antibody that binds IL-7Rα (the first antibody) is unlabeled and a second antibody or other molecule that can bind the antibody that binds the first antibody is utilized for detection. As is well known to one of skill in the art, a second antibody is chosen that is able to specifically bind the specific species and class of the first antibody. For example, if the first antibody is a human IgG, then the secondary antibody may be an anti-human-IgG. Other molecules that can bind to antibodies include, without limitation, Protein A and Protein G, both of which are available commercially.

Suitable labels for the antibody, antigen binding fragment or secondary antibody are described above, and include various enzymes, prosthetic groups, fluorescent materials, luminescent materials, magnetic agents and radioactive materials. Non-limiting examples of suitable enzymes include horseradish peroxidase, alkaline phosphatase, beta-galactosidase, or acetylcholinesterase. Non-limiting examples of suitable prosthetic group complexes include streptavidin/biotin and avidin/biotin. Non-limiting examples of suitable fluorescent materials include umbelliferone, fluorescein, fluorescein isothiocyanate, rhodamine, dichlorotriazinylamine fluorescein, dansyl chloride or phycoerythrin. A non-limiting exemplary luminescent material is luminol; a non-limiting exemplary a magnetic agent is gadolinium, and non-limiting exemplary radioactive labels include $^{125}$I, $^{131}$I, $^{35}$S or $^{3}$H.

F. Kits

Kits are also provided. For example, kits for treating a subject with a cancer that expresses IL-7Rα, or for detecting IL-7Rα in a sample or in a subject. The kits will typically include a disclosed IL-7Rα-specific antibody, antigen binding fragment, conjugate, CAR, T cell expressing a CAR, or nucleic acid molecule encoding such molecules, or compositions including such molecules.

In one embodiment, the kit is a diagnostic kit and includes an immunoassay. Although the details of the immunoassays may vary with the particular format employed, the method of detecting IL-7Rα in a biological sample generally includes the steps of contacting the biological sample with an antibody which specifically reacts, under conditions sufficient to form an immune complex, to IL-7Rα. The antibody is allowed to specifically bind under immunologically reactive conditions to form an immune complex, and the presence of the immune complex (bound antibody) is detected directly or indirectly.

The kit can include a container and a label or package insert on or associated with the container. Suitable containers include, for example, bottles, vials, syringes, etc. The containers may be formed from a variety of materials such as glass or plastic. The container typically holds a composition including one or more of the disclosed antibodies, antigen binding fragments, conjugates, nucleic acid molecules, or compositions. In several embodiments the container may have a sterile access port (for example the container may be an intravenous solution bag or a vial having a stopper pierceable by a hypodermic injection needle). A label or package insert indicates that the composition is used for treating the particular condition.

The label or package insert typically will further include instructions for use of the antibodies, antigen binding fragments, conjugates, nucleic acid molecules, or compositions included in the kit. The package insert typically includes instructions customarily included in commercial packages of therapeutic products that contain information about the indications, usage, dosage, administration, contraindications and/or warnings concerning the use of such therapeutic products. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

IV. Examples

The following examples are provided to illustrate particular features of certain embodiments, but the scope of the claims should not be limited to those features exemplified.

Example 1: IL-7Rα-Specific Antibodies for Treating ALL

This example illustrates the isolation and characterization of the 4A10 and 2B8 antibodies. These antibodies specifically bind to the extracellular domain of IL-7Rα, and can direct ADCC-mediated killing of cells the express IL-7Rα on their surface. Further, an in vivo model of T-ALL is used to show that a chimeric form of the 4A10 antibody including a human constant region can direct ADCC-mediated killing of ALL cells (including T-ALL cells) expressing a gain-of-function mutant form of the IL-7R that drives cell proliferation.

Introduction

Acute lymphoblastic leukemia (ALL) is the most common cancer in children, with approximately 3250 new cases per year in the United States. Treatment for ALL has improved dramatically in recent decades, but there remain about 20% of cases that are not cured and ALL remains a leading cause of death in children. ALL also occurs in adults where it has a far less favorable prognosis. The need for new therapeutics in ALL is illustrated, for example, in the incidence of cognitive impairment with chemotherapy in the developing brain (Cheung and Krull, *Neurosci. Biobehav. Rev.*, 53:108-120, 2015). ALL can be subdivided into two broad groups: those derived from immature T cells (T-ALL) and those derived from immature B cells (B-ALL). There have been great advances in understanding the genetic basis of ALL, leading to new sub-classifications of patients based on their genetic aberrations combined with surface phenotype (Mullighan, *J. Clinical Invest.*, 122:3407-3415, 2012; Van Vlierberghe and Ferrando, *J. Clinical Invest.*, 122:3398-3406, 2012).

IL-7, a product of stromal cells, is normally required for T and B cell development and for survival of mature T cells. IL-7 acts on lymphocytes by binding with high affinity to IL-7Rα, then recruiting the common γc chain. This heterodimerization brings together the intracellular domains of IL-7Rα and γc and their associated kinases, Jak1 and Jak3 respectively. These tyrosine kinases have a low level of intrinsic signaling activity, which is greatly increased by mutual phosphorylation. Jak1 and Jak3 then phosphorylate a site on the intracellular domain of IL-7Rα, which recruits Stat5. Stat5 is then phosphorylated, inducing its dimerization and dissociation from IL-7Rα and translocation to the nucleus where it serves as a transcription factor, inducing genes involved in survival and proliferation (reviewed in Jiang et al., *Cytokine Growth Factor Rev.*, 16:513-533, 2005, which is incorporated by reference herein). Most of the lymphocyte requirement for IL-7 is attributable to these survival and proliferative effects, which also makes the IL-7 pathway potentially vulnerable to mutations causing cancer.

Figure 2:
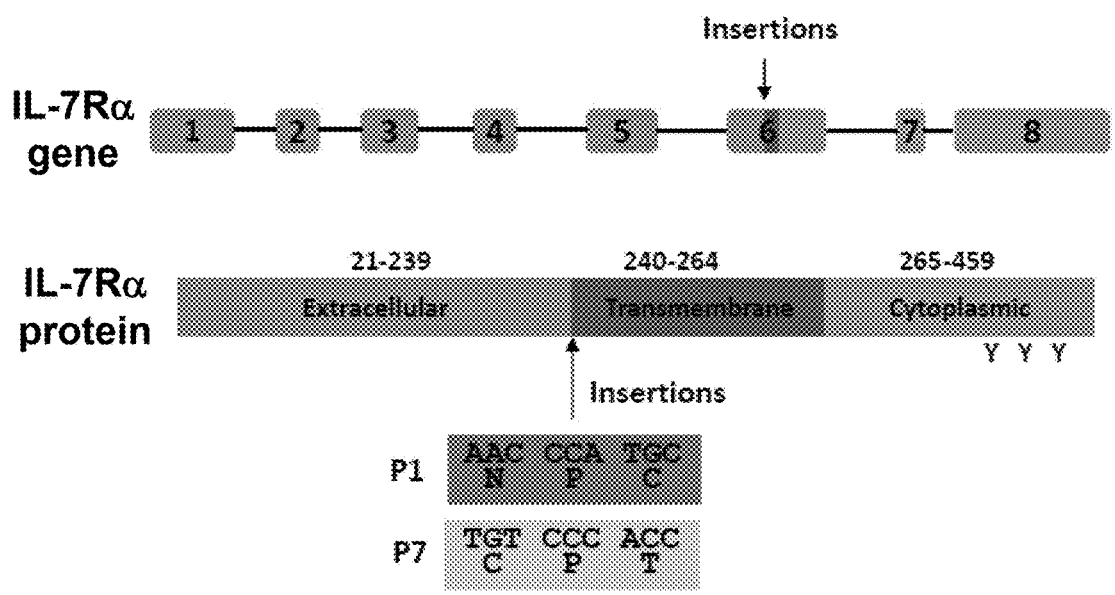
FIG. 2 is a schematic diagram illustrating the prior finding concerning typical somatic mutations in the IL-7Rα gene in T-ALL patients. Patient 1 (P1) and patient 7 (P7) revealed cysteine insertions at the border of the extracellular and transmembrane regions of exon 6. The "P1" and "P7" mutations in the IL-7Rα gene include the mutations shown for the P1 and P7 patients, respectively.
Figure 3:
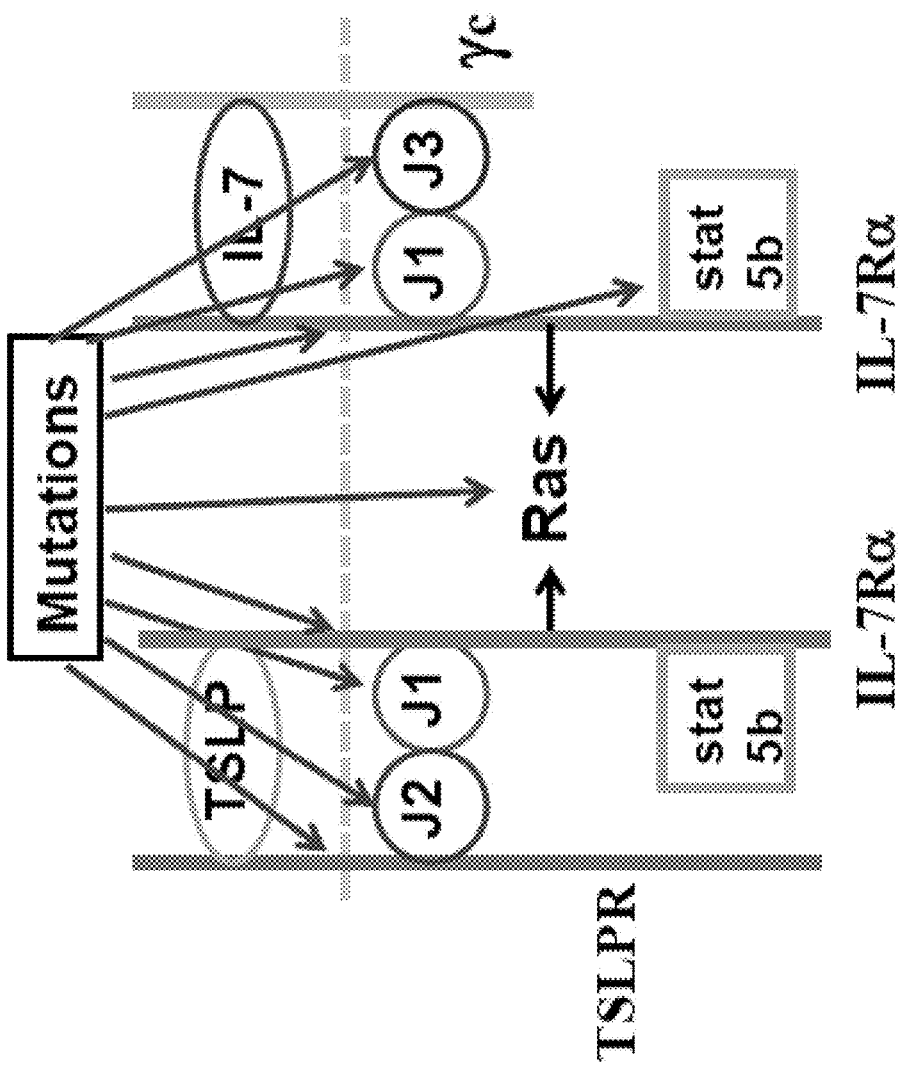
FIG. 3 is a schematic diagram illustrating prior findings concerning genetic mutations in the IL-7 pathway that can lead to T- or B-cell proliferation in ALL. ALL involves the IL-7 receptor pathways. The IL-7 pathway frequently drives T cell proliferation in T-ALL, whereas the thymic stromal lymphopoietin (TSLP) pathway frequently drives B cell proliferation in B-ALL. IL-7 acts on lymphocytes by binding with high affinity to IL-7Rα, and then recruiting the common γc chain. This heterodimerization brings together the intracellular domains of IL-7Rα and γc and their associated kinases, Jak1 and Jak3, respectively (J1 and J3 in the figure). TSLP acts on lymphocytes by binding with high affinity to IL-7Rα, and then recruiting the TSLP receptor (TSLPR). This heterodimerization brings together the intracellular domains of IL-7Rα and TSLPR and their associated kinases, Jak1 and Jak2, respectively (J1 and J2 in the figure). Jak1 and Jak3 (for the IL-7Rα/γc heterodimer) or Jak1 and Jak2 (for the IL-7Rα/TSLPR heterodimer) then phosphorylate a site on the intracellular domain of IL-7Rα, which recruits Stat5b. Stat5b is then phosphorylated, inducing its dimerization and dissociation from IL-7Rα and translocation to the nucleus where it serves as a transcription factor, inducing genes involved in survival and proliferation. Mutations at any point in the IL-7 or TSLP pathway can lead to inappropriate phosphorylation of Stat5b, and resulting lymphocyte proliferation. The P1 and P7 gain-of function mutations in IL-7Rα illustrated in FIG. 2 lead to aberrant IL-7Rα homodimerization, phosphorylation of Stat5b by Jak1, and resulting lymphocyte proliferation.

Prior findings identified gain-of-function mutations in the IL-7Rα gene that lead to over production and accumulation of T-ALL cells (Zenatti et al., *Nat. Genet.*, 43:932-939, 2011, which is incorporated by reference herein). These prior studies found that mutations are observed in multiple cohorts of T-ALL in about 10% of patients (see FIG. 1). These mutations are typically insertions containing cysteines into exon 6 of the IL-7Ra gene, which encodes the border of the extracellular/transmembrane domains of the IL-7Rα protein (see FIG. 2, and, e.g., Shochat et al., *J. Exp. Med.*, 208:901-908, 2011; and Zhang et al., *Nature*, 481: 157-163, 2012, each of which is incorporated by reference herein). Other gain-of-function mutations in the IL-7 pathway can also occur in T-ALL (such as gain-of-function mutations in the genes encoding IL-7Rα, Jak1, Jak3, Stat5b, or Ras), as well as in B-ALL (such as gain-of-function mutations in the genes encoding TSLPR or Jak2) (see FIG. 3). Thus, the IL-7 receptor pathway contains vulnerable proto-oncogenes for immature lymphocytes and targeting this pathway offers therapeutic potential in ALL. Further, the majority of T-ALL cells express IL-7Rα and respond to IL-7 in vitro, showing increased survival (Barata et al., *Blood*, 98:1524-1531, 2001; Touw et al., *Blood*, 75:2097-2101, 1990). Accordingly, monoclonal antibodies that target IL-7Rα may be effective against T-ALL with mutant or WT IL-7Rα. As IL-7Rα can be present on the cell-surface of B cells associated with B-ALL, IL-7Rα-directed antibody may also be effective therapeutics for B-ALL.

Several monoclonal antibodies have been used clinically to treat cancers and their mechanisms of action differ widely. In some examples, monoclonal antibodies are shown to block the signaling from a receptor, whereas in other examples, monoclonal antibodies target cancer cells for killing by innate immune cells. Anti-CD20 (Rituximab) is widely used to treat non-Hodgkin lymphoma and B cell chronic lymphocytic leukemia. Based on its effect of eliminating normal B cells, anti-CD20 is also used to treat psoriasis. Anti-CD20 is thought to mediate its effects via ADCC and phagocytosis of lymphoma and normal B cells (Wilson et al., *Cancer Cell*, 19:101-113, 2011), and it may enhance presentation of tumor antigens to the immune system (reviewed in Abes and Teillaud, *Cancer Metastasis Rev.*, 30:111-124, 2011). In treatment of breast cancer, anti-Her2 (Trastuzumab) juxtamembrane region induces both uncoupling from Her3 as well as ADCC (reviewed in Garrett and Arteaga, *Cancer Biol. Ther.*, 11:793-800, 2011). In treatment of squamous cell carcinoma and colon cancer, the mechanism of anti-EGFR (Cetuximab) is based on blocking receptor dimerization as well as ADCC (reviewed in Brand et al., *Cancer Biol. Ther.*, 11:777-792, 2011). Accordingly, ALL cells in patients may be killed by IL-7Rα targeted monoclonal antibodies based on several possible mechanisms ranging from blocked signaling to targeting cells for ADCC, and we recognize that, analogous to anti-CD20, there could be killing of the patient's normal T cells.

Isolation and Characterization of the 4A10 and 2B8 Antibodies

Mouse monoclonal antibodies directed against IL-7Rα were generated using standard hybridoma production assays. An engineered IL-7Rα extracellular domain from a T-ALL patient that encoded a gain-of-function cysteine insertion was expressed in insect cells, and the resulting soluble IL-7Rα ectodomain homodimer was purified. Mice were immunized with the purified soluble T-ALL IL-7Rα homodimer, and antibody produced from hybridoma cell lines prepared from the immunized mice was screened for IL-7Rα binding. The first round of screenings was performed on WT IL-7Rα extracellular domain immobilized on plastic, and although several clones were found, none bound to IL-7Rα on the cell surface. Accordingly, a second round of screening was performed to assay for mAb that binds to cells expressing full-length WT IL-7Rα. Two positive hybridomas were identified that resulted in 4A10 and 2B8 antibodies, respectively. The identified antibodies, and corresponding sequence identifiers are as follows:

| Antibody | $V_H$ protein SEQ ID | $V_H$ CDR (kabat) SEQ ID | $V_L$ protein SEQ ID | $V_L$ CDR (Kabat) SEQ ID | $V_H$ DNA SEQ ID | $V_L$ DNA SEQ ID |
|---|---|---|---|---|---|---|
| 4A10 | 1 | 5, 6, 7 | 2 | 8, 9, 10 | 25 | 26 |
| 2B8 | 3 | 11, 12, 13 | 4 | 14, 15, 16 | 27 | 28 |

Figure 4:
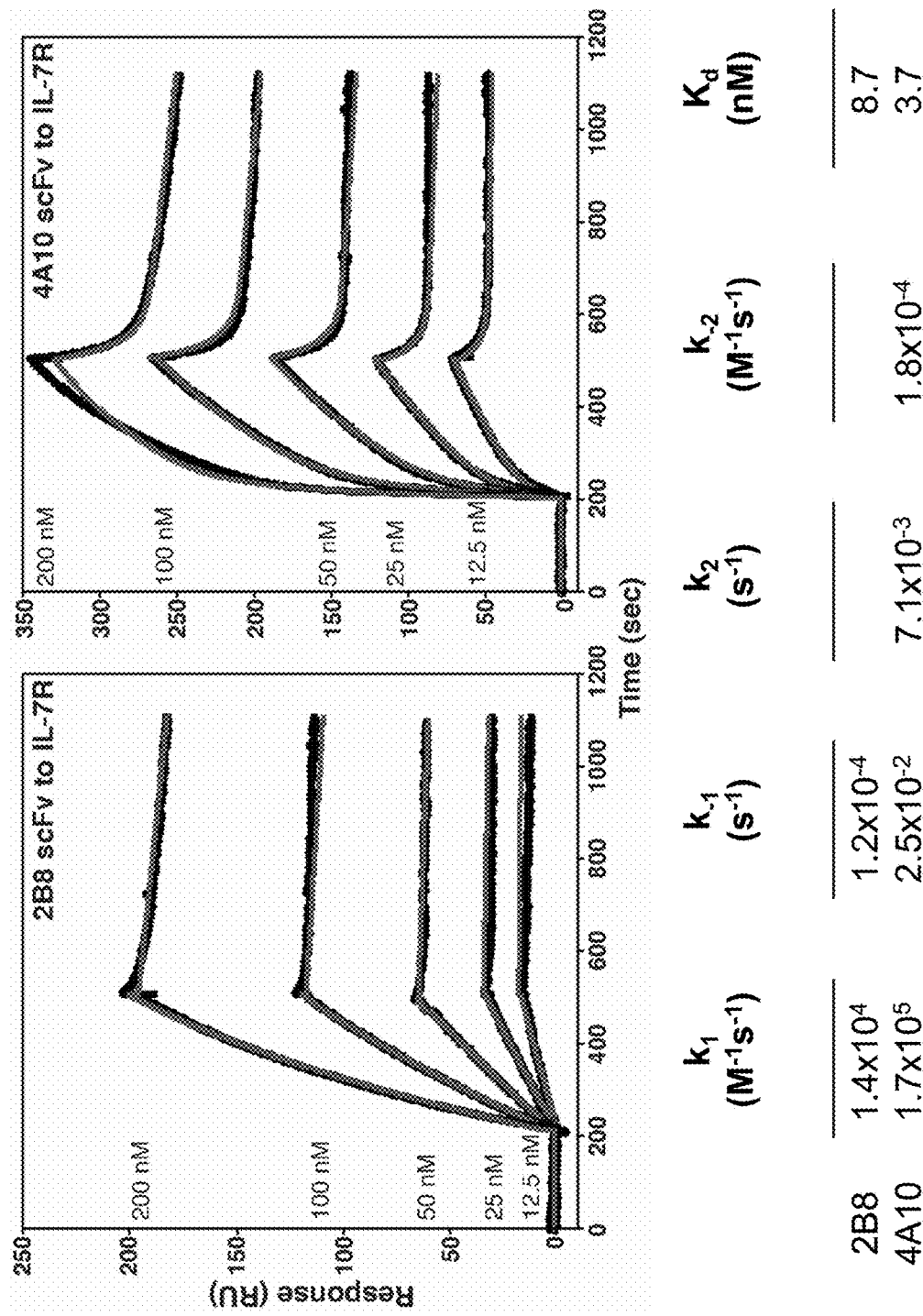
FIG. 4 is a set of graphs illustrating the binding kinetics of 4A10 and 2B8 scFvs for binding to IL-7Rα extracellular domain. scFvs including the heavy and light chain variable regions of the 4A10 or 2B8 antibody were prepared and assayed for binding to purified IL-7Rα ectodomain using surface plasmon resonance. The resulting $K_D$ values for 2B8 or 4A10 binding to IL-7Rα are shown.

The binding affinity of the 4A10 and 2B8 antibodies for IL-7Rα was evaluated using surface plasmon resonance (FIG. 4). scFvs including the heavy and light chain variable regions of the 4A10 or 2B8 antibody were prepared and used in the binding assays. IL-7Rα ectodomain was coupled to an SPR sensor-chip and binding was assayed by injecting 4A10 or 2B8 scFv over the flow cells of the sensor-chip, and detecting the binding response. As illustrated in FIG. 4, the calculated $K_D$ for 2B8 and 4A10 binding to IL-7Rα is 8.7 nM and 3.7 nM, respectively.

Figure 5:
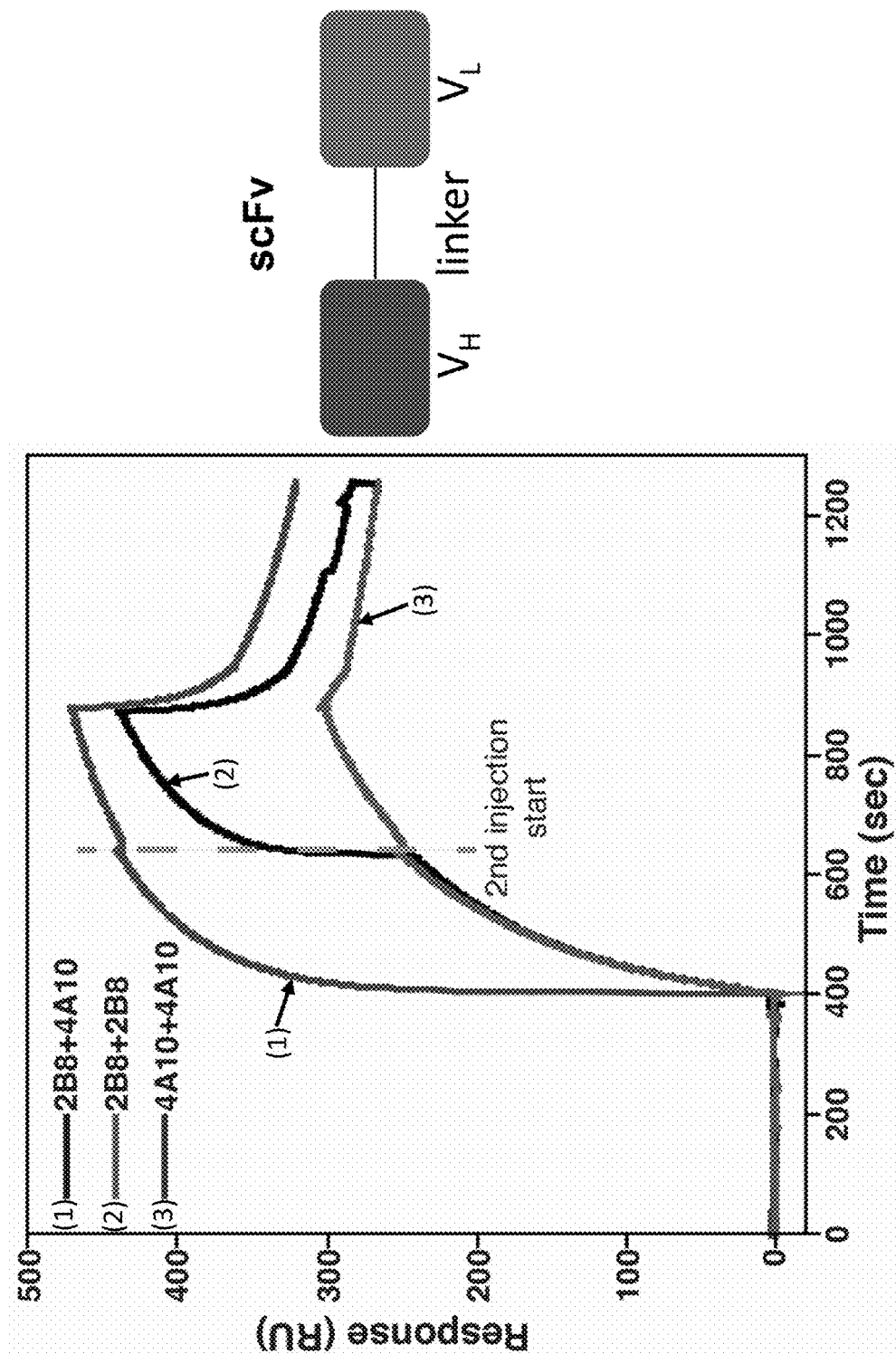
FIG. 5 is a graph illustrating surface plasmon resonance data showing that the 4A10 and 2B8 scFvs bind to non-overlapping epitopes on the IL-7Rα extracellular domain. IL-7Rα ectodomain was coupled to the SPR sensor-chip and binding was assayed by injecting 100 μL (40 μM) of 4A10 or 2B8 scFv to the cassette, followed by another 100 mL (400 mM) of 4A10 or 2B8 scFv. The dashed line indicates the time point when the second scFv solution was injected. An increased response was observed when 2B8 injection was followed by a 4A10 injection, indicating that these two scFvs bind to non-overlapping epitopes on IL-7Rα.

The 4A10 and 2B8 epitopes on IL-7Rα were further evaluated using surface plasmon resonance (FIG. 5). scFvs including the heavy and light chain variable regions of the 4A10 and 2B8 antibodies were prepared and used in the binding assays. The WT IL-7Rα ectodomain was coupled to the SPR sensor-chip and binding was assayed by injecting 100 μL (400 mM) of 4A10 or 2B8 scFv over the sensor-chip, followed by a sequential injection of another 100 μL (40 μM) of 4A10 or 2B8 scFv. The dashed line in FIG. 5 indicates the time point when the second scFv solution was injected. An increased response was observed when 2B8 injection was followed by 4A10 injection, indicating that these two scFvs bind to non-overlapping epitopes on IL-7Rα.

Additional binding studies were performed to show that the 4A10 and 2B8 antibodies bind to IL-7Rα on the cell surface. D1 cells expressing either wild-type human IL-7Rα or mutant human IL-7Rα that includes the P1 mutation were incubated with chimeric antibody including the heavy and light chain variable regions of 4A10 or 2B8, and a human IgG1 constant region, and bound antibody was detected using FACS analysis. As illustrated by the following table, this study shows that the chimeric 4A10 and 2B8 antibodies (in IgG1 format) each bind to IL-7Rα on the cell-surface, and bind to different epitopes on the IL-7Rα ectodomain.

| mAb | Binding to IL-7Rα expressed on D1 cells (arbitrary units) | |
|---|---|---|
| | D1-hIL-7Rα WT | D1-hIL-7Rα P1 |
| 2B8-hIgG1 chimera | 71.1 | 65.5 |
| 4A10-hIgG1 chimera | 76.4 | 77.0 |
| 2B8-hIgG1 chimera + 4A10-hIgG1 chimera | 171.5 | 149.9 |

Additional surface plasmon resonance binding studies were performed to evaluate the binding of the 4A10 and 2B8 antibodies to glycosylated and unglycosylated forms of the IL-7Rα ectodomain. The Fab fragment of the 4A10-hIgG1 chimera was generated using papain cleavage subsequently purified. Binding constants ($K_D$) of 9.2 nM and 91.2 nM were measured for binding of the Fab fragment of the 4A10 MAb to glycosylated and unglycosylated forms of the IL-7Rα ectodomain, respectively. Binding constants ($K_D$) of 1.1 nM and 19.8 nM were measured for binding of the full-length 4A10-hIgG1 chimera to glycosylated and unglycosylated forms of the IL-7Rα ectodomain, respectively. Accordingly, the 4A10 antibody can recognize different glycosylation states of the IL-7Rα, which may be useful as a diagnostic reagent for tissues and fluids.

Figure 6:
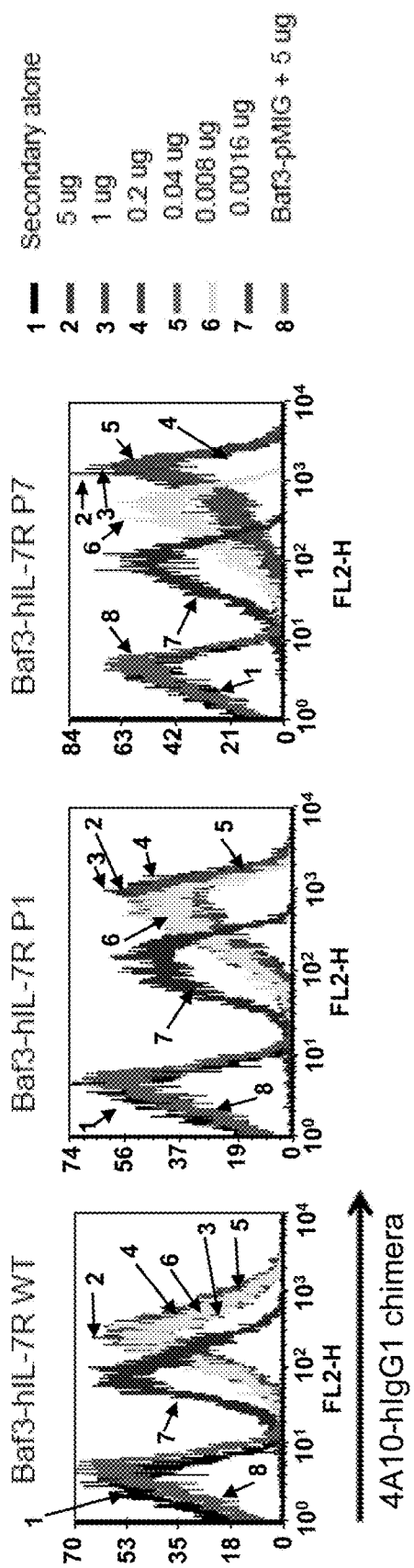
FIG. 6 is a set of graphs showing results of FACS binding assays indicating that a chimeric antibody including the 4A10 heavy and light chain variable regions and human IgG1 constant regions (4A10-hIgG1 chimera) binds wild type and mutant IL-7Rα. The amino acid sequences of the heavy and light chains of the 4A10-hIgG1 chimera are provided as SEQ ID NOs: 21 and 22, respectively. The 4A10-hIgG1 chimera was tested at various concentrations against BaF3 cells transfected with wild-type (WT) IL-7Rα, IL-7Rα including the P1 or P7 gain-of function mutation, or a control (pMIG vector).

Further, the 4A10 antibody was found to bind to human T cells that express human IL-7Rα with and without the "P1" or "P7" gain-of-function mutation (FIG. 6). Additionally, competition assays showed that the 4A10 and 2B8 antibodies do not compete with IL-7 for binding to the IL-7R, and therefore bind to epitopes that do not overlap with the IL-7 binding site on IL-7R.

Figure 7:
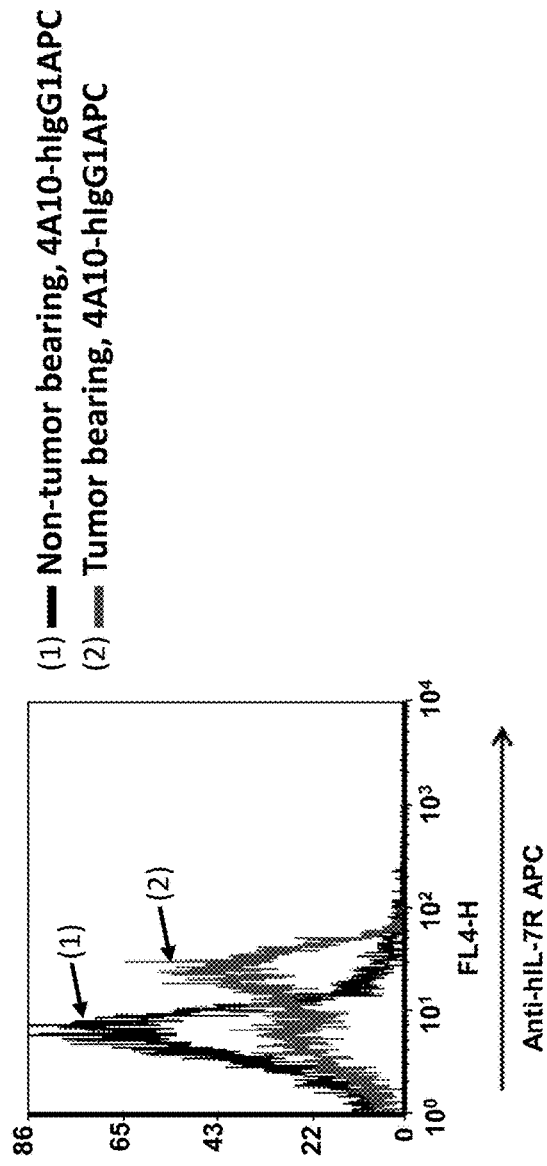
FIG. 7 is a graph showing that the 4A10-hIgG1 chimera binds to human T-ALL cells. A human T-ALL patient sample was expanded in immunodeficient (NSG) mice. Spleen cells were harvested from the mice, and assayed for 4A10-hIgG1 chimera binding using FACS. The 4A10 antibody does not bind to mouse T- or B-cells. Accordingly, 4A10 binding to the human T-ALL cell expanded in the immunodeficient mice and harvested from mouse spleen indicates that this antibody binds to cell-surface IL-7Rα on the human T-ALL cells.

Additionally, the 4A10 antibody binds to human T-ALL cells (FIG. 7). A T-ALL patient sample was transplanted into immunodeficient (NSG) mice. Spleen cells were harvested from the mice, and assayed for 4A10-hIgG1 chimera binding using FACS. The spleen cells were held overnight at 4° C. and blocked with 0.5 μl of 2.4G2 for 20 minutes prior to staining and FACS analysis. Block was present for primary antibody incubation. The 4A10-hIgG1 chimera also stained T cells from normal human blood and macaque blood, as evaluated using FACS binding assays.

Figure 10:
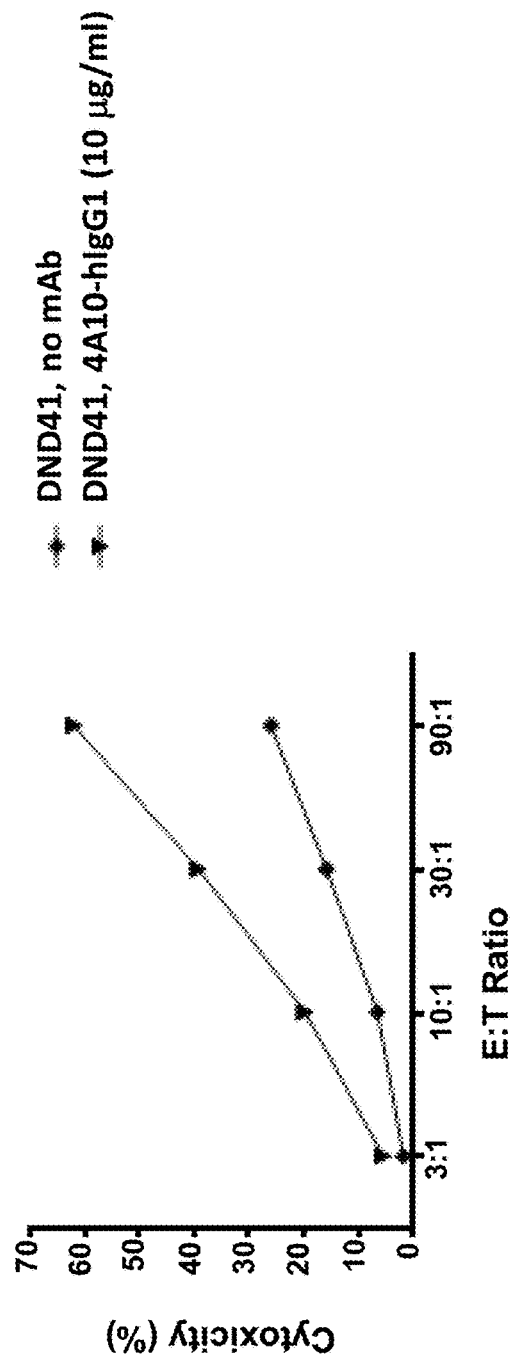
FIG. 10 illustrates that the 4A10-hIgG1 chimera mediates NK-cell ADCC against human DND41 T-ALL cells that express IL-7Rα with a gain-of-function mutation. The cells were incubated with NK cells isolated from human blood at the indicated E:T ratios and with the 4A10-hIgG1 chimera (10 μg/ml). Release of LDH was measured to evaluate cell lysis (cytotoxicity).
Figure 11:
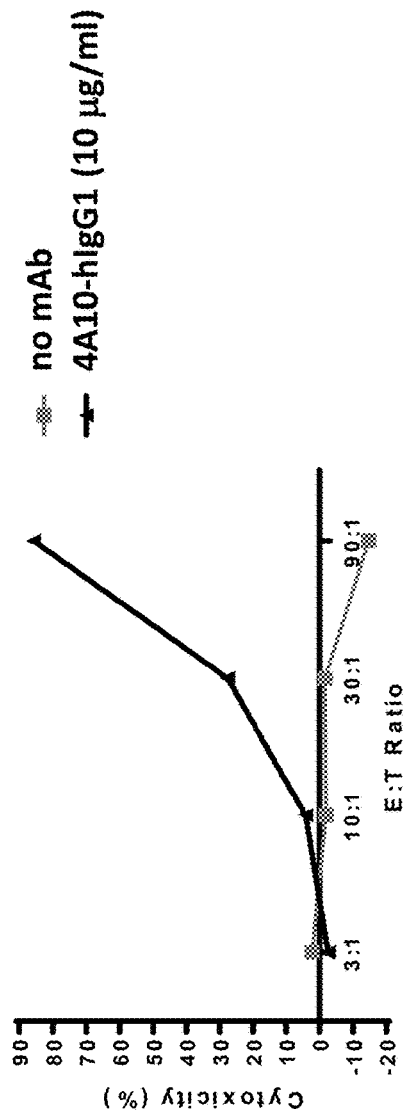
FIG. 11 illustrates that the 4A10-hIgG1 chimera mediates NK-cell ADCC against normal human T cells. The cells were incubated with NK cells isolated from human blood at the indicated E:T ratios and with the 4A10-hIgG1 chimera (10 μg/ml). Release of LDH was measured to evaluate cell lysis (cytotoxicity).

A 4A10-hIgG1 Chimera Mediates ADCC Killing of IL-7Rα Positive Cancer Cells In Vitro An important mechanism for killing leukemia cells can be ADCC, as illustrated by anti-CD20 killing of lymphoma cells. Accordingly, the 4A10-hIgG1 chimera was evaluated for ADCC-mediated killing of IL-7Rα expressing cells (FIG. 8). BaF3 cells (a murine B cell line that does not express IL-7Rα) were incubated with NK cells isolated from human blood and the 4A10-hIgG1 chimera (at 10 μg/ml). LDH release was measured to evaluate cell lysis (killing). As shown in FIG. 8, the 4A10-hIgG1 antibody effectively mediated NK-cell lysis of the BaF3 cells in this in vitro assay. Similar results were obtained using the D1 cells (an IL-7 dependent thymocyte cell line) (FIG. 9). Additionally, the 4A10-hIgG1 chimera mediated NK-cell directed killing of T-ALL cells expressing P1 gain-of-function IL-7Rα (FIG. 10) and normal human T cells (FIG. 11).

Figure 12C:
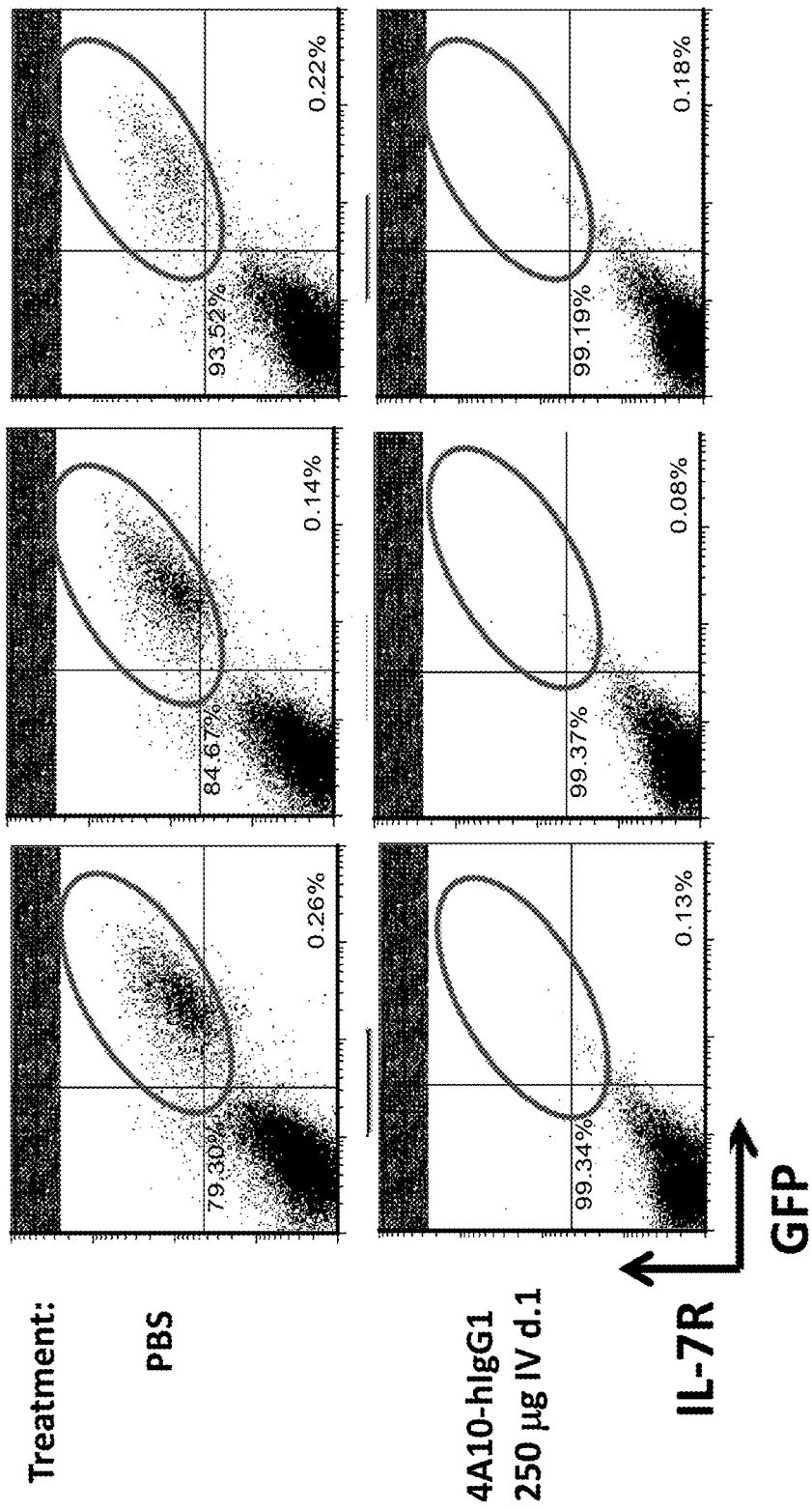
Figure 12E:
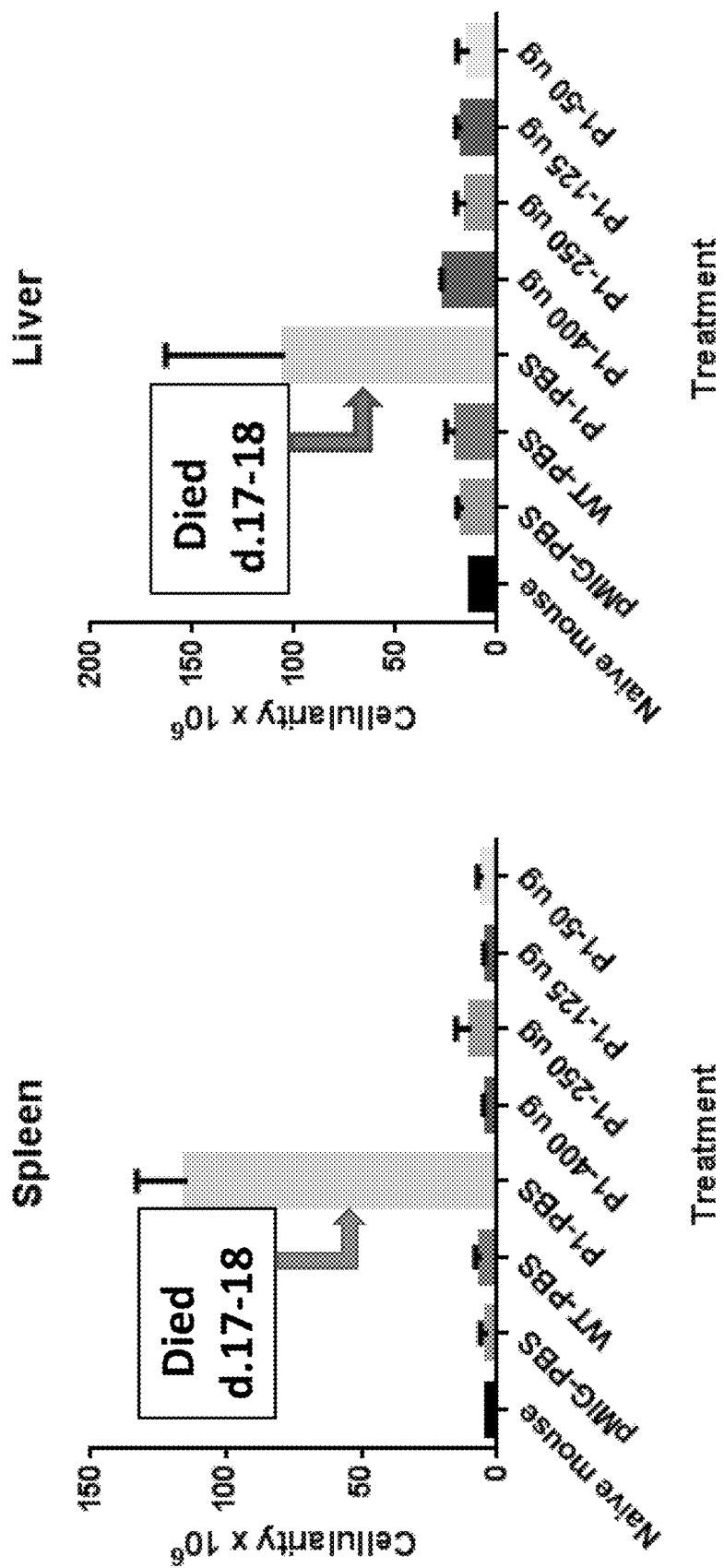
Figure 12F:
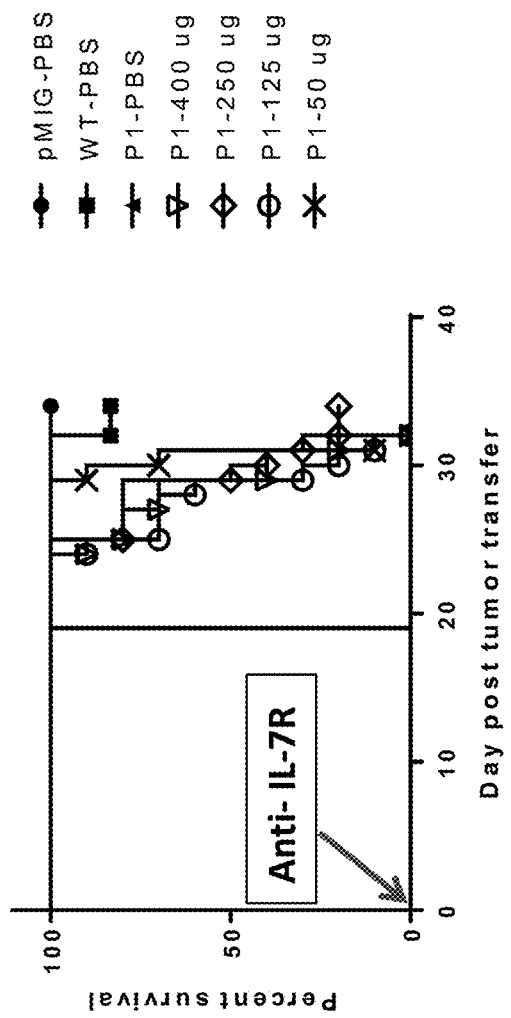
Figure 13A:
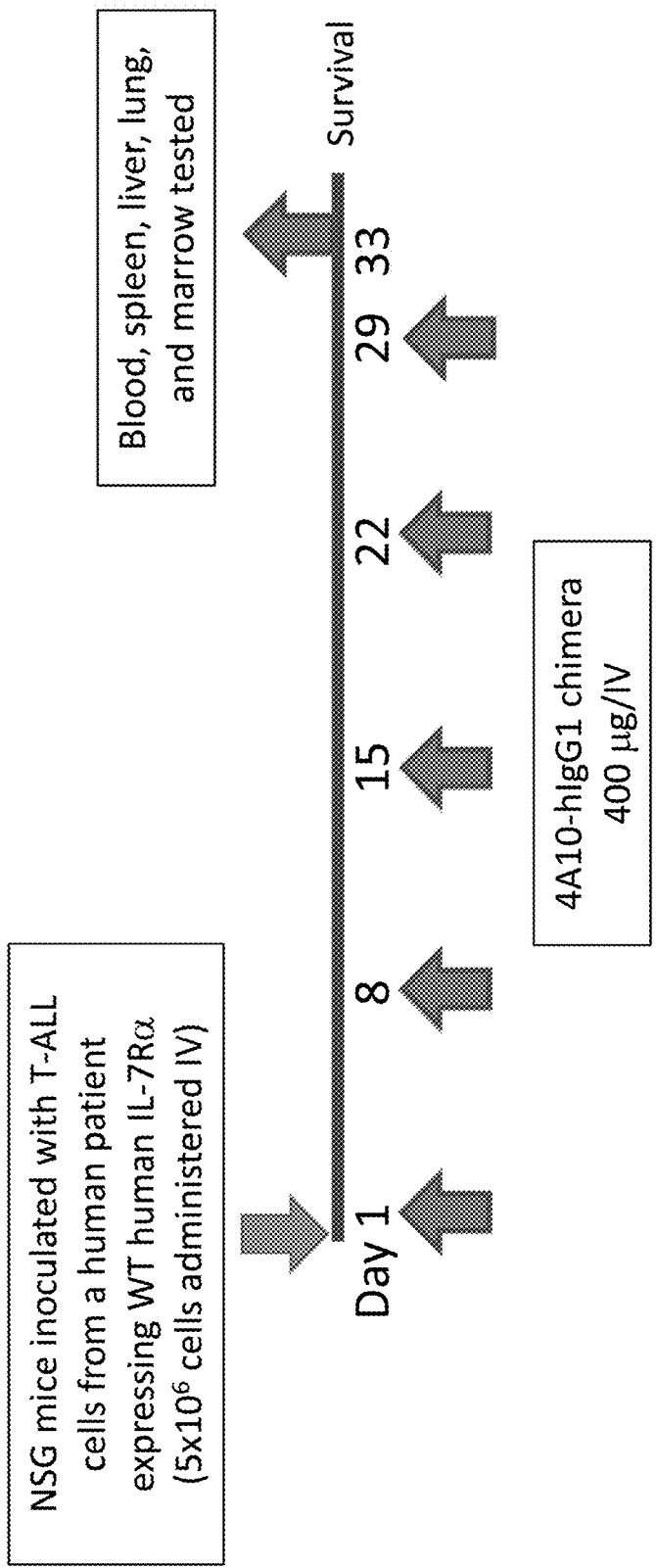
FIGS. 13A-13D illustrate that administration of the 4A10-hIgG1 chimera reduces proliferation of human T-ALL cells expressing WT IL-7Rα in an in vivo assay. (13A) Human T-ALL cells expressing WT IL-7Rα were injected intravenously into immunodeficient NSG mice which lack NK cells as well as T and B cells. 4A10-hIgG1 chimera (400 μg) or PBS (control) were administered intravenously at weekly intervals to the mice totaling five injections. Blood and tissue were sampled at various time points post-inoculation and evaluated by IL-7Rα human CD4 staining to assay T-ALL cell proliferation (FIGS. 13B-13D).
Figure 13B:
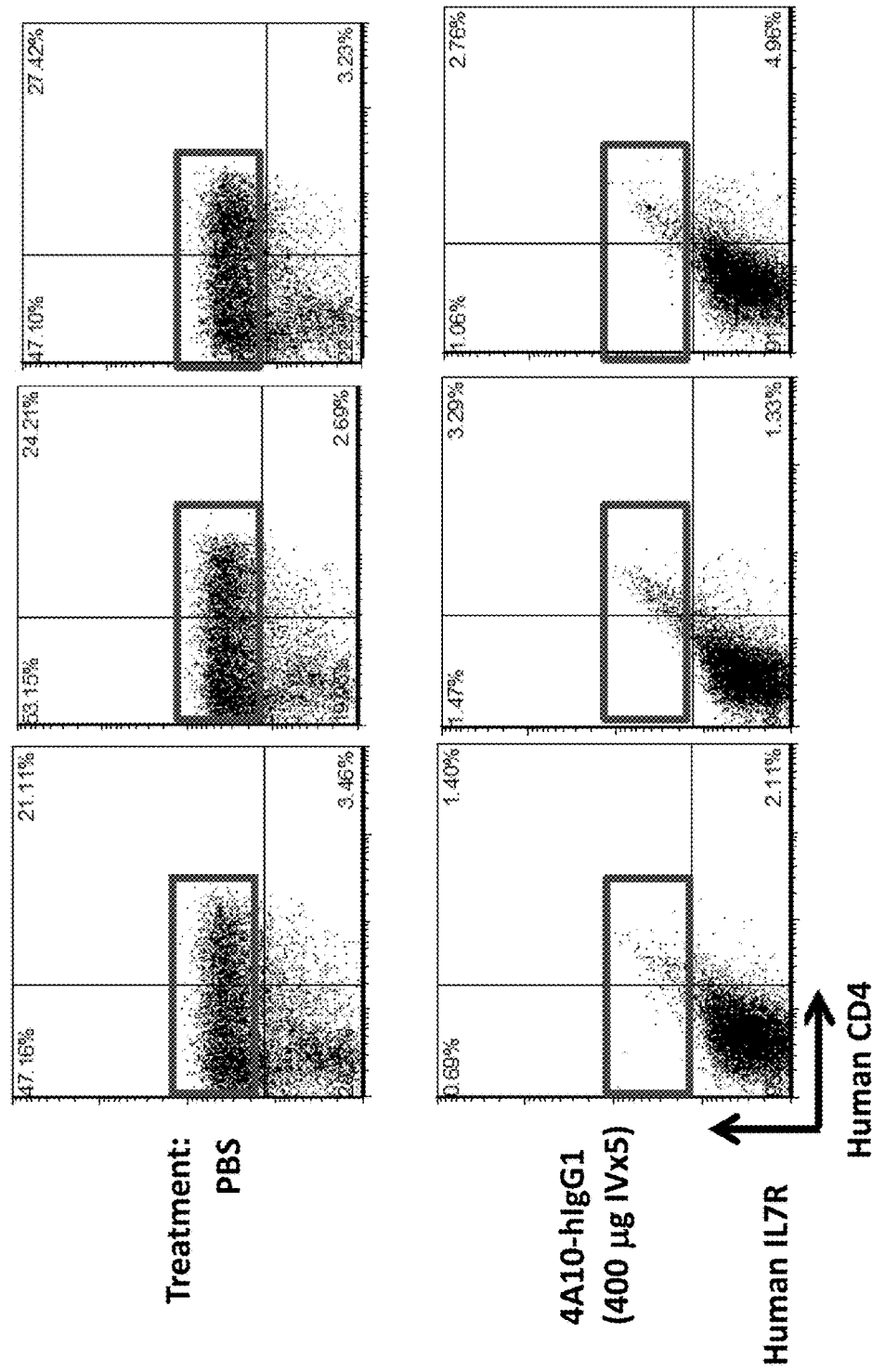
Figure 13C:
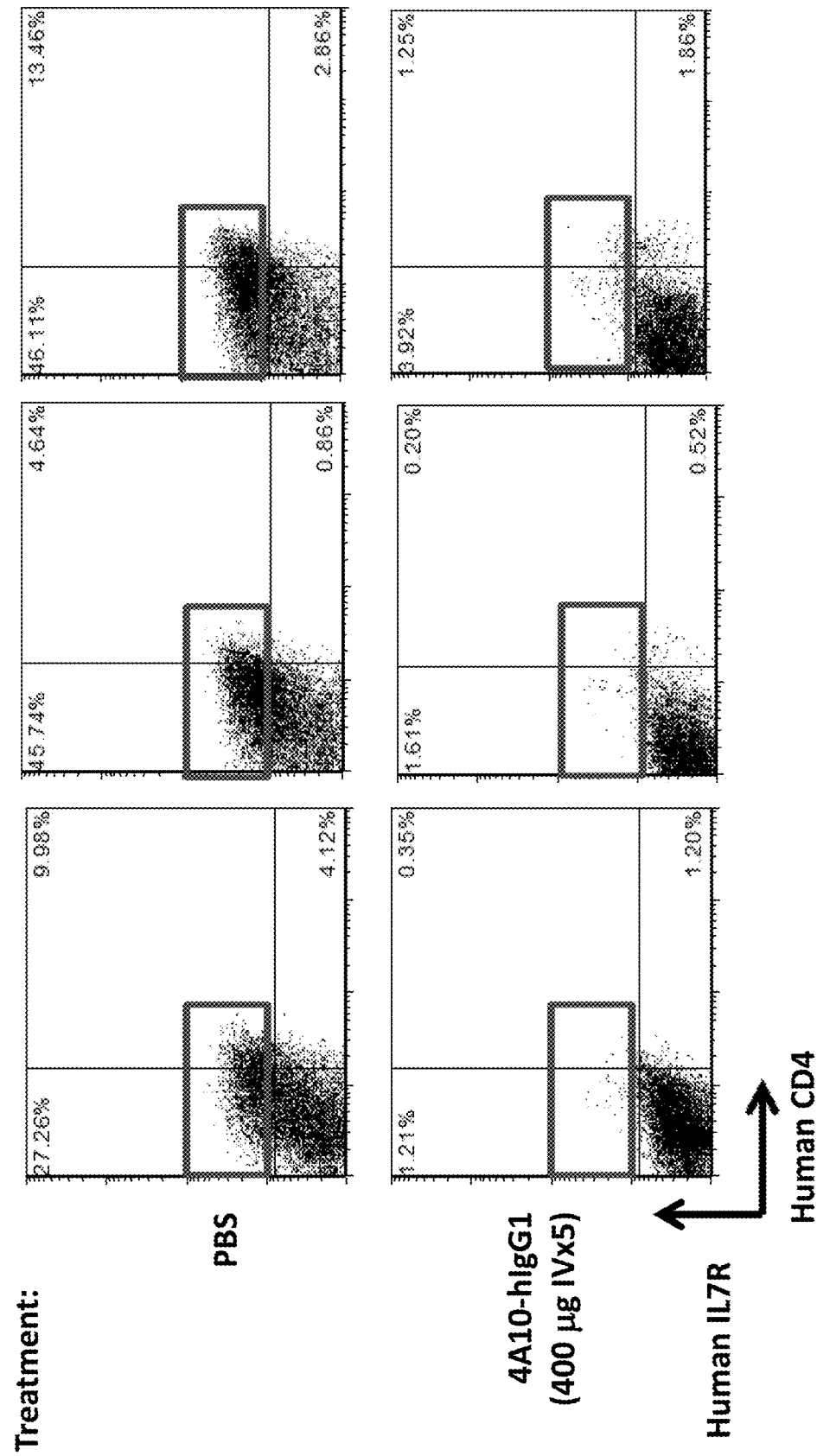
Figure 13D:
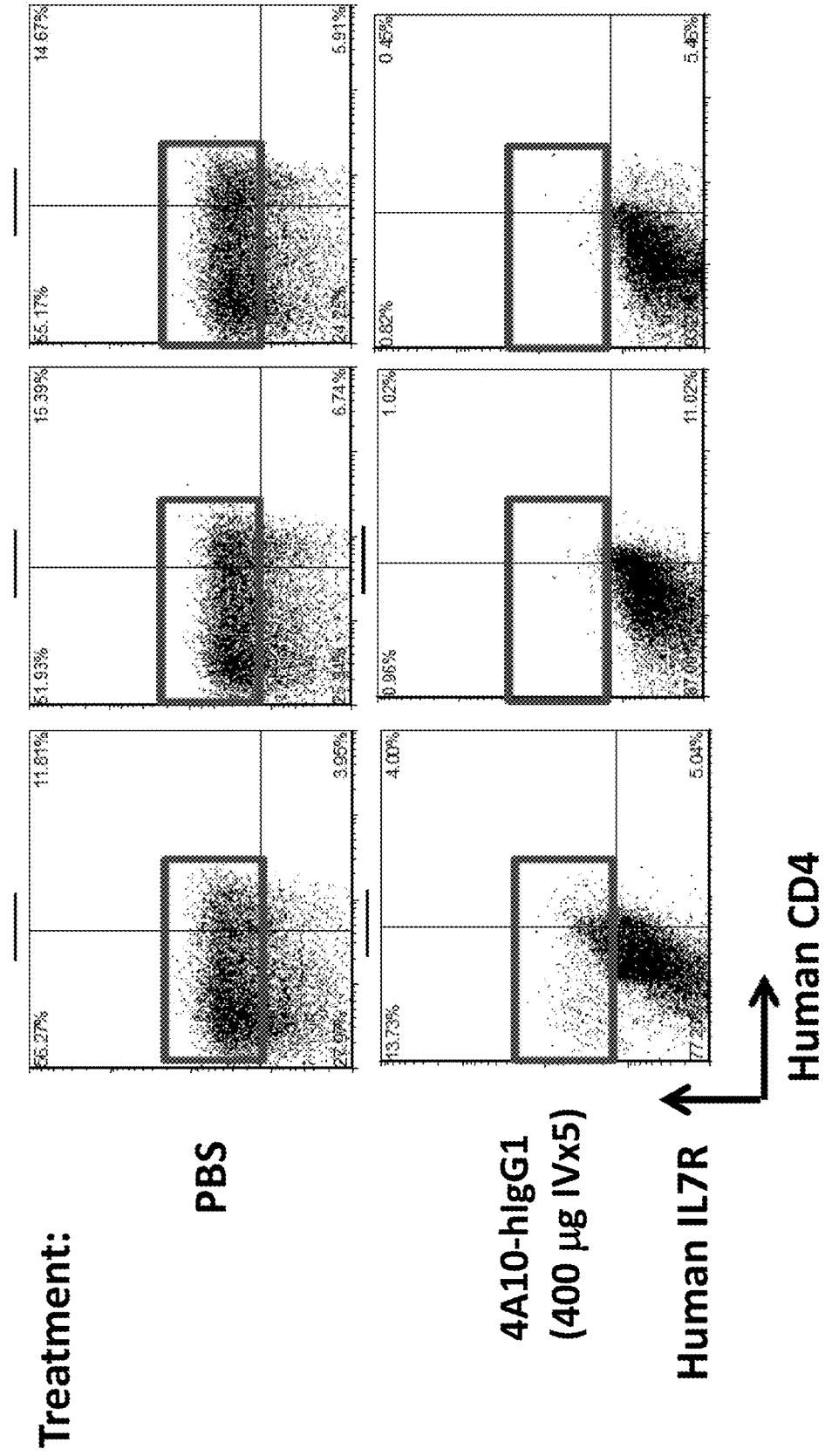

A 4A10-hIgG Chimera Reduces Tumor Burden and Prolongs Survival in In Vivo Models of ALL To evaluate the therapeutic effect of the 4A10-hIgG1 chimera in vivo, a leukemia model was used (FIG. 12). Mutant IL-7Rα P1 was transfected together with GFP into D1 cells (creating a murine lymphoid cell line that grows and metastasizes in mice) and Rag−/− mice were inoculated with the transfected cells (this model was previously described in Zenatti et al., Nat. Genet., 43:932-939, 2011). The day after leukemic cell inoculation, the 4A10-hIgG1 chimera was administered to the mice at various doses. Blood and tissue were sampled at various time point post-inoculation, and the overall survival of the mice was also evaluated. A diagram illustrating the procedure is provided in FIG. 12A. A dramatic reduction in leukemic cells was observed in samples taken on day 15 from spleen (FIG. 12B), bone marrow (FIG. 12C), and liver (FIG. 12 D) in mice administered 250 μg 4A10-hIgG1 chimera by IV compared to the PBS control. FIG. 12E provide a summary of leukemic cell number in spleen and liver at day 19 from various experimental conditions. Finally, as shown in FIG. 12F, a single injection of the 4A10-hIgG1 chimera prolonged survival of mice inoculated with the IL-7Rα transformed D1 cells. Control mice not receiving MAb died on day 17 and 18.

To further evaluate the therapeutic effect of the 4A10-hIgG1 chimera in vivo, an additional leukemia model was used (FIG. 13). Immunodeficient (NSG) mice were inoculated with T-ALL cells with a WT IL-7Rα gene that were harvested from a human patient ($5 \times 10^6$ were administered IV). NSG mice lack NK, T and B cells. The 4A10-hIgG1 chimera (400 μg) was administered to the mice intravenously at weekly intervals totaling five injections. Blood and tissue were sampled at various time point post-inoculation, and the overall survival of the mice was also evaluated. A diagram illustrating the procedure is provided in FIG. 13A. A dramatic reduction in T cells (detected by human IL-7R and CD4 staining) was observed in samples taken on day 33 from spleen (FIG. 13B), blood (FIG. 13C) and liver (FIG. 13D), but depletion was incomplete in NSG bone marrow samples, from mice treated with the 4A10-hIgG1 compared to the PBS control. Surprisingly, the Mab showed efficacy in controlling human T-ALL growth, in the absence of NK cells, at multiple sites (FIG. 13). However, bone marrow harbored viable T-ALL cells in treated NSG mice.

Figure 14A:
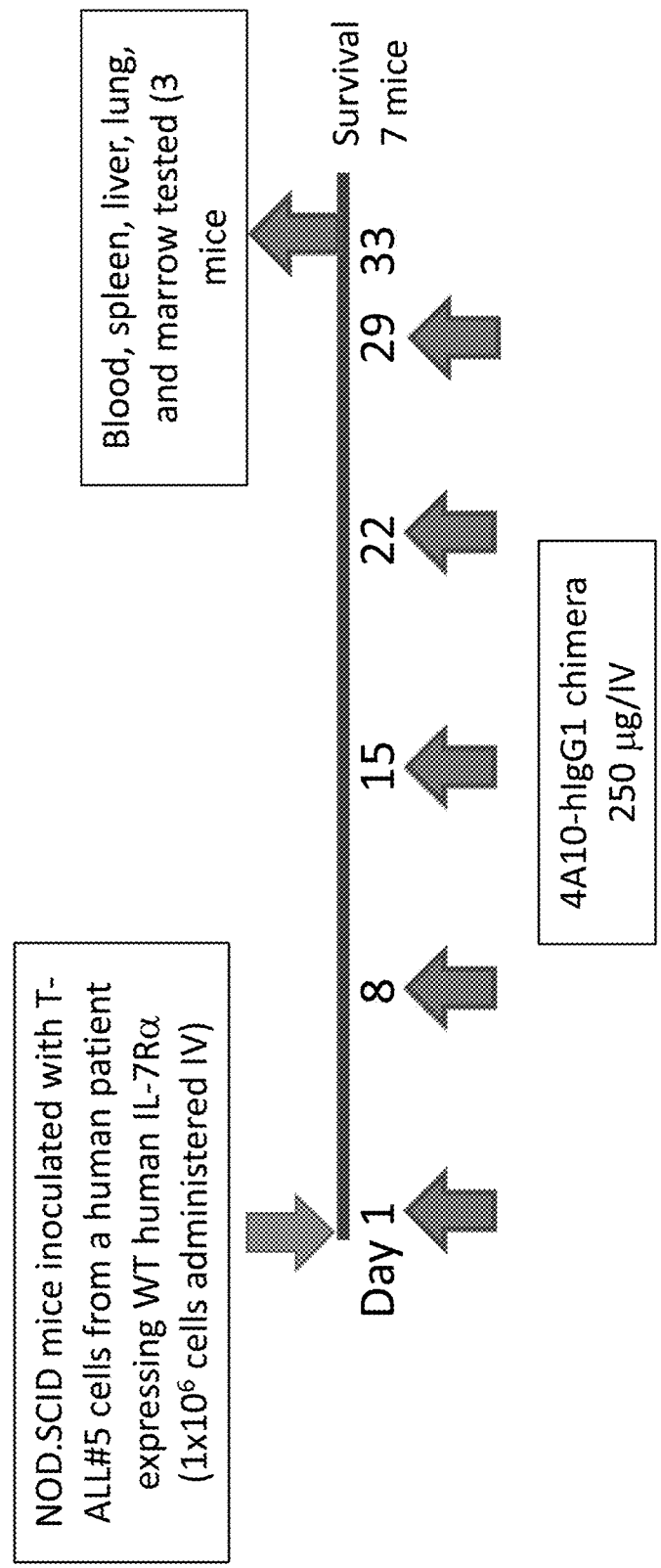
Figure 14C:
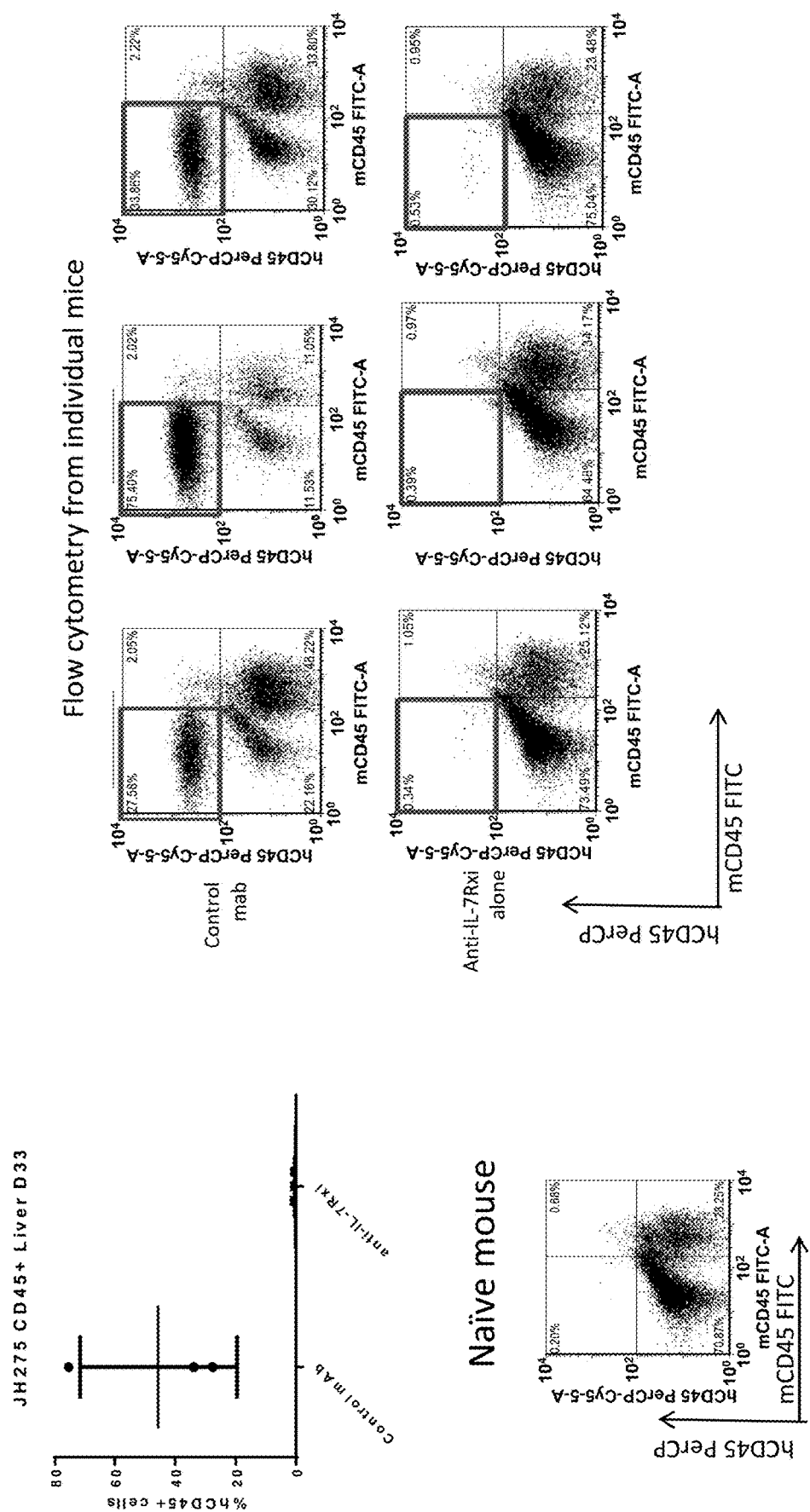
Figure 14E:
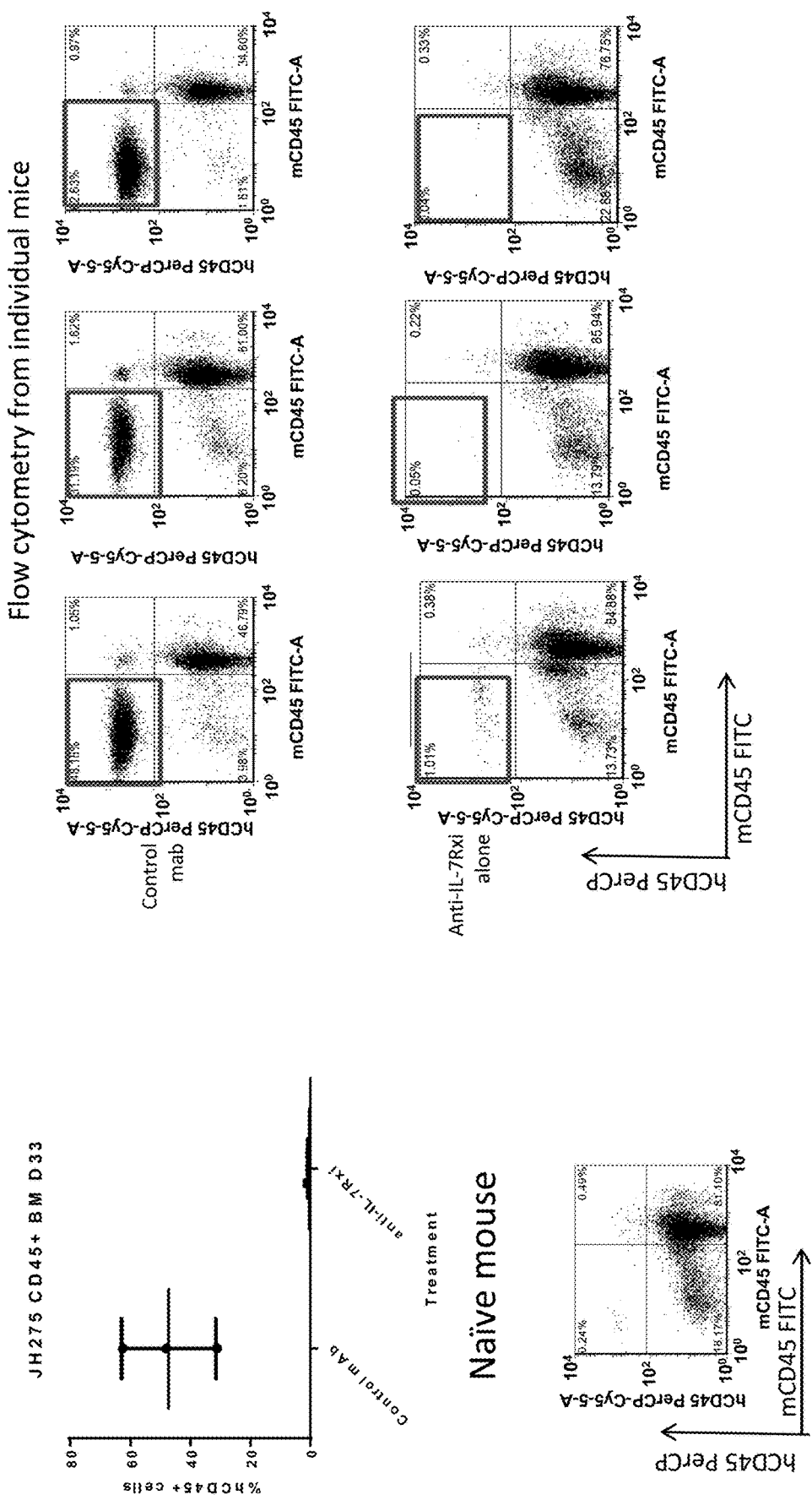
Figure 14F:
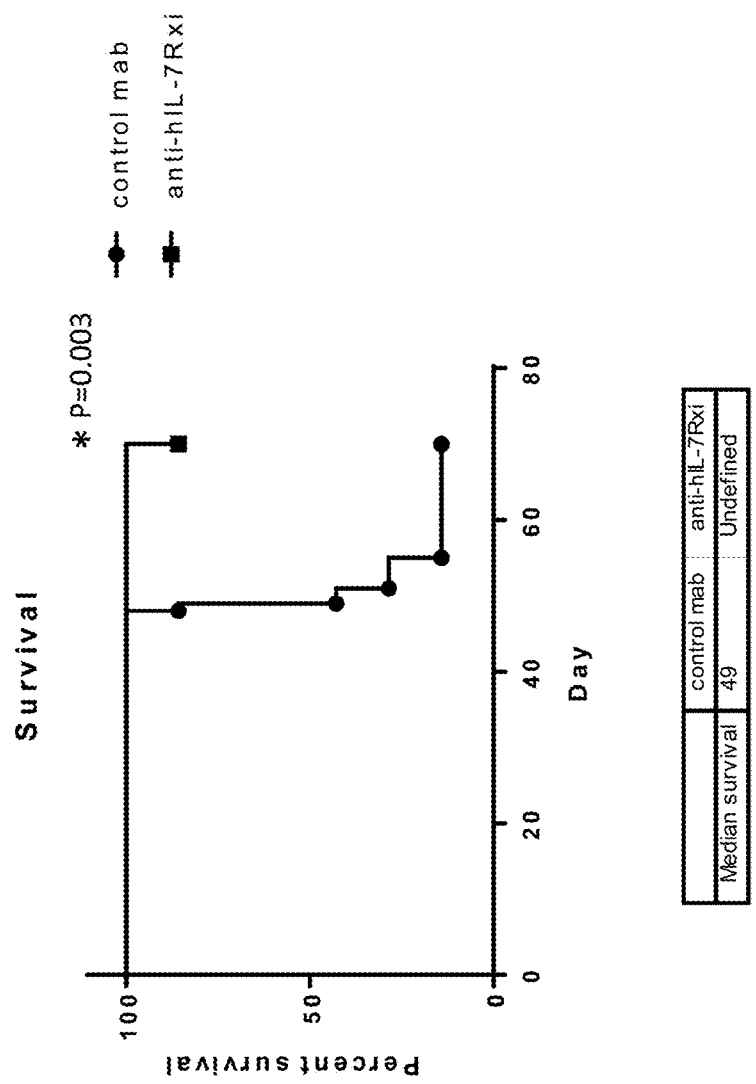
Figure 15:
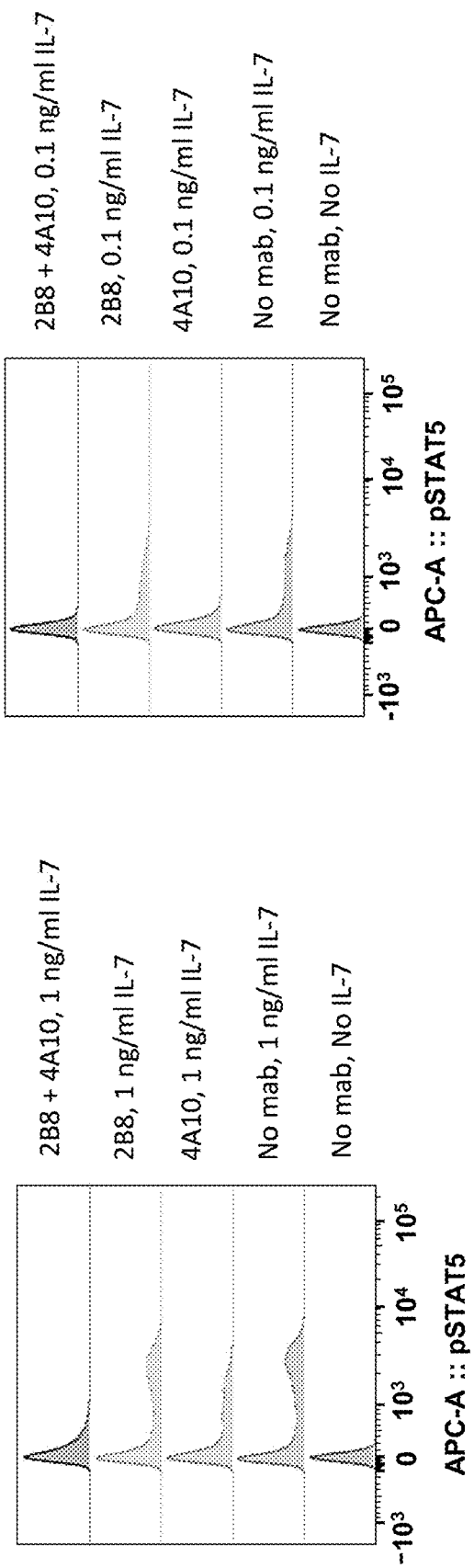
FIG. 15 is a set of graphs showing that anti-IL-7Rα antibodies can inhibit IL-7 signaling in IL-7Rα positive T-ALL cells. IL-7Rα positive T-ALL cells were treated with IL-7 and the indicated antibodies, and evaluated for pSTAT-5 induction, which is induced following IL-7 activation of IL-7R.

Additional assays were performed to show that NK cells promote the efficacy of anti-IL-7R treatment of T-ALL. These assays were performed to evaluate use of the 4A10-hIgG1 chimeric mAb to reduce xenografted human T-ALL cells in the presence of NK cells. The assays used NOD/Scid mice, which have NK cells but are deficient in T and B cells. Mice harboring human T-ALL cells were treated with weekly injections of the 4A10-hIgG1 chimeric mAb (FIG. 14A). Treatment was highly effective in blood, liver, lung, and most importantly bone marrow (FIGS. 14B-14E), the latter site having shown resistance to treatment in the absence of NK cells. Further, a significant increase in survival with the mAb treatment was observed (FIG. 14F). IL-7Rα Antibodies Inhibit IL-7 Signaling in T-ALL Cells Additional in vitro assays were performed to show that chimeric mAbs have inhibitory effects on IL-7-induced signaling. T-ALL cells respond to IL-7 and induce phosphorylation of STAT5, an early signaling molecule. For these assays, T-ALL #5 cells were isolated from engrafted NSG spleen. The cells cultured with anti-IL-7Rα antibody for 2 hours at 4 C, followed by stimulated with hIL-7 for 20 minutes and evaluation using flow cytometry (ICFC) for pSTAT-5. The 4A10-hIgG1 chimeric mAb blocked IL-7-induced pSTAT5 response at the lower dose of IL-7 (FIG. 15, right panel) and partially blocked at the higher dose of IL-7 (FIG. 15, left panel). In contrast, the 2B8 mAb had no inhibitory activity on its own, but cooperated with the 4A10-hIgG1 chimeric mAb to block signaling at the higher dose of IL-7 (FIG. 15, left panel). As noted above, 4A10 and 2B8 bind non-overlapping epitopes on IL-7R. This data shows that 4A10 alone inhibits IL-7R signaling at low IL-7 doses and cooperates with 2B8 at high doses, suggesting future therapeutics could combine the two antibodies. Thus, one non-limiting explanation for the inhibitory effect of the 4A10-hIgG1 chimera on T-ALL in mice lacking NK cells is that this effect is due to inhibiting survival signals from the low levels of IL-7 found in vivo.

Another approach to determine whether anti-IL-7R antibodies can inhibit T-ALL in vivo, independent of ADCC would be to test the effect of the original mouse 4A10 antibodies. These contain the mouse IgG1 constant region which cannot mediate ADCC, unlike the ADCC-mediating chimeric antibodies. These experiments are ongoing, but so far there is a substantial inhibitory effect of the original 4A10 mouse Mab on a T-ALL xenograft.

In summary, the data provided in this example illustrate the specific binding activity of the 4A10 and 2B8 antibodies for IL-7Rα, and the in vivo efficacy of the 4A10 antibody for treating leukemias that express IL-7Rα, such as T-ALL.

Example 2. Combination Therapy with IL-7Rα Specific Monoclonal Antibody and CXCR4 Antagonist Synergistically Depletes T-ALL Cells from Bone Marrow This example illustrates that IL-7Rα mAb and CXCR4 antagonist combination therapy synergistically reduces T-ALL cells from bone marrow.

Prior studies showed that the C—X—C chemokine receptor type 4 is essential for leukemia-initiating cell (LIC) activity, including for T-ALL cells, and proposed CXCR4 antagonists for treatment of T-ALL (see e.g., Passaro et al., Cancer Cell, 27(6):769-779, 2015). To determine if CXCR4 antagonists and IL-7Rα specific antibodies could act in combination to reduce T-ALL, combination therapy including the 4A10-hIgG1 chimeric antibody and a CXCR4 antagonist (AMD3100) was tested in a T-ALL xenograft model using immunodeficient mice. The mice received 10 mg/kg of AMD3100 subcutaneously Monday through Friday.

Surprisingly, combing the CXCR4 antagonist (AMD3100) together with 4A10-hIgG1 chimeric antibody was highly effective in and synergistically depleted leukemia cells from bone marrow (see FIG. 16).

Example 3: IL-7Rα-Specific Monoclonal Antibodies for Detecting Cancer in a Subject or Confirming the Diagnosis of Cancer in a Subject This example describes the use of IL-7Rα-specific monoclonal antibodies (such as an antibody with the CDRs of the 4A10 or 2B8 mAb as disclosed herein) for the detection of cancer in a subject. This example further describes the use of these antibodies to confirm the diagnosis of cancer in a subject.

A blood or tissue sample (such as a biopsy) is obtained from the patient diagnosed with, or suspected of having an IL-7Rα-positive cancer (i.e., a cancer that overexpresses IL-7Rα, or overexpresses IL-7Rα activity, such as ALL, for example, T-ALL or B-ALL). A sample taken from a patient that does not have cancer can be used as a control. An immunoassay (such as immunohistochemistry or fluorescence in situ hybridization of a tissue sample) is performed to detect the presence of IL-7Rα in the sample (such as IL-7Rα-expressing cells in a tissue sample). For example, tissue sections obtained from a patient biopsy and a control tissue sample are contacted with an IL-7Rα-specific monoclonal antibody directly conjugated with a detectable label (such as an enzyme) and immunohistochemical detection for IL-7Rα is carried out according to standard procedures. An increase in enzyme activity of the patient sample, relative to the control sample, indicates the anti-IL-7Rα antibody specifically bound proteins from the tissue sample, thus detecting the presence of IL-7Rα protein in the sample. Detection of IL-7Rα protein in the patient sample indicates the patient has an IL-7Rα-positive cancer, or confirms diagnosis of cancer in the subject.

Example 4: Treatment of T-ALL in a Subject

This example describes a particular method that can be used to treat a cancer that expresses IL-7Rα in humans by administration of a chimeric antibody including the CDRs of the 4A10 or 2B8 antibody and/or the $V_H$ and $V_L$ of the 4A10 or 2B8 antibody, and a human IgG1 constant region. Although particular methods, dosages, and modes of administrations are provided, one skilled in the art will appreciate that variations can be made without substantially affecting the treatment.

In this example, patients diagnosed with T-ALL are administered the chimeric antibody. Preparation of the chimeric antibody is performed according to standard methods. In some patients, the chimeric antibody is administered by intravenous infusion every three weeks. The dose of the chimeric antibody administered to a patient varies depending on the weight and gender of the patient, and mode and time course of administration. In some cases, the chimeric antibody is administered at a dose of about 1 to about 5 mg/kg. Following treatment, patients are evaluated for cancer progression (including cancer growth and metastasis) and other clinical signs of illness.

It will be apparent that the precise details of the methods or compositions described may be varied or modified without departing from the spirit of the described embodiments. We claim all such modifications and variations that fall within the scope and spirit of the claims below.

We claim:

1. A method of treating a subject with an IL-7Rα positive cancer, comprising:
   administering to the subject a therapeutically effective amount of:
   (A) a monoclonal antibody that specifically binds to an extracellular domain of IL-7Rα, the monoclonal antibody comprising:
   a heavy chain variable region ($V_H$) comprising a heavy chain complementarity determining region (HCDR) 1, a HCDR2, and a HCDR3 of the $V_H$ set forth as SEQ ID NO: 1 (4A10 $V_H$) and a light chain variable region ($V_L$) comprising a light chain complementarity determining region (LCDR)1, a LCDR2, and a LCDR3 of the $V_L$ set forth as SEQ ID NO: 2 (4A10 $V_L$), or
   a $V_H$ comprising a HCDR1, a HCDR2, and a HCDR3 of the $V_H$ set forth as SEQ ID NO: 3 (2B8 $V_H$) and a $V_L$ comprising a LCDR1, a LCDR2, and a LCDR3 of the $V_L$ set forth as SEQ ID NO: 4 (2B8 $V_L$);
   (B) an antigen binding fragment of the monoclonal antibody; (C) a bispecific antibody comprising the monoclonal antibody or the antigen binding fragment; or (D) an antibody-drug conjugate comprising the monoclonal antibody or the antigen binding fragment of the monoclonal antibody thereby treating the IL-7Rα positive cancer in the subject, wherein the IL-7Rα positive cancer is a solid tumor.

2. The method of claim 1, wherein the HCDR1, the HCDR2, the HCDR3, the LCDR1, the LCDR2, and the LCDR3 comprise the amino acid sequences set forth as SEQ ID NOs: 5, 6, 7, 8, 9, and 10, respectively (4A10 kabat CDRs) or the amino acid sequences set forth as SEQ ID NOs: 11, 12, 13, 14, 15, and 16, respectively (2B8 kabat CDRs).

3. The method of claim 1, wherein the $V_H$ and $V_L$ comprise the amino acid sequences set forth as SEQ ID NOs: 1 and 2, respectively, or the amino acid sequences set forth as SEQ ID NOs: 3 and 4, respectively.

4. The method of claim 1, wherein the $V_H$ and the $V_L$ are encoded by the nucleic acid sequences set forth as SEQ ID NOs: 25 and 26, respectively, or SEQ ID NOs: 27 and 28, respectively.

5. The method of claim 1, wherein the monoclonal antibody comprises human framework regions and/or a human constant region.

6. The method of claim 1, wherein the monoclonal antibody is an IgG, IgM, or IgA.

7. The method of claim 1, wherein the monoclonal antibody is an IgG1 and comprises a human constant region.

8. The method of claim 7, wherein the monoclonal antibody comprises a heavy chain and a light chain comprising the amino acid sequences set forth as SEQ ID NOs: 21 and 22, respectively, or SEQ ID NOs: 23 and 24, respectively.

9. The method of claim 1, wherein the monoclonal antibody comprises a constant region comprising a modification that increases binding to the neonatal Fc receptor and/or increases antibody-dependent cell cytotoxicity (ADCC).

10. The method of claim 1, wherein the monoclonal antibody mediates ADCC killing of IL-7Rα positive cells.

11. The method of claim 1, comprising administering the monoclonal antibody to the subject.

12. The method of claim 1, comprising administering the antigen binding fragment to the subject.

13. The method of claim 1, comprising administering the bispecific antibody to the subject.

14. The method of claim 1, further comprising administering to the subject a therapeutically effective amount of a C—X—C chemokine receptor type 4 (CXCR4) antagonist.

15. The method of claim 14, wherein the CXCR4 antagonist is AMD3100.

16. The method of claim 1, comprising treating the subject with the IL-7Rα positive cancer.

17. The method of claim 1, comprising administering the antibody-drug conjugate to the subject.

18. The method of claim 17, wherein the drug is Monomethyl Auristatin E (MMAE), cisplatin, or maytansine.

19. The method of claim 17, wherein the drug is a radioactive compound.

20. The method of claim 17, comprising administering the antibody-drug conjugate intravenously or subcutaneously to the subject.

21. The method of claim 16, wherein the IL-7Rα positive cancer comprises a mutation in the IL-7 pathway that increases proliferation.

22. The method of claim 21, wherein the mutation is a gain-of-function mutation in the gene encoding IL-7Rα that leads to increased phosphorylation of Stat5b compared to control.

23. The method of claim 1, wherein the IL-7Rα positive cancer is a sarcoma or a carcinoma.

24. The method of claim 1, wherein the IL-7Rα positive cancer is an ovarian cancer, a colon cancer, a pancreatic cancer, a lung cancer, a squamous cell carcinoma, a renal cell carcinoma, bladder carcinoma, or a melanoma.

* * * * *

SEQUENCE LISTING

<160> NUMBER OF SEQ ID NOS: 49

<210> SEQ ID NO 1
<211> LENGTH: 122
<212> TYPE: PRT
<213> ORGANISM: Artificial Sequence
<220> FEATURE:
<223> OTHER INFORMATION: antibody sequence

<400> SEQUENCE: 1

Gln Val Gln Leu Gln Gln Pro Gly Ala Glu Leu Val Met Pro Gly Ala
1               5                   10                  15

Ser Val Lys Leu Ser Cys Lys Ala Ser Gly Tyr Thr Phe Thr Ser Tyr
                20                  25                  30

Trp Met His Trp Val Lys Gln Arg Pro Gly Glu Gly Leu Glu Trp Ile
            35                  40                  45

Gly Glu Ile Asp Pro Ser Asp Ser Tyr Thr Asn Asp Asn Gln Lys Phe
        50                  55                  60

Lys Gly Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Arg Leu Tyr Ser Asn Ser Tyr Tyr Tyr Ala Met Asp Tyr Trp
                100                 105                 110

Gly Gln Gly Thr Ser Val Thr Val Ser Ser
            115                 120

<210> SEQ ID NO 2
<211> LENGTH: 106
<212> TYPE: PRT
<213> ORGANISM: Artificial Sequence
<220> FEATURE:
<223> OTHER INFORMATION: antibody sequence

<400> SEQUENCE: 2

Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Lys Lys Tyr
                20                  25                  30

Ile Ala Trp Tyr Gln His Lys Pro Gly Lys Gly Pro Arg Leu Leu Ile
            35                  40                  45

His Tyr Thr Ser Thr Leu Gln Pro Gly Ile Pro Ser Arg Phe Ser Gly
        50                  55                  60

Ser Gly Ser Gly Arg Asp Tyr Ser Phe Ser Ile Ser Asn Leu Glu Pro
65                  70                  75                  80

Val Asp Ile Ala Thr Tyr Tyr Cys Leu Gln Tyr Asp Asn Leu Leu Thr
                85                  90                  95

Phe Gly Ala Gly Thr Lys Leu Glu Leu Lys
            100                 105

<210> SEQ ID NO 3
<211> LENGTH: 120
<212> TYPE: PRT
<213> ORGANISM: Artificial Sequence
<220> FEATURE:
<223> OTHER INFORMATION: antibody sequence

<400> SEQUENCE: 3

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Ser Asp Tyr
             20                  25                  30

Tyr Met His Trp Val Lys Gln Ser His Gly Lys Ser Leu Glu Trp Ile
         35                  40                  45

Gly Tyr Ile Tyr Pro Asp Asn Gly Asn Gly Tyr Asn Gln Lys Phe
 50                  55                  60

Lys Gly Lys Ala Thr Leu Thr Val Asp Lys Ser Ser Thr Val Tyr
65                  70                  75                  80

Met Glu Leu Arg Ser Leu Thr Ser Glu Asp Ser Ala Leu Tyr Tyr Cys
             85                  90                  95

Ala Arg Gly Thr Tyr Tyr Asp Gly Ser Tyr Phe Asp Tyr Trp Gly Gln
            100                 105                 110

Gly Thr Thr Leu Thr Val Ser Ser
        115                 120

<210> SEQ ID NO 4
<211> LENGTH: 107
<212> TYPE: PRT
<213> ORGANISM: Artificial Sequence
<220> FEATURE:
<223> OTHER INFORMATION: antibody sequence

<400> SEQUENCE: 4

Asp Ile Val Met Thr Gln Ser His Lys Phe Met Ser Thr Leu Val Gly
1               5                   10                  15

Asp Arg Val Ser Ile Thr Cys Lys Ala Ser Gln Asp Val Ser Thr Thr
             20                  25                  30

Val Ala Trp Tyr Gln Gln Lys Pro Gly Gln Ser Pro Lys Leu Leu Ile
         35                  40                  45

Tyr Ser Ala Ser Tyr Arg Tyr Thr Gly Val Pro Asp Arg Phe Thr Gly
 50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Ile Pro Arg
             85                  90                  95

Thr Phe Gly Gly Gly Thr Lys Leu Glu Ile Lys
            100                 105

<210> SEQ ID NO 5
<211> LENGTH: 5
<212> TYPE: PRT
<213> ORGANISM: Artificial Sequence
<220> FEATURE:
<223> OTHER INFORMATION: antibody sequence

<400> SEQUENCE: 5

Ser Tyr Trp Met His
1               5

<210> SEQ ID NO 6
<211> LENGTH: 17
<212> TYPE: PRT
<213> ORGANISM: Artificial Sequence
<220> FEATURE:
<223> OTHER INFORMATION: antibody sequence

<400> SEQUENCE: 6

Glu Ile Asp Pro Ser Asp Ser Tyr Thr Asn Asp Asn Gln Lys Phe Lys
1               5                   10                  15

Gly

```
<210> SEQ ID NO 7
<211> LENGTH: 13
<212> TYPE: PRT
<213> ORGANISM: Artificial Sequence
<220> FEATURE:
<223> OTHER INFORMATION: antibody sequence

<400> SEQUENCE: 7

Arg Leu Tyr Ser Asn Ser Tyr Tyr Tyr Ala Met Asp Tyr
1               5                   10

<210> SEQ ID NO 8
<211> LENGTH: 11
<212> TYPE: PRT
<213> ORGANISM: Artificial Sequence
<220> FEATURE:
<223> OTHER INFORMATION: antibody sequence

<400> SEQUENCE: 8

Lys Ala Ser Gln Asp Ile Lys Lys Tyr Ile Ala
1               5                   10

<210> SEQ ID NO 9
<211> LENGTH: 7
<212> TYPE: PRT
<213> ORGANISM: Artificial Sequence
<220> FEATURE:
<223> OTHER INFORMATION: antibody sequence

<400> SEQUENCE: 9

Tyr Thr Ser Thr Leu Gln Pro
1               5

<210> SEQ ID NO 10
<211> LENGTH: 8
<212> TYPE: PRT
<213> ORGANISM: Artificial Sequence
<220> FEATURE:
<223> OTHER INFORMATION: antibody sequence

<400> SEQUENCE: 10

Leu Gln Tyr Asp Asn Leu Leu Thr
1               5

<210> SEQ ID NO 11
<211> LENGTH: 5
<212> TYPE: PRT
<213> ORGANISM: Artificial Sequence
<220> FEATURE:
<223> OTHER INFORMATION: antibody sequence

<400> SEQUENCE: 11

Asp Tyr Tyr Met His
1               5

<210> SEQ ID NO 12
<211> LENGTH: 17
<212> TYPE: PRT
<213> ORGANISM: Artificial Sequence
<220> FEATURE:
<223> OTHER INFORMATION: antibody sequence

<400> SEQUENCE: 12

Tyr Ile Tyr Pro Asp Asn Gly Gly Asn Gly Tyr Asn Gln Lys Phe Lys
1               5                   10                  15
```

Gly

<210> SEQ ID NO 13
<211> LENGTH: 11
<212> TYPE: PRT
<213> ORGANISM: Artificial Sequence
<220> FEATURE:
<223> OTHER INFORMATION: antibody sequence

<400> SEQUENCE: 13

Gly Thr Tyr Tyr Asp Gly Ser Tyr Phe Asp Tyr
1               5                   10

<210> SEQ ID NO 14
<211> LENGTH: 11
<212> TYPE: PRT
<213> ORGANISM: Artificial Sequence
<220> FEATURE:
<223> OTHER INFORMATION: antibody sequence

<400> SEQUENCE: 14

Lys Ala Ser Gln Asp Val Ser Thr Thr Val Ala
1               5                   10

<210> SEQ ID NO 15
<211> LENGTH: 7
<212> TYPE: PRT
<213> ORGANISM: Artificial Sequence
<220> FEATURE:
<223> OTHER INFORMATION: antibody sequence

<400> SEQUENCE: 15

Ser Ala Ser Tyr Arg Tyr Thr
1               5

<210> SEQ ID NO 16
<211> LENGTH: 9
<212> TYPE: PRT
<213> ORGANISM: Artificial Sequence
<220> FEATURE:
<223> OTHER INFORMATION: antibody sequence

<400> SEQUENCE: 16

Gln Gln His Tyr Ser Ile Pro Arg Thr
1               5

<210> SEQ ID NO 17
<211> LENGTH: 446
<212> TYPE: PRT
<213> ORGANISM: Artificial Sequence
<220> FEATURE:
<223> OTHER INFORMATION: antibody sequence

<400> SEQUENCE: 17

Gln Val Gln Leu Gln Gln Pro Gly Ala Glu Leu Val Met Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Glu Gly Leu Glu Trp Ile
        35                  40                  45

Gly Glu Ile Asp Pro Ser Asp Ser Tyr Thr Asn Asp Asn Gln Lys Phe
    50                  55                  60

Lys Gly Lys Ala Thr Leu Thr Val Asp Lys Ser Ser Ser Thr Ala Tyr
65                  70                  75                  80

```
Met Gln Leu Ser Ser Leu Thr Ser Glu Asp Ser Ala Val Tyr Tyr Cys
                85                  90                  95

Ala Arg Arg Leu Tyr Ser Asn Ser Tyr Tyr Ala Met Asp Tyr Trp
            100                 105                 110

Gly Gln Gly Thr Ser Val Thr Val Ser Ser Ala Lys Thr Thr Pro Pro
            115                 120                 125

Ser Val Tyr Pro Leu Ala Pro Gly Ser Ala Ala Gln Thr Asn Ser Met
130                 135                 140

Val Thr Leu Gly Cys Leu Val Lys Gly Tyr Phe Pro Glu Pro Val Thr
145                 150                 155                 160

Val Thr Trp Asn Ser Gly Ser Leu Ser Ser Gly Val His Thr Phe Pro
                165                 170                 175

Ala Val Leu Gln Ser Asp Leu Tyr Thr Leu Ser Ser Ser Val Thr Val
            180                 185                 190

Pro Ser Ser Thr Trp Pro Ser Gln Thr Val Thr Cys Asn Val Ala His
            195                 200                 205

Pro Ala Ser Ser Thr Lys Val Asp Lys Lys Ile Val Pro Arg Asp Cys
            210                 215                 220

Gly Cys Lys Pro Cys Ile Cys Thr Val Pro Glu Val Ser Ser Val Phe
225                 230                 235                 240

Ile Phe Pro Pro Lys Pro Lys Asp Val Leu Thr Ile Thr Leu Thr Pro
                245                 250                 255

Lys Val Thr Cys Val Val Val Asp Ile Ser Lys Asp Asp Pro Glu Val
            260                 265                 270

Gln Phe Ser Trp Phe Val Asp Asp Val Glu Val His Thr Ala Gln Thr
            275                 280                 285

Lys Pro Arg Glu Glu Gln Ile Asn Ser Thr Phe Arg Ser Val Ser Glu
290                 295                 300

Leu Pro Ile Met His Gln Asp Trp Leu Asn Gly Lys Glu Phe Lys Cys
305                 310                 315                 320

Arg Val Asn Ser Ala Ala Phe Pro Ala Pro Ile Glu Lys Thr Ile Ser
                325                 330                 335

Lys Thr Lys Gly Arg Pro Lys Ala Pro Gln Val Tyr Thr Ile Pro Pro
            340                 345                 350

Pro Lys Glu Gln Met Ala Lys Asp Lys Val Ser Leu Thr Cys Met Ile
            355                 360                 365

Thr Asn Phe Phe Pro Glu Asp Ile Thr Val Glu Trp Gln Trp Asn Gly
370                 375                 380

Gln Pro Ala Glu Asn Tyr Lys Asn Thr Gln Pro Ile Met Asp Thr Asp
385                 390                 395                 400

Gly Ser Tyr Phe Val Tyr Ser Lys Leu Asn Val Gln Lys Ser Asn Trp
                405                 410                 415

Glu Ala Gly Asn Thr Phe Thr Cys Ser Val Leu His Glu Gly Leu His
            420                 425                 430

Asn His His Thr Glu Lys Ser Leu Ser His Ser Pro Gly Lys
            435                 440                 445

<210> SEQ ID NO 18
<211> LENGTH: 213
<212> TYPE: PRT
<213> ORGANISM: Artificial Sequence
<220> FEATURE:
<223> OTHER INFORMATION: antibody sequence

<400> SEQUENCE: 18
```

Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Lys Lys Tyr
            20                  25                  30

Ile Ala Trp Tyr Gln His Lys Pro Gly Lys Gly Pro Arg Leu Leu Ile
            35                  40                  45

His Tyr Thr Ser Thr Leu Gln Pro Gly Ile Pro Ser Arg Phe Ser Gly
    50                  55                  60

Ser Gly Ser Gly Arg Asp Tyr Ser Phe Ser Ile Ser Asn Leu Glu Pro
65              70                  75                  80

Val Asp Ile Ala Thr Tyr Tyr Cys Leu Gln Tyr Asp Asn Leu Leu Thr
                85                  90                  95

Phe Gly Ala Gly Thr Lys Leu Glu Leu Lys Arg Ala Asp Ala Ala Pro
            100                 105                 110

Thr Val Ser Ile Phe Pro Pro Ser Glu Gln Leu Thr Ser Gly Gly
            115                 120                 125

Ala Ser Val Val Cys Phe Leu Asn Asn Phe Tyr Pro Arg Asp Ile Asn
    130                 135                 140

Val Lys Trp Lys Ile Asp Gly Ser Glu Arg Gln Asn Gly Val Leu Asn
145             150                 155                 160

Ser Trp Thr Asp Gln Asp Ser Lys Asp Ser Thr Tyr Asn Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
            195                 200                 205

Asn Arg Asn Glu Cys
    210

<210> SEQ ID NO 19
<211> LENGTH: 444
<212> TYPE: PRT
<213> ORGANISM: Artificial Sequence
<220> FEATURE:
<223> OTHER INFORMATION: antibody sequence

<400> SEQUENCE: 19

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Ser Asp Tyr
            20                  25                  30

Tyr Met His Trp Val Lys Gln Ser His Gly Lys Ser Leu Glu Trp Ile
            35                  40                  45

Gly Tyr Ile Tyr Pro Asp Asn Gly Gly Asn Gly Tyr Asn Gln Lys Phe
    50                  55                  60

Lys Gly Lys Ala Thr Leu Thr Val Asp Lys Ser Ser Ser Thr Val Tyr
65              70                  75                  80

Met Glu Leu Arg Ser Leu Thr Ser Glu Asp Ser Ala Leu Tyr Tyr Cys
                85                  90                  95

Ala Arg Gly Thr Tyr Tyr Asp Gly Ser Tyr Phe Asp Tyr Trp Gly Gln
            100                 105                 110

Gly Thr Thr Leu Thr Val Ser Ser Ala Lys Thr Thr Pro Pro Ser Val
            115                 120                 125

Tyr Pro Leu Ala Pro Gly Ser Ala Ala Gln Thr Asn Ser Met Val Thr
    130                 135                 140

```
Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Val Val Thr Val Pro Ser
            180                 185                 190

Ser Thr Trp Pro Ser Gln Thr Val Thr Cys Asn Val Ala His Pro Ala
            195                 200                 205

Ser Ser Thr Lys Val Asp Lys Lys Ile Val Pro Arg Asp Cys Gly Cys
        210                 215                 220

Lys Pro Cys Ile Cys Thr Val Pro Glu Val Ser Ser Val Phe Ile Phe
225                 230                 235                 240

Pro Pro Lys Pro Lys Asp Val Leu Thr Ile Thr Leu Thr Pro Lys Val
                245                 250                 255

Thr Cys Val Val Val Asp Ile Ser Lys Asp Asp Pro Glu Val Gln Phe
            260                 265                 270

Ser Trp Phe Val Asp Asp Val Glu Val His Thr Ala Gln Thr Lys Pro
        275                 280                 285

Arg Glu Glu Gln Ile Asn Ser Thr Phe Arg Ser Val Ser Glu Leu Pro
290                 295                 300

Ile Met His Gln Asp Trp Leu Asn Gly Lys Glu Phe Lys Cys Arg Val
305                 310                 315                 320

Asn Ser Ala Ala Phe Pro Ala Pro Ile Glu Lys Thr Ile Ser Lys Thr
                325                 330                 335

Lys Gly Arg Pro Lys Ala Pro Gln Val Tyr Thr Ile Pro Pro Pro Lys
            340                 345                 350

Glu Gln Met Ala Lys Asp Lys Val Ser Leu Thr Cys Met Ile Thr Asn
        355                 360                 365

Phe Phe Pro Glu Asp Ile Thr Val Glu Trp Gln Trp Asn Gly Gln Pro
370                 375                 380

Ala Glu Asn Tyr Lys Asn Thr Gln Pro Ile Met Asp Thr Asp Gly Ser
385                 390                 395                 400

Tyr Phe Val Tyr Ser Lys Leu Asn Val Gln Lys Ser Asn Trp Glu Ala
                405                 410                 415

Gly Asn Thr Phe Thr Cys Ser Val Leu His Glu Gly Leu His Asn His
            420                 425                 430

His Thr Glu Lys Ser Leu Ser His Ser Pro Gly Lys
        435                 440

<210> SEQ ID NO 20
<211> LENGTH: 214
<212> TYPE: PRT
<213> ORGANISM: Artificial Sequence
<220> FEATURE:
<223> OTHER INFORMATION: antibody sequence

<400> SEQUENCE: 20

Asp Ile Val Met Thr Gln Ser His Lys Phe Met Ser Thr Leu Val Gly
1               5                   10                  15

Asp Arg Val Ser Ile Thr Cys Lys Ala Ser Gln Asp Val Ser Thr Thr
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60
```

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Ile Pro Arg
            85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Glu Gln Leu Thr Ser Gly
            115                 120                 125

Gly Ala Ser Val Val Cys Phe Leu Asn Asn Phe Tyr Pro Arg Asp Ile
130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
            165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
            195                 200                 205

Phe Asn Arg Asn Glu Cys
    210

<210> SEQ ID NO 21
<211> LENGTH: 452
<212> TYPE: PRT
<213> ORGANISM: Artificial Sequence
<220> FEATURE:
<223> OTHER INFORMATION: antibody sequence

<400> SEQUENCE: 21

Gln Val Gln Leu Gln Gln Pro Gly Ala Glu Leu Val Met Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Glu Gly Leu Glu Trp Ile
            35                  40                  45

Gly Glu Ile Asp Pro Ser Asp Ser Tyr Thr Asn Asp Asn Gln Lys Phe
50                  55                  60

Lys Gly Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
            85                  90                  95

Ala Arg Arg Leu Tyr Ser Asn Ser Tyr Tyr Tyr Ala Met Asp Tyr Trp
            100                 105                 110

Gly Gln Gly Thr Ser Val Thr Val Ser Ser Ala Ser Thr Lys Gly Pro
            115                 120                 125

Ser Val Phe Pro Leu Ala Pro Ser Ser Lys Ser Thr Ser Gly Gly Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Val Glu Pro Lys Ser
        210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 22
<211> LENGTH: 213
<212> TYPE: PRT
<213> ORGANISM: Artificial Sequence
<220> FEATURE:
<223> OTHER INFORMATION: antibody sequence

<400> SEQUENCE: 22

Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Lys Lys Tyr
            20                  25                  30

Ile Ala Trp Tyr Gln His Lys Pro Gly Lys Gly Pro Arg Leu Leu Ile
        35                  40                  45

His Tyr Thr Ser Thr Leu Gln Pro Gly Ile Pro Ser Arg Phe Ser Gly
    50                  55                  60

Ser Gly Ser Gly Arg Asp Tyr Ser Phe Ser Ile Ser Asn Leu Glu Pro
65                  70                  75                  80

Val Asp Ile Ala Thr Tyr Tyr Cys Leu Gln Tyr Asp Asn Leu Leu Thr
                85                  90                  95

Phe Gly Ala Gly Thr Lys Leu Glu Leu Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 23
<211> LENGTH: 450
<212> TYPE: PRT
<213> ORGANISM: Artificial Sequence
<220> FEATURE:
<223> OTHER INFORMATION: antibody sequence

<400> SEQUENCE: 23

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Ser Asp Tyr
            20                  25                  30

Tyr Met His Trp Val Lys Gln Ser His Gly Lys Ser Leu Glu Trp Ile
        35                  40                  45

Gly Tyr Ile Tyr Pro Asp Asn Gly Gly Asn Gly Tyr Asn Gln Lys Phe
    50                  55                  60

Lys Gly Lys Ala Thr Leu Thr Val Asp Lys Ser Ser Ser Thr Val Tyr
65                  70                  75                  80

Met Glu Leu Arg Ser Leu Thr Ser Glu Asp Ser Ala Leu Tyr Tyr Cys
                85                  90                  95

Ala Arg Gly Thr Tyr Tyr Asp Gly Ser Tyr Phe Asp Tyr Trp Gly Gln
            100                 105                 110

Gly Thr Thr Leu Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

```
Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
        340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
        435                 440                 445

Gly Lys
    450

<210> SEQ ID NO 24
<211> LENGTH: 214
<212> TYPE: PRT
<213> ORGANISM: Artificial Sequence
<220> FEATURE:
<223> OTHER INFORMATION: antibody sequence

<400> SEQUENCE: 24

Asp Ile Val Met Thr Gln Ser His Lys Phe Met Ser Thr Leu Val Gly
1               5                   10                  15

Asp Arg Val Ser Ile Thr Cys Lys Ala Ser Gln Asp Val Ser Thr Thr
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Ile Pro Arg
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160
```

```
Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 25
<211> LENGTH: 366
<212> TYPE: DNA
<213> ORGANISM: Artificial Sequence
<220> FEATURE:
<223> OTHER INFORMATION: antibody sequence

<400> SEQUENCE: 25
caggtccaac tgcagcagcc tggggctgag cttgtgatgc ctggggcttc agtgaagctg       60
tcctgcaagg cttctggcta caccttcacc agctactgga tgcactgggt gaagcagagg      120
cctggagaag cccttgagtg gatcggagag attgatcctt ctgatagtta tactaacgac      180
aatcaaaagt tcaagggcaa ggccacattg actgtagaca atcctccag cacagcctac       240 atgcagctca gcagcctgac atctgaggac tctgcggtct attactgtgc aagaaggctc      300
tatagtaact cttattacta tgctatggac tactggggtc aaggaacctc agtcaccgtc      360
tcctca                                                                 366

<210> SEQ ID NO 26
<211> LENGTH: 318
<212> TYPE: DNA
<213> ORGANISM: Artificial Sequence
<220> FEATURE:
<223> OTHER INFORMATION: antibody sequence

<400> SEQUENCE: 26
gacatccaga tgacacagtc tccatcctca ctgtctgcat ctctgggagg caaagtcacc       60
atcacttgca aggcaagcca agacattaag aagtatatag cttggtacca acacaagcct      120
ggaaaaggtc ctaggctgct catacattac acatctacat tacagccagg catcccatca      180
aggttcagtg aagtgggtc tgggagagat tattccttca gcatcagcaa cctggagcct       240
gtggatattg caacttatta ttgtctgcag tatgataatc ttctcacatt cggtgctggg      300
accaagctgg agctgaaa                                                    318

<210> SEQ ID NO 27
<211> LENGTH: 360
<212> TYPE: DNA
<213> ORGANISM: Artificial Sequence
<220> FEATURE:
<223> OTHER INFORMATION: antibody sequence

<400> SEQUENCE: 27
gaggtccagc tgcaacagtc tggacctgag ttggtgaagc ctggggcttc agtgaagatg       60
tcctgcaagg cttctggcta cacattcagt gactactaca tgcactgggt gaagcagagc      120
catggaaaga gccttgagtg gattggatat atttatcctg acaatggtgg taatggctac      180
aaccagaagt tcaagggcaa ggccacattg actgtagaca gtcctccag cacagtctac       240 atggagctcc gcagcctgac atctgaggac tctgcactct attactgtgc aagagggacc      300
```

```
tactatgatg gttcctactt tgactactgg ggccaaggca ccactctcac agtctcctca    360

<210> SEQ ID NO 28
<211> LENGTH: 321
<212> TYPE: DNA
<213> ORGANISM: Artificial Sequence
<220> FEATURE:
<223> OTHER INFORMATION: antibody sequence

<400> SEQUENCE: 28
gacattgtga tgacccagtc tcacaaattc atgtccacat tagtaggaga cagggtcagc     60
atcacctgca aggccagtca ggatgtgagt actactgtag cctggtatca acagaaacca    120
ggacaatctc ctaaactact gatttactcg gcatcctacc ggtacactgg agtccctgat    180
cgcttcactg gcagtggatc tgggacggat ttcactttca ccatcagcag tgtgcaggct    240
gaagacctgg cagtttatta ctgtcaacaa cattatagta ttcctcggac gttcggtgga    300
ggcaccaagc tggaaatcaa a                                              321

<210> SEQ ID NO 29
<211> LENGTH: 1338
<212> TYPE: DNA
<213> ORGANISM: Artificial Sequence
<220> FEATURE:
<223> OTHER INFORMATION: antibody sequence

<400> SEQUENCE: 29
caggtccaac tgcagcagcc tggggctgag cttgtgatgc ctggggcttc agtgaagctg     60
tcctgcaagg cttctggcta caccttcacc agctactgga tgcactgggt gaagcagagg    120
cctggagaag ccttgagtg gatcggagag attgatcctt ctgatagtta tactaacgac    180
aatcaaaagt tcaagggcaa ggccacattg actgtagaca atcctccag cacagcctac     240 atgcagctca gcagcctgac atctgaggac tctgcggtct attactgtgc aagaaggctc    300
tatagtaact cttattacta tgctatggac tactggggtc aaggaacctc agtcaccgtc    360
tcctcagcca aaacgacacc cccatctgtc tatccactgg cccctggatc tgctgcccaa    420
actaactcca tggtgaccct gggatgcctg gtcaagggct atttccctga gccagtgaca    480
gtgacctgga actctggatc cctgtccagc ggtgtgcaca ccttcccagc tgtcctgcag    540
tctgacctct acactctgag cagctcagtg actgtcccct ccagcacctg cccagccag    600 accgtcacct gcaacgttgc cacccggcc agcagcacca aggtggacaa gaaaattgtg    660
cccagggatt gtggttgtaa gccttgcata tgtacagtcc cagaagtatc atctgtcttc    720
atcttccccc caaagcccaa ggatgtgctc accattactc tgactcctaa ggtcacgtgt    780
gttgtggtag acatcagcaa ggatgatccc gaggtccagt tcagctggtt tgtagatgat    840
gtggaggtgc acacagctca gacgaaaccc gggaggagc agatcaacag cactttccgt    900
tcagtcagtg aacttcccat catgcaccag gactggctca atggcaagga gttcaaatgc    960
agggtcaaca gtgcagcttt ccctgccccc atcgagaaaa ccatctccaa aaccaaaggc   1020
agaccgaagg ctccacaggt gtacaccatt ccacctccca aggagcagat ggccaaggat   1080
aaagtcagtc tgacctgcat gataacaaac ttcttccctg aagacattac tgtggagtgg   1140
cagtggaatg ggcagccagc ggagaactac aagaacactc agcccatcat ggacacagat   1200
ggctcttact tcgtctacag caagctcaat gtgcagaaga caactgggaa ggcaggaaat   1260
actttcacct gctctgtgtt acatgagggc ctgcacaacc accatactga gaagagcctc   1320
tcccactctc ctggtaaa                                                 1338
```

<210> SEQ ID NO 30
<211> LENGTH: 639
<212> TYPE: DNA
<213> ORGANISM: Artificial Sequence
<220> FEATURE:
<223> OTHER INFORMATION: antibody sequence

<400> SEQUENCE: 30

```
gacatccaga tgacacagtc tccatcctca ctgtctgcat ctctgggagg caaagtcacc      60
atcacttgca aggcaagcca agacattaag aagtatatag cttggtacca acacaagcct     120
ggaaaaggtc ctaggctgct catacattac acatctacat tacagccagg catcccatca     180
aggttcagtg aagtgggtc tgggagagat tattccttca gcatcagcaa cctggagcct      240
gtggatattg caacttatta ttgtctgcag tatgataatc ttctcacatt cggtgctggg     300
accaagctgg agctgaaacg gctgatgct gcaccaactg tatccatctt cccaccatcc      360
agtgagcagt taacatctgg aggtgcctca gtcgtgtgct tcttgaacaa cttctacccc     420
agagacatca atgtcaagtg aagattgat ggcagtgaac gacaaaatgg tgtcctgaac       480
agttggactg atcaggacag caaagacagc acctacaaca tgagcagcac cctcacattg     540
accaaggacg agtatgaacg ataaacagc tatacctgtg aggccactca caagacatca      600
acttcaccca tcgtcaagag cttcaacagg aatgagtgt                            639
```

<210> SEQ ID NO 31
<211> LENGTH: 1332
<212> TYPE: DNA
<213> ORGANISM: Artificial Sequence
<220> FEATURE:
<223> OTHER INFORMATION: antibody sequence

<400> SEQUENCE: 31

```
gaggtccagc tgcaacagtc tggacctgag ttggtgaagc ctggggcttc agtgaagatg      60
tcctgcaagg cttctggcta cacattcagt gactactaca tgcactgggt gaagcagagc     120
catggaaaga gccttgagtg gattggatat atttatcctg acaatggtgg taatggctac     180
aaccagaagt tcaagggcaa ggccacattg actgtagaca agtcctccag cacagtctac     240
atggagctcc gcagcctgac atctgaggac tctgcactct attactgtgc aagagggacc     300
tactatgatg ttcctacttt tgactactgg ggccaaggca ccactctcac agtctcctca     360
gccaaaacga cacccccatc tgtctatcca ctggcccctg gatctgctgc ccaaactaac     420
tccatggtga ccctgggatg cctggtcaag ggctatttcc ctgagccagt gacagtgacc     480
tggaactctg gatccctgtc agcggtgtg cacaccttcc cagctgtcct gcagtctgac       540
ctctacactc tgagcagctc agtgactgtc ccctccagca cctggcccag ccagaccgtc     600
acctgcaacg ttgcccaccc ggccagcagc accaaggtgg acaagaaaat tgtgcccagg     660
gattgtggtt gtaagccttg catatgtaca gtcccagaag tatcatctgt cttcatcttc     720
cccccaaagc ccaaggatgt gctcaccatt actctgactc ctaaggtcac gtgtgttgtg     780
gtagacatca gcaaggatga tcccgaggtc cagttcagct ggtttgtaga tgatgtggag     840
gtgcacacag ctcagacgaa accccgggag gagcagatca cagcactttt ccgttcagtc     900
agtgaacttc ccatcatgca ccaggactgg ctcaatggca aggagttcaa atgcagggtc     960
aacagtgcag ctttccctgc ccccatcgag aaaaccatct ccaaaaccaa aggcagaccg    1020
aaggctccac aggtgtacac cattccacct cccaaggagc agatggccaa ggataaagtc    1080
```

| | |
|---|---:|
| agtctgacct gcatgataac aaacttcttc cctgaagaca ttactgtgga gtggcagtgg | 1140 |
| aatgggcagc cagcggagaa ctacaagaac actcagccca tcatggacac agatggctct | 1200 |
| tacttcgtct acagcaagct caatgtgcag aagagcaact gggaggcagg aaatactttc | 1260 |
| acctgctctg tgttacatga gggcctgcac aaccaccata ctgagaagag cctctcccac | 1320 |
| tctcctggta aa | 1332 |

<210> SEQ ID NO 32
<211> LENGTH: 642
<212> TYPE: DNA
<213> ORGANISM: Artificial Sequence
<220> FEATURE:
<223> OTHER INFORMATION: antibody sequence

<400> SEQUENCE: 32

| | |
|---|---:|
| gacattgtga tgacccagtc tcacaaattc atgtccacat tagtaggaga cagggtcagc | 60 |
| atcacctgca aggccagtca ggatgtgagt actactgtag cctggtatca acagaaacca | 120 |
| ggacaatctc ctaaactact gatttactcg gcatcctacc ggtacactgg agtccctgat | 180 |
| cgcttcactg gcagtggatc tgggacggat ttcactttca ccatcagcag tgtgcaggct | 240 |
| gaagacctgg cagtttatta ctgtcaacaa cattatagta ttcctcggac gttcggtgga | 300 |
| ggcaccaagc tggaaatcaa acgggctgat gctgcaccaa ctgtatccat cttcccacca | 360 |
| tccagtgagc agttaacatc tggaggtgcc tcagtcgtgt gcttcttgaa caacttctac | 420 |
| cccagagaca tcaatgtcaa gtggaagatt gatggcagtg aacgacaaaa tggtgtcctg | 480 |
| aacagttgga ctgatcagga cagcaaagac agcacctaca gcatgagcag cacccctcaca | 540 |
| ttgaccaagg acgagtatga acgacataac agctatacct gtgaggccac tcacaagaca | 600 |
| tcaacttcac ccatcgtcaa gagcttcaac aggaatgagt gt | 642 |

<210> SEQ ID NO 33
<211> LENGTH: 1356
<212> TYPE: DNA
<213> ORGANISM: Artificial Sequence
<220> FEATURE:
<223> OTHER INFORMATION: antibody sequence

<400> SEQUENCE: 33

| | |
|---|---:|
| caggtccagc tgcagcagcc cggagccgaa ctggtcatgc ccggcgccag cgtgaagctg | 60 |
| tcctgcaagg cttctggcta taccttcaca tcctactgga tgcactgggt gaagcagaga | 120 |
| cccgagagg gactggagtg gatcggcgag atcgacccat ccgattctta taccaacgac | 180 |
| aatcagaagt ttaagggcaa ggccaccctg acagtggata gagctcctc taccgcttat | 240 |
| atgcagctga gctccctgac aagcgaggac tccgccgtgt actattgcgc tcggaggctg | 300 |
| tatagcaact cctactatta cgccatggat tactggggcc agggcaccag cgtgacagtg | 360 |
| tctagcgcca gcaccaaggg cccttccgtg ttcccactgg ctccctcctc taaatctacc | 420 |
| agcggaggaa cagccgctct gggatgtctg gtgaaggact acttcccaga gcccgtgaca | 480 |
| gtgtcttgga acagcggcgc cctgacctcc ggcgtgcaca catttcctgc tgtgctgcag | 540 |
| agctccggcc tgtattctct gtctagcgtg gtgaccgtgc catcctctag cctgggcacc | 600 |
| cagacataca tctgcaacgt gaatcacaag ccatccaata caaaggtgga caagaaggtc | 660 |
| gagcccaagt cttgtgataa gacccacaca tgccccccctt gtcctgctcc agagctgctg | 720 |
| ggaggaccctt ccgtgttcct gtttccaccc aaacctaagg acaccctgat gatcagccgg | 780 |
| accccagagg tgacatgcgt ggtggtggac gtgtcccacg aggatcccga ggtgaagttt | 840 |

| | | |
|---|---|---|
| aactggtacg tcgatggcgt ggaggtgcac aatgctaaga ccaagcccag agaggagcag | 900 | |
| tataactcta cctaccgggt ggtgagcgtg ctgacagtgc tgcaccagga ctggctgaac | 960 | |
| ggcaaggagt acaagtgcaa ggtgtctaat aaggccctgc ccgctcccat cgagaagacc | 1020 | |
| atcagcaagg ccaagggcca gcctagggag ccacaggtgt atacactgcc tccatctaga | 1080 | |
| gacgagctga ccaagaacca ggtgagcctg acatgtctgg tgaagggctt ctaccccagc | 1140 | |
| gatatcgccg tggagtggga gtccaatggc cagcctgaga caattataa gaccacaccc | 1200 | |
| cctgtgctgg actccgatgg ctctttcttt ctgtactcca agctgaccgt ggataagtct | 1260 | |
| aggtggcagc agggcaacgt gttcagctgt tctgtgatgc acgaagctct gcataatcac | 1320 | |
| tacacccaga aaagcctgtc cctgtcacct ggtaaa | 1356 | |

<210> SEQ ID NO 34
<211> LENGTH: 639
<212> TYPE: DNA
<213> ORGANISM: Artificial Sequence
<220> FEATURE:
<223> OTHER INFORMATION: antibody sequence

<400> SEQUENCE: 34

| | | |
|---|---|---|
| gatattcaga tgactcagtc cccttcttca ctgtctgcca gcctgggcgg caaggtgacc | 60 | |
| atcacatgca aggcctccca ggacatcaag aagtacatcg cttggtatca gcacaagcct | 120 | |
| ggcaagggcc cacggctgct gatccactac acctctacac tgcagccagg catcccagc | 180 | |
| cggttctccg gaagcggaag cggaagggat tactcctttt ctatcagcaa cctggagccc | 240 | |
| gtggacatcg ccacctacta ttgcctgcag tatgataatc tgctgacctt cggcgctggc | 300 | |
| acaaagctgg agctgaagag aaccgtggcc gctcccagcg tgttcatctt cccccttcc | 360 | |
| gacgagcagc tgaagtccgg cacagcttct gtggtgtgcc tgctgaacaa cttctaccct | 420 | |
| cgggaggcca aggtgcagtg gaaggtggat aacgctctgc agtccggcaa ttctcaggag | 480 | |
| agcgtgaccg agcaggactc caaggattct acatatagcc tgagctccac cctgacactg | 540 | |
| tctaaggccg actacgagaa gcacaaggtg tatgcttgtg aagtgactca tcagggtctg | 600 | |
| tcatcacccg tgactaaatc attcaataga ggcgaatgc | 639 | |

<210> SEQ ID NO 35
<211> LENGTH: 1350
<212> TYPE: DNA
<213> ORGANISM: Artificial Sequence
<220> FEATURE:
<223> OTHER INFORMATION: antibody sequence

<400> SEQUENCE: 35

| | | |
|---|---|---|
| gaagtccagc tgcagcagtc tggtcctgaa ctggtgaagc ctggcgcctc cgtgaagatg | 60 | |
| tcttgcaagg ctagcggcta caccttcagc gactactata tgcactgggt gaagcagtcc | 120 | |
| cacggcaagt ctctggagtg gatcggctac atctatccag ataacggcgg caatggctac | 180 | |
| aaccagaagt ttaagggcaa ggccaccctg acagtggaca gagctcctc taccgtgtat | 240 | |
| atggagctga ggagcctgac atccgaggat tctgccctgt actattgcgc tagaggcacc | 300 | |
| tactatgacg gctcctactt cgattattgg ggccagggca ccacactgac cgtgagctcc | 360 | |
| gccagcacaa agggcccctc cgtgtttcca ctggctccct cttccaagtc taccagcgga | 420 | |
| ggaacagccg ctctgggatg tctggtgaag gactacttcc cagagcccgt gaccgtgagc | 480 | |
| tggaacagcg gcgccctgac ctccggcgtg cacacatttc cagctgtgct gcagtcctct | 540 | |

```
ggcctgtact ctctgagctc cgtggtgacc gtgccctcta gctccctggg cacccagaca    600
tatatctgca acgtgaatca caagccatcc aacacaaagg tggacaagaa ggtcgagccc    660
aagtcttgtg ataagaccca cacatgcccc ccttgtcctg ctcccgagct gctgggagga    720
cctagcgtgt tcctgtttcc acccaagcct aaggacaccc tgatgatcag ccggaccccc    780
gaggtgacat gcgtggtggt ggacgtgtcc cacgaggatc ctgaggtgaa gttcaattgg    840
tatgtcgatg gcgtggaggt gcacaacgct aagacaaagc ctcggaggga gcagtacaat    900
tctacctata gggtggtgag cgtgctgaca gtgctgcacc aggactggct caatggcaag    960
gagtataagt gcaaggtgtc taacaaggcc ctgcccgctc ctatcgagaa gaccatcagc   1020
aaggccaagg gccagcctag agagccacag gtgtacacac tgcctccatc tcgggacgag   1080
ctgaccaaga atcaggtgag cctgacatgt ctggtgaagg gcttctatcc tagcgatatc   1140
gccgtggagt gggagtccaa cggccagcca gagaacaatt acaagaccac ccccctgtg   1200 ctggactctg atggcagctt ctttctgtat ccaagctga ccgtggataa gtctaggtgg    1260
cagcagggca acgtgttttc ctgttctgtg atgcacgaag ccctgcataa tcactatact   1320
cagaaatccc tgtcactgtc acctggtaaa                                    1350

<210> SEQ ID NO 36
<211> LENGTH: 642
<212> TYPE: DNA
<213> ORGANISM: Artificial Sequence
<220> FEATURE:
<223> OTHER INFORMATION: antibody sequence

<400> SEQUENCE: 36
gacattgtga tgactcagtc ccataaattc atgtctaccc tggtgggcga ccgggtgagc     60
atcacatgca aggcctctca ggatgtgagc accacagtgg cttggtacca gcagaagcca    120
ggccagtccc ccaagctgct gatctattcc gcctcttatc ggtataccgg agtgcctgac    180
aggttcaccg gaagcggatc cggcacagat ttcacccttta caatcagctc cgtgcaggcc    240
gaggacctgg ccgtgtacta ttgccagcag cactactcta tccctagaac cttttggcggc    300 ggcacaaagc tggagatcaa gcggaccgtg gccgctccaa gcgtgttcat cttcccccct    360
tccgacgagc agctgaagtc cggcacagct tctgtggtgt gcctgctgaa caatttctac    420
cccagggagg ccaaggtcca gtggaaggtg gataacgctc tgcagtctgg caatagccag    480
gagtccgtga ccgagcagga ctctaaggat agcacatatt ccctgtctag cacccttgaca    540 ctgagcaagg ccgattacga gaagcacaag gtgtatgctt gtgaagtcac tcatcagggt    600
ctgtcttcac ctgtcactaa gtcttttaac cgaggcgaat gc                       642

<210> SEQ ID NO 37
<211> LENGTH: 15
<212> TYPE: PRT
<213> ORGANISM: Artificial Sequence
<220> FEATURE:
<223> OTHER INFORMATION: Chimeric antigen receptor sequence

<400> SEQUENCE: 37

Gly Gly Gly Gly Ser Gly Gly Gly Gly Ser Gly Gly Gly Gly Ser
1               5                   10                  15

<210> SEQ ID NO 38
<211> LENGTH: 22
<212> TYPE: PRT
<213> ORGANISM: Artificial Sequence
<220> FEATURE:
```

<223> OTHER INFORMATION: Chimeric antigen receptor sequence

<400> SEQUENCE: 38

Leu Leu Val Thr Ser Leu Leu Leu Cys Glu Leu Pro His Pro Ala Phe
1               5                   10                  15

Leu Leu Ile Pro Asp Thr
            20

<210> SEQ ID NO 39
<211> LENGTH: 236
<212> TYPE: PRT
<213> ORGANISM: Artificial Sequence
<220> FEATURE:
<223> OTHER INFORMATION: Chimeric antigen receptor sequence

<400> SEQUENCE: 39

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys Lys Asp Pro Lys
225                 230                 235

<210> SEQ ID NO 40
<211> LENGTH: 69
<212> TYPE: PRT
<213> ORGANISM: Artificial Sequence
<220> FEATURE:
<223> OTHER INFORMATION: Chimeric antigen receptor sequence

<400> SEQUENCE: 40

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly

```
                    20                  25                  30

Gly Ala Val His Thr Arg Gly Leu Asp Phe Ala Cys Asp Ile Tyr Ile
            35                  40                  45

Trp Ala Pro Leu Ala Gly Thr Cys Gly Val Leu Leu Leu Ser Leu Val
        50                  55                  60

Ile Thr Leu Tyr Cys
65

<210> SEQ ID NO 41
<211> LENGTH: 67
<212> TYPE: PRT
<213> ORGANISM: Artificial Sequence
<220> FEATURE:
<223> OTHER INFORMATION: Chimeric antigen receptor sequence

<400> SEQUENCE: 41

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
        35                  40                  45

Val Leu Ala Cys Tyr Ser Leu Leu Val Thr Val Ala Phe Ile Ile Phe
    50                  55                  60

Trp Val Arg
65

<210> SEQ ID NO 42
<211> LENGTH: 112
<212> TYPE: PRT
<213> ORGANISM: Artificial Sequence
<220> FEATURE:
<223> OTHER INFORMATION: Chimeric antigen receptor sequence

<400> SEQUENCE: 42

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 43
<211> LENGTH: 84
<212> TYPE: PRT
<213> ORGANISM: Artificial Sequence
<220> FEATURE:
<223> OTHER INFORMATION: Chimeric antigen receptor sequence

<400> SEQUENCE: 43

Phe Val Pro Val Phe Leu Pro Ala Lys Pro Thr Thr Thr Pro Ala Pro
1               5                   10                  15
```

Arg Pro Pro Thr Pro Ala Pro Thr Ile Ala Ser Gln Pro Leu Ser Leu
            20                  25                  30

Arg Pro Glu Ala Cys Arg Pro Ala Ala Gly Gly Ala Val His Thr Arg
        35                  40                  45

Gly Leu Asp Phe Ala Cys Asp Ile Tyr Ile Trp Ala Pro Leu Ala Gly
    50                  55                  60

Thr Cys Gly Val Leu Leu Leu Ser Leu Val Ile Thr Leu Tyr Cys Asn
65                  70                  75                  80

His Arg Asn Arg

<210> SEQ ID NO 44
<211> LENGTH: 40
<212> TYPE: PRT
<213> ORGANISM: Artificial Sequence
<220> FEATURE:
<223> OTHER INFORMATION: Chimeric antigen receptor sequence

<400> SEQUENCE: 44

Ser Lys Arg Ser Arg Leu Leu His Ser Asp Tyr Met Asn Met Thr Pro
1               5                   10                  15

Arg Arg Pro Gly Pro Thr Arg Lys His Tyr Gln Pro Tyr Ala Pro Pro
            20                  25                  30

Arg Asp Phe Ala Ala Tyr Arg Ser
        35                  40

<210> SEQ ID NO 45
<211> LENGTH: 42
<212> TYPE: PRT
<213> ORGANISM: Artificial Sequence
<220> FEATURE:
<223> OTHER INFORMATION: Chimeric antigen receptor sequence

<400> SEQUENCE: 45

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 46
<211> LENGTH: 47
<212> TYPE: PRT
<213> ORGANISM: Artificial Sequence
<220> FEATURE:
<223> OTHER INFORMATION: Chimeric antigen receptor sequence

<400> SEQUENCE: 46

Arg Phe Ser Val Val Lys Arg Gly Arg Lys Lys Leu Leu Tyr Ile Phe
1               5                   10                  15

Lys Gln Pro Phe Met Arg Pro Val Gln Thr Thr Gln Glu Glu Asp Gly
            20                  25                  30

Cys Ser Cys Arg Phe Pro Glu Glu Glu Glu Gly Gly Cys Glu Leu
        35                  40                  45

<210> SEQ ID NO 47
<211> LENGTH: 5
<212> TYPE: PRT
<213> ORGANISM: Artificial Sequence
<220> FEATURE:
<223> OTHER INFORMATION: Peptide linker

```
<400> SEQUENCE: 47

Gly Gly Gly Gly Ser
1               5

<210> SEQ ID NO 48
<211> LENGTH: 10
<212> TYPE: PRT
<213> ORGANISM: Artificial Sequence
<220> FEATURE:
<223> OTHER INFORMATION: Peptide linker

<400> SEQUENCE: 48

Gly Gly Gly Gly Ser Gly Gly Gly Gly Ser
1               5                   10

<210> SEQ ID NO 49
<211> LENGTH: 15
<212> TYPE: PRT
<213> ORGANISM: Artificial Sequence
<220> FEATURE:
<223> OTHER INFORMATION: Peptide linker

<400> SEQUENCE: 49

Gly Gly Gly Gly Ser Gly Gly Gly Gly Ser Gly Gly Gly Gly Ser
1               5                   10                  15
```